(12) United States Patent
George et al.

(10) Patent No.: US 12,178,966 B2
(45) Date of Patent: Dec. 31, 2024

(54) SYSTEMS AND METHODS FOR TREATING NEUROLOGICAL DISORDERS

(71) Applicant: NOCIRA, LLC, Tempe, AZ (US)

(72) Inventors: David Mager George, Scottsdale, AZ (US); John Patrick Claude, Redwood City, CA (US); Kevin E. Willey, Fort Collins, CO (US); Andy Edward Denison, Temecula, CA (US); Darrin James Kent, Murrieta, CA (US)

(73) Assignee: NOCIRA, LLC, Tempe, AZ (US)

( * ) Notice: Subject to any disclaimer, the term of this patent is extended or adjusted under 35 U.S.C. 154(b) by 903 days.

(21) Appl. No.: 17/117,463

(22) Filed: Dec. 10, 2020

(65) Prior Publication Data

US 2021/0330928 A1 Oct. 28, 2021

Related U.S. Application Data

(63) Continuation of application No. PCT/US2019/038331, filed on Jun. 20, 2019.
(Continued)

(51) Int. Cl.
*A61M 21/00* (2006.01)
*A61F 7/00* (2006.01)
*A61H 9/00* (2006.01)

(52) U.S. Cl.
CPC ............. *A61M 21/00* (2013.01); *A61F 7/00* (2013.01); *A61H 9/0078* (2013.01);
(Continued)

(58) Field of Classification Search
CPC ............. A61F 2007/0005; A61F 11/12; A61F 2250/0069; A61H 2205/027; A61H 21/00;
(Continued)

(56) References Cited

U.S. PATENT DOCUMENTS 787,443 A 4/1905 Godman et al.
841,146 A 1/1907 Hasbrouck
(Continued)

FOREIGN PATENT DOCUMENTS

CA 1136751 11/1982
CA 1222464 6/1987
(Continued)

OTHER PUBLICATIONS

Akerman, et al. Pearls and pitfalls in experimental in vivo models of migraine: Dural trigeminovascular nociception. Cephalalgia, 2013, 33 (8), pp. 557-592.
(Continued)

*Primary Examiner* — Thaddeus B Cox
(74) *Attorney, Agent, or Firm* — Knobbe Martens Olson & Bear LLP

(57) ABSTRACT

Caloric stimulation and pressure stimulation can be applied to the ear for treatment of neurological disorders, such as migraine, pain, and headache. Heat can be applied first to increase the sensitivity of the mechanoreceptors in the ear. The pressure can be applied after heating to produce a stronger neurological response than would occur without the heating. In some cases, cooling can be used. Valves can be used to direct fluid flow to a right ear, a left ear, or both. Valves can be used to transition the system between an irrigation or caloric mode and a pressure mode. Green eyewear can be used for therapeutic relief.

16 Claims, 24 Drawing Sheets

Related U.S. Application Data

(60) Provisional application No. 62/688,984, filed on Jun. 22, 2018.

(52) U.S. Cl.
CPC .......... A61F 2007/0005 (2013.01); A61F 2007/0054 (2013.01); A61H 2201/0242 (2013.01); A61H 2201/1238 (2013.01); A61H 2201/165 (2013.01); A61H 2205/027 (2013.01); A61M 2021/0022 (2013.01); A61M 2021/0066 (2013.01); A61M 2209/088 (2013.01)

(58) Field of Classification Search
CPC .............. A61H 23/02; A61H 23/04; A61H 2201/0153; A61H 2201/1207; A61H 2201/5071; A61M 13/003; A61M 2205/3344; A61M 2205/362; A61M 2210/0662; H04R 1/42
See application file for complete search history.

(56) References Cited

U.S. PATENT DOCUMENTS

| | | |
|---|---|---|
| 853,645 A | 5/1907 | Meyer |
| 2,176,366 A | 10/1939 | Smith |
| 2,437,490 A | 3/1948 | Watson et al. |
| 2,570,675 A | 10/1951 | Morris |
| 2,652,048 A | 9/1953 | Joers |
| 3,757,769 A | 9/1973 | Arguimbau et al. |
| 3,872,559 A | 3/1975 | Leight |
| 4,002,161 A | 1/1977 | Klar et al. |
| 4,133,984 A | 1/1979 | Watson et al. |
| 4,160,449 A | 7/1979 | Wade |
| 4,206,756 A | 6/1980 | Grossan |
| 4,244,377 A | 1/1981 | Grams |
| 4,289,143 A | 9/1981 | Canavesio et al. |
| 4,325,386 A | 4/1982 | Katz |
| 4,349,083 A | 9/1982 | Bennett |
| 4,472,342 A | 9/1984 | Carr |
| 4,552,137 A | 11/1985 | Strauss |
| 4,594,058 A | 6/1986 | Fischell |
| 4,632,104 A | 12/1986 | Conrow |
| 4,667,676 A | 5/1987 | Guinta |
| 4,688,582 A | 8/1987 | Heller et al. |
| 4,754,748 A | 7/1988 | Antowski |
| 4,757,807 A | 7/1988 | Densert et al. |
| 4,775,370 A | 10/1988 | Berry |
| 4,809,708 A | 3/1989 | Geisler et al. |
| 4,896,380 A | 1/1990 | Kamitani |
| 4,896,679 A | 1/1990 | St. Pierre |
| 4,964,769 A | 10/1990 | Hass |
| 4,984,579 A | 1/1991 | Burgert et al. |
| 5,024,612 A | 6/1991 | van den Honert et al. |
| 5,105,822 A | 4/1992 | Stevens et al. |
| 5,131,411 A | 7/1992 | Casali et al. |
| 5,228,431 A | 7/1993 | Giarretto |
| 5,241,967 A | 9/1993 | Yasushi et al. |
| 5,421,818 A | 6/1995 | Arenberg |
| 5,431,636 A | 7/1995 | Stangerup |
| 5,467,784 A | 11/1995 | Mobley et al. |
| 5,476,446 A | 12/1995 | Arenburg |
| 5,483,027 A | 1/1996 | Krause |
| 5,483,975 A | 1/1996 | Hirschebain |
| 5,488,961 A | 2/1996 | Adams |
| 5,631,965 A | 5/1997 | Chang et al. |
| 5,699,809 A | 12/1997 | Combs et al. |
| 5,740,258 A | 4/1998 | Goodwin-Johansson |
| 5,746,725 A | 5/1998 | Shalon et al. |
| 5,755,234 A | 5/1998 | Mobley et al. |
| 5,769,891 A | 6/1998 | Clayton |
| 5,776,179 A | 7/1998 | Ren et al. |
| 5,819,745 A | 10/1998 | Mobley et al. |
| 5,865,183 A | 2/1999 | Hirschebain |
| 5,868,682 A | 2/1999 | Combe et al. |
| 5,944,711 A | 8/1999 | Pender |
| 6,004,274 A | 12/1999 | Nolan et al. |
| 6,016,499 A | 1/2000 | Ferguson |
| 6,024,726 A | 2/2000 | Hill |
| 6,129,174 A | 10/2000 | Brown et al. |
| 6,139,507 A | 10/2000 | Jeng |
| 6,159,171 A | 12/2000 | Densert et al. |
| 6,186,959 B1 | 2/2001 | Canfield et al. |
| 6,258,067 B1 | 7/2001 | Hill |
| 6,296,652 B1 | 10/2001 | Qingmin |
| 6,359,993 B2 | 3/2002 | Birmhall |
| 6,430,443 B1 | 8/2002 | Karell |
| 6,511,437 B1 | 1/2003 | Nakamura et al. |
| 6,592,512 B2 | 7/2003 | Stöckert et al. |
| 6,629,938 B1 | 10/2003 | Engvall et al. |
| 6,725,568 B2 | 4/2004 | Gronka |
| 6,748,275 B2 | 6/2004 | Lattner et al. |
| 6,800,062 B2 | 10/2004 | Epley |
| 6,820,717 B2 | 11/2004 | Fleming et al. |
| 6,878,128 B2 | 4/2005 | MacMahon et al. |
| 6,958,043 B2 | 10/2005 | Hissong |
| 6,981,569 B2 | 1/2006 | Stilp |
| 7,022,090 B1 | 4/2006 | Engvall et al. |
| 7,162,039 B1 | 1/2007 | Callahan |
| 7,179,238 B2 | 2/2007 | Hissong |
| 7,189,252 B2 | 3/2007 | Krueger |
| 7,268,466 B2 | 9/2007 | Rasmussen |
| 7,352,871 B1 | 4/2008 | Mozo |
| D570,457 S | 6/2008 | Brown |
| 7,613,519 B2 | 11/2009 | De Ridder |
| 7,766,858 B2 | 8/2010 | Franz et al. |
| 7,779,844 B2 | 8/2010 | Purcell et al. |
| 7,785,346 B2 | 8/2010 | Blumberg |
| 7,797,042 B2 | 9/2010 | Dietrich et al. |
| 7,833,282 B2 | 11/2010 | Mandpe |
| 7,892,180 B2 | 2/2011 | Epley |
| 7,959,597 B2 | 6/2011 | Baker et al. |
| 7,988,657 B2 | 8/2011 | Shapiro et al. |
| 8,020,563 B2 | 9/2011 | Pfanstiehl |
| 8,047,207 B2 | 11/2011 | Perez et al. |
| 8,052,693 B2 | 11/2011 | Shahoian |
| 8,122,892 B2 | 2/2012 | Johnson et al. |
| 8,142,373 B1 | 3/2012 | Riles |
| 8,199,919 B2 | 6/2012 | Goldstein et al. |
| 8,241,224 B2 | 8/2012 | Keefe |
| 8,249,285 B2 | 8/2012 | Killion et al. |
| 8,251,925 B2 | 8/2012 | Keady et al. |
| 8,262,717 B2 | 9/2012 | Rogers et al. |
| 8,267,983 B2 | 9/2012 | Rogers et al. |
| 8,267,984 B2 | 9/2012 | Rogers |
| 8,328,830 B1 | 12/2012 | Pandit |
| 8,398,562 B2 | 3/2013 | Keller |
| 8,414,521 B2 | 4/2013 | Baker et al. |
| 8,442,632 B2 | 5/2013 | Kullok et al. |
| 8,460,356 B2 | 6/2013 | Rogers et al. |
| 8,506,469 B2 | 8/2013 | Dietrich et al. |
| 8,515,552 B2 | 8/2013 | Englehart |
| 8,550,206 B2 | 10/2013 | Keady et al. |
| 8,568,348 B2 | 10/2013 | Vlodaver |
| 8,603,152 B2 | 12/2013 | Smith et al. |
| 8,625,833 B1 | 1/2014 | Armwood |
| 8,666,502 B2 | 3/2014 | Hartlep et al. |
| 8,688,239 B2 | 4/2014 | Hartlep et al. |
| 8,696,724 B2 | 4/2014 | Rogers |
| 8,858,430 B2 | 10/2014 | Oyadiran et al. |
| 8,963,914 B2 | 2/2015 | Rawat et al. |
| 9,039,639 B2 | 5/2015 | George et al. |
| 9,168,171 B2 | 10/2015 | Rogers |
| 9,186,277 B2 | 11/2015 | George et al. |
| 9,283,111 B2 | 3/2016 | Rogers et al. |
| 9,526,653 B2 | 12/2016 | Rogers et al. |
| 9,532,900 B2 | 1/2017 | Smith et al. |
| 9,579,247 B2 | 2/2017 | Juto et al. |
| 9,655,772 B2 | 5/2017 | Smith et al. |
| 9,744,074 B2 | 8/2017 | Rogers |
| 9,849,026 B2 | 12/2017 | Rogers et al. |
| 10,076,464 B2 | 9/2018 | George et al. |
| 10,251,790 B2 | 4/2019 | George et al. |

(56) References Cited

U.S. PATENT DOCUMENTS

| | | |
|---|---|---|
| 10,271,992 B2 | 4/2019 | Hayahi et al. |
| 10,278,868 B2 | 5/2019 | George et al. |
| 10,376,695 B2 | 8/2019 | Ericco et al. |
| 10,760,566 B2 | 9/2020 | George et al. |
| 10,772,766 B2 | 9/2020 | Sullivan |
| 11,065,444 B2 | 7/2021 | Ericco et al. |
| 11,090,194 B2 | 8/2021 | George et al. |
| 11,096,828 B2 | 8/2021 | George et al. |
| 11,246,793 B2 | 2/2022 | George et al. |
| 11,859,606 B2 | 1/2024 | George et al. |
| 12,016,816 B2 | 6/2024 | George et al. |
| 2001/0025191 A1 | 9/2001 | Montgomery |
| 2002/0069883 A1 | 6/2002 | Hirchenbain |
| 2003/0105450 A1 | 6/2003 | Dimick |
| 2003/0195588 A1 | 10/2003 | Fischell et al. |
| 2003/0220536 A1 | 11/2003 | Hissong |
| 2003/0220585 A1 | 11/2003 | Hissong |
| 2004/0097839 A1 | 5/2004 | Epley |
| 2004/0163882 A1 | 8/2004 | Fleming et al. |
| 2004/0225178 A1 | 11/2004 | Kriewall |
| 2005/0065585 A1 | 3/2005 | Salas |
| 2005/0165460 A1 | 7/2005 | Erfan |
| 2005/0209516 A1 | 9/2005 | Fraden |
| 2005/0267388 A1 | 12/2005 | Hanna |
| 2006/0100681 A1 | 5/2006 | Salas Carpizo |
| 2006/0197412 A1 | 9/2006 | Rasmussen |
| 2006/0253087 A1 | 11/2006 | Vlodaver et al. |
| 2006/0272650 A1 | 12/2006 | Hoogenakker et al. |
| 2007/0040454 A1 | 2/2007 | Freudenberger et al. |
| 2007/0112279 A1 | 5/2007 | Iseberg et al. |
| 2007/0250119 A1 | 10/2007 | Tyler et al. |
| 2007/0299362 A1 | 12/2007 | Epley et al. |
| 2008/0011308 A1 | 1/2008 | Fleming |
| 2008/0154183 A1 | 6/2008 | Baker et al. |
| 2008/0168775 A1 | 7/2008 | Windheim et al. |
| 2008/0208100 A1 | 8/2008 | Wolff |
| 2008/0212787 A1 | 9/2008 | Goldstein et al. |
| 2008/0220092 A1 | 9/2008 | Dipierro |
| 2008/0240942 A1 | 10/2008 | Heinrich et al. |
| 2008/0249439 A1 | 10/2008 | Tracey et al. |
| 2008/0264464 A1 | 10/2008 | Lee et al. |
| 2009/0012420 A1 | 1/2009 | Keller |
| 2009/0082831 A1 | 3/2009 | Paul et al. |
| 2009/0173353 A1 | 7/2009 | Pursell et al. |
| 2009/0182399 A1 | 7/2009 | Sylvestre |
| 2009/0228103 A1 | 9/2009 | Clayton |
| 2009/0293886 A1 | 12/2009 | Dedrick et al. |
| 2010/0002897 A1 | 1/2010 | Keady |
| 2010/0030131 A1 | 2/2010 | Morris et al. |
| 2010/0071707 A1 | 3/2010 | Wohl |
| 2010/0071708 A1 | 3/2010 | Lenhardt |
| 2010/0113991 A1 | 5/2010 | Wu |
| 2010/0179490 A1 | 7/2010 | Connelly et al. |
| 2010/0198282 A1 | 8/2010 | Rogers |
| 2010/0211142 A1 | 8/2010 | Rogers |
| 2010/0322454 A1 | 12/2010 | Ambrose et al. |
| 2011/0079227 A1 | 4/2011 | Turcot et al. |
| 2011/0097141 A1 | 4/2011 | Browm |
| 2011/0098551 A1 | 4/2011 | Zhang |
| 2011/0130786 A1 | 6/2011 | Clayton et al. |
| 2011/0172739 A1 | 7/2011 | Mann et al. |
| 2011/0184341 A1 | 7/2011 | Baker et al. |
| 2011/0224493 A1 | 9/2011 | Oyadiran et al. |
| 2011/0245902 A1 | 10/2011 | Katz |
| 2011/0301572 A1 | 12/2011 | Vlodaver et al. |
| 2012/0046607 A1 | 2/2012 | Syk |
| 2012/0203309 A1 | 8/2012 | Englehart |
| 2012/0265093 A1 | 10/2012 | Allen et al. |
| 2012/0296268 A1 | 11/2012 | Vlodavaer et al. |
| 2012/0302859 A1 | 11/2012 | Keefe |
| 2012/0310077 A1 | 12/2012 | Rogers |
| 2012/0310313 A1 | 12/2012 | Rogers et al. |
| 2012/0318605 A1 | 12/2012 | Brown |
| 2013/0123889 A1 | 5/2013 | Katz et al. |
| 2013/0136285 A1 | 5/2013 | Naumann |
| 2013/0152949 A1 | 6/2013 | Simon |
| 2013/0177179 A1 | 7/2013 | Ambrose et al. |
| 2013/0183173 A1 | 7/2013 | Kohli et al. |
| 2013/0282070 A1 | 10/2013 | Cowan et al. |
| 2013/0303953 A1 | 11/2013 | Lattner |
| 2013/0304103 A1 | 11/2013 | Burres |
| 2013/0310907 A1 | 11/2013 | Rogers et al. |
| 2013/0324932 A1 | 12/2013 | Cogley |
| 2013/0331823 A1 | 12/2013 | Askem et al. |
| 2014/0069442 A1 | 3/2014 | Lewis et al. |
| 2014/0088671 A1 | 3/2014 | Rogers et al. |
| 2014/0243941 A1 | 8/2014 | Rogers et al. |
| 2014/0249608 A1 | 9/2014 | Rogers |
| 2014/0275827 A1 | 9/2014 | Gill et al. |
| 2014/0309718 A1 | 10/2014 | Smith et al. |
| 2014/0334652 A1 | 11/2014 | Gebert |
| 2014/0344740 A1 | 11/2014 | Kaula et al. |
| 2015/0003644 A1* | 1/2015 | George ................ A61H 9/0071 |
| | | 381/165 |
| 2015/0005661 A1 | 1/2015 | Trammell |
| 2015/0141879 A1 | 5/2015 | Harper et al. |
| 2015/0230989 A1* | 8/2015 | George ................ A61M 13/003 |
| | | 128/868 |
| 2015/0320591 A1 | 11/2015 | Smith et al. |
| 2015/0320592 A1 | 11/2015 | Black et al. |
| 2015/0324544 A1 | 11/2015 | Maslowski et al. |
| 2015/0335466 A1 | 11/2015 | Schöggler |
| 2015/0374538 A1 | 12/2015 | Rogers |
| 2016/0067099 A1 | 3/2016 | Hayashi |
| 2016/0128897 A1 | 5/2016 | George et al. |
| 2016/0151206 A1 | 6/2016 | George et al. |
| 2016/0166203 A1 | 6/2016 | Goldstein |
| 2016/0279435 A1 | 9/2016 | Hyde et al. |
| 2016/0346117 A1 | 12/2016 | Rogers et al. |
| 2016/0378945 A1 | 12/2016 | Mian et al. |
| 2017/0105876 A1 | 4/2017 | O'Connell, Sr. et al. |
| 2017/0109988 A1 | 4/2017 | O'Connell, Sr. et al. |
| 2017/0135854 A1 | 5/2017 | Rogers et al. |
| 2017/0235889 A1 | 8/2017 | Main et al. |
| 2018/0008457 A1 | 1/2018 | Smith et al. |
| 2018/0106244 A1 | 4/2018 | Wang et al. |
| 2018/0125748 A1 | 5/2018 | Goldenberg et al. |
| 2020/0121544 A1 | 4/2020 | George et al. |
| 2020/0222272 A1 | 7/2020 | George et al. |
| 2021/0222684 A1 | 7/2021 | George et al. |
| 2021/0228414 A1 | 7/2021 | George et al. |
| 2022/0202617 A1 | 6/2022 | George et al. |
| 2022/0226158 A1 | 7/2022 | George et al. |

FOREIGN PATENT DOCUMENTS

| | | |
|---|---|---|
| CA | 1241152 | 8/1988 |
| CA | 2003452 | 6/1990 |
| CA | 2275057 | 10/1999 |
| CA | 2 337 076 | 1/2000 |
| CA | 2429560 | 1/2004 |
| CN | 2075517 U | 4/1991 |
| CN | 2418864 | 2/2001 |
| CN | 1308513 A | 8/2001 |
| CN | 2530645 | 1/2003 |
| CN | 2721057 Y | 8/2005 |
| CN | 1791370 A | 6/2006 |
| CN | 2912525 | 6/2007 |
| CN | 200945215 Y | 9/2007 |
| CN | 201143258 | 11/2008 |
| CN | 201164541 | 12/2008 |
| CN | 101668497 | 3/2010 |
| CN | 201505220 U | 6/2010 |
| CN | 201524178 | 7/2010 |
| CN | 201558360 | 8/2010 |
| CN | 201870809 | 6/2011 |
| CN | 202036187 | 11/2011 |
| CN | 202185057 | 4/2012 |
| CN | 102484761 | 5/2012 |
| CN | 102551957 | 7/2012 |
| CN | 202313927 | 7/2012 |
| CN | 102647966 | 8/2012 |
| CN | 202477966 | 10/2012 |
| CN | 202505833 | 10/2012 |

(56) References Cited

FOREIGN PATENT DOCUMENTS

| | | |
|---|---|---|
| CN | 102892392 A | 1/2013 |
| CN | 102986250 | 3/2013 |
| DE | 102011008802 | 7/2012 |
| EP | 0 026 247 | 4/1981 |
| EP | 0 400 900 | 12/1990 |
| EP | 1 027 863 | 8/2000 |
| EP | 2 207 366 | 7/2010 |
| EP | 2 990 017 | 3/2016 |
| FR | 2 605 516 A1 | 4/1988 |
| GB | 1432572 | 4/1976 |
| GB | 1522031 | 8/1978 |
| GB | 2054387 | 2/1981 |
| GB | 2185688 | 7/1987 |
| GB | 2343263 | 5/2000 |
| GB | 2479891 | 11/2011 |
| IT | 1214840 | 1/1990 |
| JP | S 57-188245 | 11/1982 |
| JP | H 02-220650 | 9/1990 |
| JP | H 07-111987 | 5/1995 |
| JP | H 11-514898 | 12/1999 |
| JP | 2002-519150 | 7/2002 |
| JP | 2003-018359 | 1/2003 |
| JP | 2006-345903 | 12/2006 |
| JP | 2009-022699 | 2/2009 |
| JP | 2010-233643 | 10/2010 |
| JP | 2010-535542 | 11/2010 |
| JP | 2011-217986 | 11/2011 |
| JP | 2012-526498 | 10/2012 |
| JP | 2013-068448 | 4/2013 |
| JP | 2013-102784 | 5/2013 |
| JP | 2020-44371 | 3/2020 |
| KR | 10-1273296 | 6/2013 |
| MX | PA03005598 | 10/2004 |
| MX | 2010014470 | 2/2011 |
| MX | 2011006854 | 8/2011 |
| MX | 2012007726 | 8/2012 |
| RU | 90 333 U1 | 1/2010 |
| WO | WO 1986/01399 | 3/1986 |
| WO | WO 1994/22372 | 10/1994 |
| WO | WO 1996/23293 | 8/1996 |
| WO | WO 1997/23178 | 7/1997 |
| WO | WO 2000/001331 | 1/2000 |
| WO | WO 2000/001346 | 1/2000 |
| WO | WO 2000/010484 | 3/2000 |
| WO | WO 2000/010627 | 3/2000 |
| WO | WO 2000/010848 | 3/2000 |
| WO | WO 2003/075761 | 9/2003 |
| WO | WO 2004/064672 | 8/2004 |
| WO | WO 2004/100844 | 11/2004 |
| WO | WO 2006/003910 | 1/2006 |
| WO | WO 2006/009545 | 1/2006 |
| WO | WO 2007/084674 | 7/2007 |
| WO | WO 2007/118092 | 10/2007 |
| WO | WO 2007/145853 | 12/2007 |
| WO | WO 2008/036368 | 3/2008 |
| WO | WO 2008/064230 | 5/2008 |
| WO | WO 2008/086187 | 7/2008 |
| WO | WO 2008/128173 | 10/2008 |
| WO | WO 2008/153588 | 12/2008 |
| WO | WO 2009/020862 | 2/2009 |
| WO | WO 2009/050306 | 4/2009 |
| WO | WO 2009/077902 | 6/2009 |
| WO | WO 2010/005899 | 1/2010 |
| WO | WO 2010/016925 | 2/2010 |
| WO | WO 2010/085196 | 7/2010 |
| WO | WO 2011/075573 | 6/2011 |
| WO | WO 2011/075574 | 6/2011 |
| WO | WO 2012/007193 | 1/2012 |
| WO | WO 2012/083098 | 6/2012 |
| WO | WO 2012/083102 | 6/2012 |
| WO | WO 2012/083106 | 6/2012 |
| WO | WO 2012/083126 | 6/2012 |
| WO | WO 2012/083151 | 6/2012 |
| WO | WO 2013/075255 | 5/2013 |
| WO | WO 2014/120947 | 8/2014 |
| WO | WO 2014/175257 | 10/2014 |
| WO | WO 2014/210457 | 12/2014 |
| WO | WO 2015/009421 | 1/2015 |
| WO | WO 2015/074060 | 5/2015 |
| WO | WO 2016/022761 | 2/2016 |
| WO | WO 2017/040739 | 3/2017 |
| WO | WO 2017/040741 | 3/2017 |
| WO | WO 2017/040747 | 3/2017 |
| WO | WO 2017/079783 | 5/2017 |
| WO | WO 2017/197150 | 11/2017 |
| WO | WO 2018/106839 | 6/2018 |
| WO | WO 2018/157143 | 8/2018 |
| WO | WO 2019/246456 | 12/2019 |

OTHER PUBLICATIONS

Baguley et al. Does caloric vestibular stimulation modulate tinnitus? Neuroscience Letters, Mar. 2011, 492(1), pp. 52-54.

Baier, et al.: "Vestibular-Evoked Myogenic Potentials In "Vestibular Migraine" and Meniere's Disease," Ann. N.Y. Acad. Sci., May 2009, 1164, pp. 324-327.

Becker: Weather and migraine: Can so many patients be wrong? Cephalalgia, Mar. 2011, 31(4), pp. 387-390.

Berthold Langguth, Verena Hund, Volker Busch, et al., "Tinnitus and Headache," BioMed Research International, vol. 2015, Article ID 797416, 7 pages, 2015. https://doi.org/10.115/2015/797416 (Year: 2015) in 7 pages.

Bolay et al.,: "Does Low Atmospheric Pressure Independently Trigger Migraine?" Headache, Oct. 2011, 51(9), pp. 1426-1430.

Breathometer. Breathometer—The World's First Smartphone Breathalyzer. Website, http://www.breathometer.co, original downloaded Jun. 19, 2014, 8 total pages.

Cadwell. Sierra Wave. Website, http://www.cadwell.com, originally downloaded Feb. 27, 2014, 1 page.

Cathcart, et al., "Pain sensitivity mediates the relationship between stress and headache intensity in chronic tension-type headache", Nov. 2012 (Year: 2012) in 5 pages.

Cranial Nerves—Wikipedia, https://en.wikipedia.org/alk1/Cranial_nerves, printed Aug. 16, 2019 in 12 pages.

Croley, Christen, "Mechanicsburg doctor develops new migraine therapy," The Sentinel, Nov. 9, 2012.

DaSilva, et al.: "tDCS-Induced Analgesia and Electrical Fields in Pain-Related Neural Networks in Chronic Migraine," The Journal of Head and Face Pain, Sep. 2012, 52, pp. 1283-1295.

Dirckx et al. Human tympanic membrane deformation under static pressure. Hearing Research, Jan. 1991, 51(1), pp. 93-106.

Doherty, Colleen. "The Link Between Migraines and Tinnitus". Verywell Health, Nov. 23, 2019, https://www.verywellhealth.com/link-between-migraines-and-tinnitus-4077631#citation-10 (Year: 2019) in 4 pages.

Facebook. Zōk: The first migraine and headache solution, Webpage, https://www.facebook.com, originally downloaded May 18, 2017, 10 pages total.

Fasold et al. Human Vestibular Cortex as Identified with Caloric Stimulation in Functional Magnetic Resonance Imaging. Neuroimage, Nov. 2002, 17(3), pp. 1384-1393.

FERROTEC. Thermal Solutions. Website: http://thermal.ferrotec.com, originally downloaded Feb. 27, 2014, 1 page.

FERROTEC. Thermoelectric Technical Reference—Installation of Thermoelectric Modules. Website, http://thermal.ferrotec.com, originally downloaded May 21, 2014, 4 total pages.

FERROTEC. Thermoelectric Technical Reference—Introduction to Thermoelectric Cooling. Website, http://forrotec.com, originally downloaded Feb. 27, 2014, 2 total pages.

Frangos E, Ellrich J, Komisaruk B. Non-invasive access to the vagus nerve central projections via electrical stimulation of the external ear: fMRI evidence in humans. Brain Stimul. Dec. 6, 2014. 8(3), 624-636 in 13 pages.

George et al. Safety and usability factors in development of a novel, automated treatment device for acute migraine. Biomedical sciences instrumentation. Biomedical sciences instrumentation, Jan. 2017, 53, pp. 398-403.

(56) References Cited

OTHER PUBLICATIONS

Hahn: "Let Me Blow in Your Ear, for Migraine Treatment, Of Course," Smile Columbia Dentistry, https://www.tmjtreatmentse.com, originally downloaded Apr. 25, 2016, 2 pages total.
Hu et al. Burden of migraine in the United States: disability and economic costs. Arch. Intern. Med., Apr. 1999, 159, pp. 813-818.
Janetta Neurovascular Compress in Cranial Nerve and Systemic Disease. Ann Surg, Oct. 1980, 192 (4), pp. 518-524.
Job et al. Cortical Representation of Tympanic Membrane Movements due to Pressure Variation: An ±MRI Study Human Brain Mapping, May 2011, 32(5), pp. 744-749.
Kanzara T, Hall A, Virk J, Leung B, Singh A. Clinical anatomy of the tympanic nerve: A review. World J Otorhinolaryngol. Nov. 2014; 4(4), 17-22 in 8 pages.
Kickstarter. Zōk: The first headache product that solves migraines and headaches. Website, https://www.funded.today, originally downloaded May 18, 2017, 3 pages total.
Kiyokawa J., Yamaguchi K, Okada R, Maehara T, Akita K. Origin, course and distribution of the nerves to the posterosuperior wall of the external acoustic meatus. Anat Sci Int. Mar. 2014; 89(4), 238-245.
Klingner et al.: "Components of vestibular cortical function," Behavioral Brain Research, Jan. 2013, 236(1), pp. 194-199.
Kolev. How caloric vestibular irrigation influences migraine attacks. Cephalalgia. Aug. 1990, vol. 10 issue 4, pp. 167-169 (abstract only).
Lifting the Burden. The Global Campaign Against Headache. Website, http://www.l-t-b.org, originally downloaded Feb. 27, 2014, 1 page.
Liszewski: Ear Pressure Equalizer. Website, http://www.ohgizmo.com, originally downloaded Dec. 18, 2013, 1 page.
Long Island news12.com. Long Island Naturally: Migraines. Website video, http://longisland.news12.com/multimedia/long-island-naturally-migraines-1.6501113, Nov. 26, 2013, 3 total pages.
Mayr: The Origins of Feedback Control. M.I.T. Press, 1970.
McGeoch et al. Vestibular stimulation can relieve central pain of spinal origin. Spinal Cord, Nov. 2008, 46(11), pp. 756-757.
Medscape. Peripheral Nerve Stimulator—Train of Four Monitoring. Website, http://emedicine.medscape.com, originally downloaded Feb. 27, 2014, 2 total pages.
Medtronic. Meniett Device for Meniere's Disease. Meniett Low-Pressure Pulse Generator device. Website, http://www.medtronic.com, originally downloaded Feb. 27, 2014, 2 total pages.
Medtronic. Restore Life's Balance with Meniett Therapy. The Meniett Device for Meniere's Disease. On-line article, http://www.medtronic.com, originally downloaded Mar. 13, 2015, 2 total pages.
Meng et al. Migraine Prevention with a Supraorbital Transcutaneous Stimulator: A Randomized Controlled Trial. Neurology, Sep. 2013, 81, pp. 1102-1103.
Minen. Tinnitus and Headache. American Migraine Foundation, website, downloaded Feb. 8, 2017, 3 pages total.
Mosqueria et al. Vagus Nerve Stimulation in Patients with Migraine. Rev Neurol, 2013, 57(2), English Abstract.
Nagai et al. Encapsulated nerve corpuscles in the human tympanic membrane. Archives of Otorhinolaryngology, 1989, 246(3), pp. 169-172.
New York Health Soultions. Migraine Headaches. Website, http://www.nyhealthsolutions.com, originally downloaded May 23, 2014, 2 pages.
Nihashi et al. Representation of the ear in human primary somatosensory cortex. Neuroimage, Feb. 2001, 13(2), pp. 295-304 (abstract only).
Olesen et al. Emerging Migraine treatments and drug targets. Trends in Pharmacological Sciences, 2011, 32(6), pp. 352-359.
Pederson et al. Neurostimulation in cluster headache: A review of current progress. Cephalalgia, 2013, 33(14), pp. 1179-1193.
Pietrobon, Migraine: new molecular mechanism. Neuroscientist. Aug. 2005, vol. 11, Issue 4, pp. 373-386 (abstract only).
Porta-Etessam et al. Neuro-otological symptoms in patients with migraine. Neurologia, Mar. 2011, 26(2), pp. 100-104.
Ramachandran et al. Rapid Relief of Thalamic Pain Syndrome Induced by Vestibular Caloric Stimulation. Neurocase, Jun. 2007, 13(3), pp. 185-188.
Sakata et al. Air pressure-sensing ability of the middle ear—Investigation of sensing regions and appropriate measurement conditions. Auris Nasus Larynx, Aug. 2009, 36(4), pp. 393-399.
Sameiro-Barbosa et al. Sensory Entrainment Mechanisms in Auditory Perception: Neural Synchronization Cortico-Striatal Activation. Frontiers in Neuroscience, Aug. 2016, vol. 10, Article 361, 8 pages.
Saunders R, Tympanic membrane sensation. Brain. 1985, 108, 378-404 in 18 pages.
Schoenen et al. Migraine prevention with a supraorbital transcutaneous stimulator. Neurology, 2013, 80(8), pp. 697-704.
Schulman. Breath-Holding, Head Pressure, and Hot Water: An Effective Treatment for Migraine Headache. Headache, Nov.-Dec. 2002, 42(10), pp. 1048-1050.
Scion Neurostim. Therapeutic Neuromodulation via Caloric Vestibular Stimulation. Thermoneuromodulation (TNM). Slides for presentation, dated Sep. 2015, 12 pages total.
Sheftell, F, Steiner, TJ, Thhomas, H. Harry Potter and the Curse of Headache. Headache: The Journal of Head and Face Pain. Jun. 2007, vol. 47, Issue 6, pp. 911-916 (abstract only) in 1 page.
Shevel, "Headaches and tinnitus: correlation found", May 2008 (Year: 2006).
Silberstein et al.: "Botulinum Toxin Type A as a Migraine Preventive Treatment," The Journal of Head and Face Pain, Jun. 2000, 40, pp. 445-450.
Smartproducts. Series 100—Cartridge Specialty Check Valves and Pressure Relief Valves. Online catalog, www.smartproducts,com, originally downloaded Mar. 28, 2014, 2 total.
Stender, DR., "Easing Migraine Symptoms with a Simple Puff of Air into the Ear," Pasadena Pain Management, http://www.pasadenapainmanagement.com, downloaded Apr. 25, 2016, 5 pages total.
Stovnver, LJ, et al. The global burden of headache: a documentation of headache prevalence and disability worldwide. Cephalalgia, 2007. vol. 27, pp. 193-210.
Sullivan: "Ear Insufflation As A Novel Therapy Which Produces Rapid Relief Of Migraine Headache—a Case Study," Funct Neurol Rehabil Egon 2013; vol. 3, Issue 1, pp. 93-107. Published on Jun. 7, 2013. Revised Jan. 28, 2013. Accepted Feb. 15, 2013.
Sullivan: "Ear Insufflation Produces Rapid and Significant Relief of Trigeminal Neuralgia," Funct Neurol Rehabil Egon 2013; vol. 3, Issue 4, pp. 1-6. Published on May 26, 2014. Revised Dec. 24, 2013. Accepted Jan. 12, 2014.
Tekdemir I, Aslan A, Elhan A., A clinico-anatomic study of the auricular branch of the vagus nerve and Arnold's ear-cough reflex. Surg Raiol Anat. 1998. 20(4), 253-257 in 5 pages.
Tekdemir I, Aslan A, Tuccar E, He C, Elhan A, Deda H. An anatomical study of the tympanic branch of the glossopharyngeal nerve (nerve of Jacobson). Ann Anat. Aug. 1998; 180(4): 349-52 in 4 pages.
Transcript of News Story, Aug. 22, 2013, video available at: https://www.facebook.com/178787878873891/videos/10201196245541704/.
"New Migraine Therapy," Aug. 22, 2013, video available at https://www.facebook.com/178787878873891/videos/10201196245541704/.
Transcript of News Story, Nov. 13, 2013, video available at: https://www.facebook.com/178787878873891/videos/treatment-for-migraines-and-trigeminal-neuralgia/10201781732138503/.
"Revolutionary Pain Therapy," Nov. 13, 2013, video available at https://www.facebook.com/178787878873891/videos/treatment-for-migraines-and-trigeminal-neuralgia/10201781732138503/.
Transcript of News Story, Jul. 7, 2014, video available at: https://www.facebook.com/178787878873891/videos/681870651898942/.
"New Therapy for Migraines," Jul. 7, 2014, video available at https://www.facebook.com/178787878873891/videos/treatment-for-migraines-and-trigeminal-neuralgia/10201781732138503/.
Transcript of Webinar, Apr. 10, 2013, video available at: https://www.anymeeting.com/WebConference/RecordingDefault.aspx?c_psrid=ED57DC868548.

(56) References Cited

OTHER PUBLICATIONS

"A novel application to resolve migraine headaches—A Functional Neurology forum," Apr. 10, 2013, video available at: https://www.anymeeting.com/WebConference/RecordingDefault.aspx?c_psrid=ED57DC868548.

Ultimate Ears. Ultimate Ears Custom In-Ear Monitors. Website, http://pro.ultimatears.com, originally downloaded Feb. 27, 2014, 3 total pages.

Von Korff, et al., "Assessing headaches severity. New Directions", Jul. 1994 (Year: 1994).

Westone. Occupational Earpieces. Website, http://www.westone.com, originally downloaded Feb. 27, 2014, 2 total pages.

Widemar L, Hellstrom S, Schultzberg M, Stenfors LE. Autonomic innervation of the tympanic membrane. An immunocytochemical and histofluorescence study. Acta Otolaryngol. Jul.-Aug. 1985;100(1-2):58:65 in 9 pages.

Wikipedia. Microcurrent electrical neuromuscular stimulator. Website, http://en.wikipedia.org, originally downloaded Feb. 27, 2014, 3 total pages.

Wikipedia. Somatosensory evoked potential. Website, http://en.wikipedia.org, originally downloaded Feb. 27, 2014, 5 pages total.

Wikipedia. Transcutaneous electrical nerve stimulation. Website, http://en.wikipedia.org, originally downloaded Feb. 27, 2014, 5 pages total.

World Health Organization. Headache disorders. Website, http://www.who.int, originally downloaded Feb. 27, 2014, 4 total pages.

International Preliminary Report on Patentability in Application No. PCT/US2019/038331, issued Dec. 22, 2020 in 12 pages.

International Search Report and Written Opinion in International Application No. PCT/US2019/038331, mailed Nov. 19, 2019 in 17 pages.

Teixido, Michael: "Migraine—More than a Headache," Dec. 15, 1999, ENT and Allergy of Delaware (Year: 1999).

* cited by examiner

SYSTEMS AND METHODS FOR TREATING NEUROLOGICAL DISORDERS

CROSS-REFERENCE TO RELATED APPLICATIONS

This application is a continuation of International Patent Application No. PCT/2019/038331, filed Jun. 20, 2019, and titled SYSTEMS AND METHODS FOR TREATING NEUROLOGICAL DISORDERS, which claims the benefit under 35 U.S.C. § 119(e) of U.S. Provisional Patent Application No. 62/688,984, filed Jun. 22, 2018, and titled SYSTEMS AND METHODS FOR TREATING NEUROLOGICAL DISORDERS, the entirety of each of which is hereby incorporated by reference herein and made part of this specification for all that it discloses.

INCORPORATION BY REFERENCE

International Patent Application No. PCT/US2017/064964, filed on Dec. 6, 2017, and published as WO 2018/106839 on Jun. 14, 2018, is hereby incorporated by reference herein in its entirety, forming part of the present disclosure. Each of the following patent matters is hereby incorporated by reference herein in its entirety: U.S. Provisional Patent Application No. 61/841,111, filed Jun. 28, 2013; U.S. Provisional Patent Application No. 61/863,317, filed Aug. 7, 2013; U.S. Provisional Patent Application No. 61/983,865, filed Apr. 24, 2014; U.S. Patent Application Publication No. 2015/0000678, published Jan. 1, 2015; International Patent Application Publication No. WO 2015/009421, published Jan. 22, 2015; U.S. Pat. No. 9,039,639, issued May 26, 2015; U.S. Patent Application Publication No. 2018/0023558, published Jan. 25, 2018; and International Patent Application No. PCT/US2018/019981, filed Feb. 27, 2018. The foregoing patent matters are incorporated by reference for the additional embodiments and details disclosed, and are not for limiting the disclosure presented herein. By way of example, any feature, structure, material, method, or step that is described and/or illustrated in any embodiment in the foregoing patent matters can be used with or instead of any feature, structure, material, method, or step that is described and/or illustrated in the following paragraphs of this specification or the accompanying drawings. Although this disclosure makes several references to alternative embodiments and/or additional details in the '964 application (e.g., the '839 Publication), the other matters that are incorporated by reference also contain applicable features, alternative embodiments, and/or additional details.

BACKGROUND

This disclosure relates to treatment of medical conditions, including but not limited to systems and methods for treating neurological disorders. Neurological disorders can negatively affect quality of life, and indeed can be debilitating and cause numerous problems with relationships, employment, and so on. Some conditions, such as migraine headaches are sometimes treated with pharmaceuticals, which can have side effects. There remains a need for systems and methods for improving treatment of medical conditions.

SUMMARY

Certain example embodiments are summarized below for illustrative purposes. The embodiments are not limited to the specific implementations recited herein. Embodiments may include several novel features, no single one of which is solely responsible for its desirable attributes or which is essential to the embodiments.

There is a burgeoning field of understanding and applications within the neurosciences which seek to affect positive physiological changes in the nervous system through non-pharmaceutical and non-surgical applications. This field of 'functional neurology' views the human nervous system as a receptor driven system, which may be activated and stimulated in specific ways to produce adaptive, long-term changes through the process of neuroplasticity. This approach to neurorehabilitation utilizes, but not necessarily exclusively includes, various forms and patterns of receptor activation or deactivation to promote positive neurophysiological adaptations within the central nervous system, including the brain, brainstem, and spinal cord, which may promote physiological function of associated tissues, organs, and systems.

There would be a substantial advantage in providing a device or methods which can generate one or more stimuli which can alleviate one or more symptoms associated with a disorder, such as craniofacial pain syndromes or headache syndromes, or treat one or more disorders.

Particular embodiments of the subject matter described in this specification can be implemented so as to realize one or more of the following advantages. A treatment device is described that can treat neurological disorders, such as to safely eliminate, or reduce an intensity or frequency of, pain associated with headaches, which can include pain of the head or neck, and can optionally include pain not caused by underlying diseases or structural problems, such as primary headaches (e.g., migraines, cluster headaches, tension-type headaches, and so on). As will be described, the treatment device can manipulate pressure and/or temperature associated with one or more ears of a patient, such as manipulating pressure and/or temperature in an external ear canal of an ear (e.g., moving, heating, and/or cooling the tympanic membrane). The treatment device can utilize pressure and/or temperature profiles, for instance specific patterns of pressure and/or temperature applied to an ear (e.g., time series of pressure and/or temperature values), that are determined to reduce headache pain of individual users.

Aspects of this disclosure can relate to a treatment system that includes an earpiece; a fluid flow generator; a fluid conduit extending between the fluid flow generator and the earpiece; a temperature modifier; one or more valves having a caloric configuration and a pressure configuration; and a controller. The controller can be configured to operate the system in a caloric mode during a first period of time by positioning the one or more valves in the caloric configuration, operating the fluid flow generator to apply a flow of fluid through the fluid conduit and through the earpiece, and operating the temperature modifier to change a temperature of the fluid. The controller can operate the system in a pressure mode during a second period of time different than the first period of time by positioning the one or more valves in the pressure configuration, and operating the fluid flow generator to apply a pressure differential between an external ear canal pressure and ambient pressure.

The pressure differential can be effective to treat a neurological disorder. The pressure differential can be effective to treat neurological pain, headache pain, craniofacial pain, or one or more symptoms of a migraine. A user interface can be configured to receive input from a subject that the subject is experiencing one or more symptoms associated with a migraine (or other neurological disorder). The controller can be configured to operate the system in the caloric mode and the pressure mode in response to the input.

The temperature modifier can be a heating element, and the controller can be configured to operate the heating element to heat the fluid in caloric mode. The second period of time can be after the first period of time. Caloric mode can be before pressure mode, although the reverse order could be apply as well. The one or more valves can include an outlet valve. The system can include a second fluid conduit that can extend between the earpiece and the outlet valve. The outlet valve can have an open configuration that permits fluid to flow through the second fluid conduit and out to an ambient area. The outlet valve can have a closed configuration that impedes fluid from flowing through the second fluid conduit. The earpiece can have an outlet valve, and the outlet valve has an open configuration that permits fluid to flow through the earpiece and out to an ambient area. The outlet valve can have a closed configuration that impedes fluid from flowing through the earpiece and out to the ambient area. The outlet valve can be open in the caloric configuration and wherein the outlet valve can be closed in the pressure configuration. The system can have an outlet check valve configured to permit fluid to flow through the outlet valve to the ambient area and to impede fluid from flowing from the ambient area in through the outlet valve. The caloric configuration of the one or more valves can enable irrigation of the ear with a stream of fluid flowing to the ear and then out to an ambient area. The pressure configuration of the one or more valves can enables a flow of fluid to cause pressure to build up in the external ear canal.

The system can have a second earpiece and a second fluid conduit extending between the fluid flow generator and the second earpiece. The one or more valves can have a first configuration that directs fluid flow through the earpiece while impeding fluid flow through the second earpiece. The one or more valves can have a second configuration that directs fluid flow through the second earpiece while impeding fluid flow through the earpiece. The one or more valves can have a third configuration that directs fluid flow through both the earpiece and the second earpiece.

The earpiece can have the temperature modifier (e.g., heater). The fluid conduit can have the temperature modifier (e.g., heater). The temperature modifier can have conductive material incorporated into the fluid conduit. The conductive material can include a coil of resistive wire. The earpiece can be configured to engage the external ear canal to provide a barrier between the external ear canal pressure and ambient pressure. The fluid flow generator can have a diaphragm having a body portion that substantially conforms to a portion of a toroidal shape.

The system can have a temperature sensor configured to measure the temperature of the fluid. The system can have a pressure sensor. The controller can be configured to use information from the pressure sensor for feedback control to implement a pressure treatment profile.

Aspects of this disclosure can relate to a treatment system that includes an earpiece configured to engage an ear; a fluid flow generator; a fluid conduit extending between the fluid flow generator and the earpiece; a temperature modifier; and a controller. The controller can operate the temperature modifier to change a temperature of the ear during a first period of time. The controller can operate the fluid flow generator to apply a pressure differential between an external ear canal pressure and ambient pressure during a second period of time. The second period of time can be different than the first period of time. The temperature modifier can be a heater. The second time can be after the first time. The system can have one or more valves configured to transition between a caloric mode and a pressure mode.

Aspects of this disclosure can relate to a method for treating a disorder. The method can include changing a temperature of an external ear canal during a first period of time, and applying a pressure differential between the external ear canal and ambient pressure during a second period of time different from the first period of time.

Changing the temperature can include applying heat to the external ear canal. The second period of time can be after the first period of time. The disorder can include headache pain (e.g., or other neurological disorders). The disorder can include one or more symptoms associated with a migraine. The disorder can include a neurological disorder.

The method can include opening an outlet valve; operating a fluid flow generator to drive a flow of fluid through a fluid conduit, through an earpiece, into the external ear canal, and out the open outlet valve; and operating a temperature modifier to change a temperature of the flowing fluid to apply heating or cooling to the external ear canal. The earpiece can include the outlet valve. A second fluid conduit can extend between the earpiece and the outlet valve. An outlet check valve permits fluid to exit the outlet valve and impedes fluid from entering through the outlet valve.

The method can include closing the outlet valve and operating the fluid flow generator to produce a flow of fluid through the earpiece to create the pressure differential. Applying the heat can increase the sensitivity of mechanoreceptors associated with the external ear canal. Applying the pressure differential stimulates the mechanoreceptors to produce a stronger neurological response than would be produced without applying the heat. The method can include applying heat to the external ear canal during a third period of time after the second period of time, and applying a pressure differential between the external ear canal and ambient pressure during a fourth period of time after the third period of time. The method can include repeatedly transitioning between changing the temperature and applying the pressure differential.

The method can include applying heat to a second external ear canal of a second ear during a third period of time after the second period of time, and applying a pressure differential between the second external ear canal and ambient pressure during a fourth period of time after the third period of time. The method can include changing one or more valves from a right ear configuration to a left ear configuration or from the left ear configuration to the right ear configuration.

Some aspects of this disclosure can relate to a treatment system that can include an earpiece; a fluid flow generator; a fluid conduit extending between the fluid flow generator and the earpiece; an outlet valve; and a controller. The controller can be configured to operate the system in an irrigation mode by opening the outlet valve and operating the fluid flow generator to apply a flow of fluid through the fluid conduit, through the earpiece, and out the outlet valve to an ambient area. The controller can operate the system in a pressure mode by closing the outlet valve and operating the fluid flow generator to apply a pressure differential between an external ear canal pressure and ambient pressure.

The earpiece can include an outer surface configured to sealably engage the external ear canal sufficiently to provide a barrier between the external ear canal pressure and the ambient pressure. The system can be configured to transition between the irrigation mode and the pressure mode while the earpiece remains sealably engaged with the external ear canal. The system can include a temperature modifier. The controller can be configured to operate the temperature modifier to change a temperature of the fluid during irrigation mode. The controller can be configured to operate the system in pressure mode after operating the system in irrigation mode to heat the external ear canal.

The earpiece can include the outlet valve. A second fluid conduit can extend between the earpiece and the outlet valve. The system can include an outlet check valve configured to permit fluid to flow through the outlet valve to the ambient area and to impede fluid from flowing from the ambient area in through the outlet valve. The earpiece can include the temperature modifier. The temperature modifier can include a conductive material incorporated into the fluid conduit.

The system can have a second earpiece; a second fluid conduit extending between the fluid flow generator and the second earpiece; and one or more valves having a first configuration that directs fluid flow through the earpiece while impeding fluid flow through the second earpiece. The one or more valve can have a second configuration that directs fluid flow through the second earpiece while impeding fluid flow through the earpiece. The one or more valves can have a third configuration that directs fluid flow through both the earpiece and the second earpiece. The earpiece and the second earpiece can be fluidically coupled to the same outlet valve. The system can include a second outlet valve for venting fluid that flows through the second earpiece to the ambient area.

The fluid flow generator can include a diaphragm having a body portion that substantially conforms to a portion of a toroidal shape. The system can have a temperature sensor configured to measure the temperature of the fluid. The system can have a pressure sensor. The controller can be configured to use information from the pressure sensor for feedback control to implement a pressure treatment profile.

Aspects of this disclosure can relate to a method for treating a disorder. The method cam include inserting an earpiece into an ear of a subject; opening an outlet valve; and operating a fluid flow generator to drive fluid through a fluid conduit from the fluid flow generator, to the earpiece, into the ear, and through the open outlet valve to the ambient area.

Aspects of this disclosure can relate to a method for treating a disorder. The method can include inserting an earpiece into an ear of a subject to sealably engage an external ear canal sufficiently to provide a barrier between an external ear canal pressure and ambient pressure, and operating a fluid flow generator to drive fluid through a fluid conduit from the fluid flow generator, to the earpiece, into the ear, and out to the ambient area to provide fluid irrigation to the ear while the earpiece is sealably engaged with the external ear canal.

The method can include opening an outlet valve. The operating the fluid flow generator can drive the fluid out through the open outlet valve to the ambient area. The method can include closing the outlet valve and operating the fluid flow generator to produce a pressure differential between the external ear canal pressure and ambient pressure.

The method can include modifying a temperature of the fluid driven through the earpiece. The method can include heating the fluid driven through the earpiece to heat the external ear canal. The method can include applying a pressure differential between the external ear canal pressure and the ambient pressure after heating the external ear canal. The fluid conduit can have a conductive material for modifying the temperature of the fluid. The earpiece can have a temperature modifier configured to change the temperature of fluid that passes through the earpiece. The earpiece can have the outlet valve. A second fluid conduit can extend between the earpiece and the outlet valve.

Aspects of this disclosure can relate to a treatment system that includes an earpiece; a fluid flow generator; a first fluid conduit extending between the fluid flow generator and the earpiece; an outlet valve; a second fluid conduit extending between the earpiece and the outlet valve; and a controller. The controller can be configured to open the outlet valve and operating the fluid flow generator to apply a flow of fluid through the first fluid conduit, through the earpiece, to the ear, through the second fluid conduit, and out the outlet valve to an ambient area.

The controller can be configured to operate the system in a pressure mode by closing the outlet valve and operating the fluid flow generator to apply a pressure differential between an external ear canal pressure and ambient pressure. The system can include a heating element, and the controller can be configured to operate the heating element to heat the fluid that flows through the earpiece to heat the external ear canal. The controller can be configured to apply the pressure differential after heating the external ear canal.

Aspects of this disclosure can relate to a method for treating a disorder. The method can include inserting an earpiece into an ear of a subject; opening an outlet valve; and operating a fluid flow generator to drive fluid through a first fluid conduit, to the earpiece, into the ear, through a second fluid conduit, and through the open outlet valve to the ambient area.

The method can include modifying the temperature of the fluid driven through the earpiece. The method can include heating the fluid driven through the earpiece to heat the ear. The method can include closing the outlet valve and operating the fluid flow generator to produce a pressure differential between an external ear canal pressure and ambient pressure after heating the ear. The method can include closing the outlet valve and operating the fluid flow generator to produce a pressure differential between an external ear canal pressure and ambient pressure.

Aspects of this disclosure can relate to a treatment system that includes an earpiece; a fluid flow generator; and a fluid conduit extending between the fluid flow generator and the earpiece. Operation of the fluid flow generator can be configured to drive fluid through the fluid conduit, through the earpiece, and to the ear. The system can have a temperature modifier configured to change the temperature of the fluid. The temperature modifier can be positioned closer to the earpiece than to the fluid flow generator.

The system can have an outlet valve and a controller configured to open the outlet valve and operate the fluid flow generator to apply a flow of fluid through the fluid conduit, through the earpiece, to the ear, and out the outlet valve to an ambient area. The controller can be configured to close the outlet valve and operate the fluid flow generator to apply a pressure differential between an external ear canal pressure and an ambient pressure. The controller can be configured to operate the temperature modifier to heat the fluid during a first period of time, and apply the pressure differential during a second period of time after the first period of time. The earpiece can include the temperature modifier. The fluid conduit can include the temperature modifier. The temperature modifier can have conductive material incorporated into the fluid conduit.

For the various systems disclosed herein, the controller can include one or more computer processors and computer-readable memory storing instructions that are executable by the one or more computer processors.

Aspects of this disclosure can relate to a treatment system that includes a treatment device comprising a fluid flow generator; a valve module; an earpiece; a first fluid flow conduit fluidically coupling the fluid flow generator to the valve module; a second fluid flow conduit fluidically coupling the valve module to the earpiece; and a third fluid flow conduit fluidically coupling the earpiece to the valve module. The valve module can have an irrigation configuration that permits fluid to flow from the fluid flow generator, through the first fluid conduit, through the valve module, through the second fluid flow conduit, through the earpiece, through the third fluid flow conduit, and through the valve module. The valve module can have a pressure configuration in which the fluid flow generator applies pressure.

The valve module can include a valve that is open in the irrigation configuration and closed in the pressure configuration. The valve module can include an actuator configured to open and close the valve in response to electrical signals. The treatment system can have a temperature modifier configured to modify the temperature of fluid flowing through the second fluid flow conduit. The temperature modifier can include a heater. The valve module can include an outlet check valve configured to permit fluid to flow from the third fluid flow conduit through the valve module and out to the ambient environment when the valve module is in the irrigation configuration. The valve module can include an inlet check valve configured to permit fluid to flow from the ambient environment, into the valve module, and through the second fluid flow conduit when the valve module is in the irrigation configuration.

The treatment system can have an additional earpiece; a fourth fluid flow conduit fluidically coupling the valve module to the additional earpiece; and a fifth fluid flow conduit fluidically coupling the additional earpiece to the valve module. The valve module can have a first configuration that directs fluid flow to the earpiece while impeding fluid flow to the additional earpiece. The valve module can have a second configuration that directs fluid flow to the additional earpiece while impeding fluid flow to the earpiece. The valve module can have a third configuration that directs fluid flow to both the earpiece and the additional earpiece. The valve module can have an actuator configured to transition the valve module between the first configuration and the second configuration in response to electrical signals.

Aspects of this disclosure can relate to a treatment system having a treatment device comprising a fluid flow generator; a valve module; a first earpiece; a second earpiece; at least one outlet flow conduit fluidically coupling the fluid flow generator to the valve module; a first ear flow conduit fluidically coupling the valve module to the first earpiece; and a second ear flow conduit fluidically coupling the valve module to the second earpiece. The valve module can have a first configuration that directs fluid flow from the at least one outlet flow conduit to the first earpiece via the first ear flow conduit and while impeding fluid flow from the at least one outlet flow conduit to the second earpiece via the second ear flow conduit. The valve module can have a second configuration that directs fluid flow from the at least one outlet flow conduit to the second earpiece via the second ear flow conduit while impeding fluid flow from the at least one outlet flow conduit to the first earpiece via the first ear flow conduit.

The valve module can have a third configuration that directs fluid flow to the first earpiece and to the second earpiece. The valve module can have an actuator configured to transition the valve module between the first configuration and the second configuration in response to electrical signals. The fluid flow generator can have a diaphragm having a body portion that substantially conforms to a portion of a toroidal shape. The valve module can have a manual actuator. The valve module can have an actuator that is movable between a first position and a second position, and the actuator can have one or more structures that pinch closed the first ear flow conduit when the actuator is in the first position, and the one or more structures can pinch closed the second ear flow conduit when the actuator is in the second position. The actuator can be moveable to a third position, and the one or more structures do not pinch closed either of the first ear flow conduit and the second ear flow conduit when the actuator is in the third position. The actuator is rotatable between the positions. The actuator can include a visual indicator. A housing of the valve module can have an aperture, wherein the visual indicator can align with the aperture to provide an indication of the position of the actuator.

The various system disclosed herein can include eyewear having one or more green lenses. The earpiece can be coupled to the eyewear to position the earpiece to engage the ear of subject.

Aspects of this disclosure can relate to a treatment system comprising an earpiece; a fluid flow generator; a fluid conduit extending between the fluid flow generator and the earpiece; a controller configured to operate the fluid flow generator to produce a pressure differential between an external ear canal pressure and an ambient pressure; and eyewear having one or more green lenses.

The one or more lenses can have a maximum transmission of light at a wavelength between about 495 nm and about 570 nm. The eyewear can have side arms, and the earpiece can be coupled to one of the side arms.

Aspects of this disclosure can relate to a method that includes placing eyewear on a subject, where the eyewear can have one or more green lenses; and administering a neuromodulation stimulus while the subject is wearing the eyewear.

Aspects of this disclosure can relate to a method that includes placing eyewear on a subject, where the eyewear can have one or more green lenses; and configuring a neuromodulation system to be operable to provide a neuromodulation stimulus while the subject is wearing the eyewear.

Aspects of this disclosure can relate to a treatment system that can include a treatment device comprising a fluid flow generator that includes a diaphragm having a body portion that substantially conforms to a portion of a toroidal shape; and an earpiece fluidically coupled to the fluid flow generator.

Aspects of this disclosure can relate to a method of engaging an earpiece with an ear. The method can include inserting a canal portion of an earpiece into an external ear canal of an ear. The earpiece can have a concha portion that is positioned in a concha of the ear. The method can include moving the earpiece so that the concha portion moves downward and presses against a lower helix of the concha portion of the ear in a secured configuration for the earpiece, and applying at least one of a flow of fluid, a pressure differential relative to an ambient pressure outside the ear, and a temperature differential relative to body temperature of the patient or an ambient temperature outside the patient, via the canal portion and to the external ear canal in the secured configuration.

The details of one or more embodiments of the subject matter of this specification are set forth in the accompanying drawings and the description below. Other features, aspects, and advantages of the subject matter will become apparent from the description, the drawings, and from the claims.

BRIEF DESCRIPTION OF THE DRAWINGS

Certain embodiments will be discussed in detail with reference to the following figures, wherein like reference numerals refer to similar features throughout. These figures are provided for illustrative purposes and the embodiments are not limited to the specific implementations illustrated in the figures.

DETAILED DESCRIPTION OF CERTAIN EMBODIMENTS

Various systems, methods, and components can be used in different embodiments of the device. Some embodiments are illustrated in the accompanying figures; however, the figures are provided for convenience of illustration only, and should not be interpreted to limit the inventions to the particular combinations of features shown. Rather, any feature, structure, material, step, or component of any embodiment described and/or illustrated in this specification can be used by itself, or with or instead of any other feature, structure, material, step, or component of any other embodiment described and/or illustrated in this specification. Accordingly, none of the features disclosed in this specification are essential or indispensable.

Overview

Aspects of this disclosure relate to embodiments of systems and methods that can be used to treat medical conditions, such as neurological disorders and/or symptoms thereof (e.g., migraine headaches, other types of headaches, craniofacial pain, face pain, pain in other body portions, dizziness, nausea, seizures, etc.). A treatment system may be used to reduce or alleviate symptoms of one or more conditions or symptoms experienced by a user (e.g., pain). For instance, an example treatment device can be configured to provide a fluid flow to and/or apply pressure to an external ear canal of a patient. In some embodiments, a portion of the treatment device can be placed inside an ear cavity (e.g., the outer ear canal) of a user. All references to any type of treatment device (e.g., a pressure generator) in this application should be understood to include and disclose any type of fluid flow generator that accomplishes or facilitates storage or transfer of fluid to an ear of a user.

The present application includes a number of embodiments of treatment systems for medical conditions. Though one or more Figures may show a treatment system of a particular embodiment, it shall be understood that any features and/or methods of any treatment system disclosed herein can be used in and/or with any of treatments system disclosed herein. For example, any one of the embodiments of the treatment system disclosed in the present application can be provided or used in connection with any of the treatment systems described and/or contemplated within International Patent Application No. PCT/US2017/064964 published as WO 2018/106839 (herein referred to as the '839 Publication), which is incorporated by reference herein in its entirety.

Figure 1:
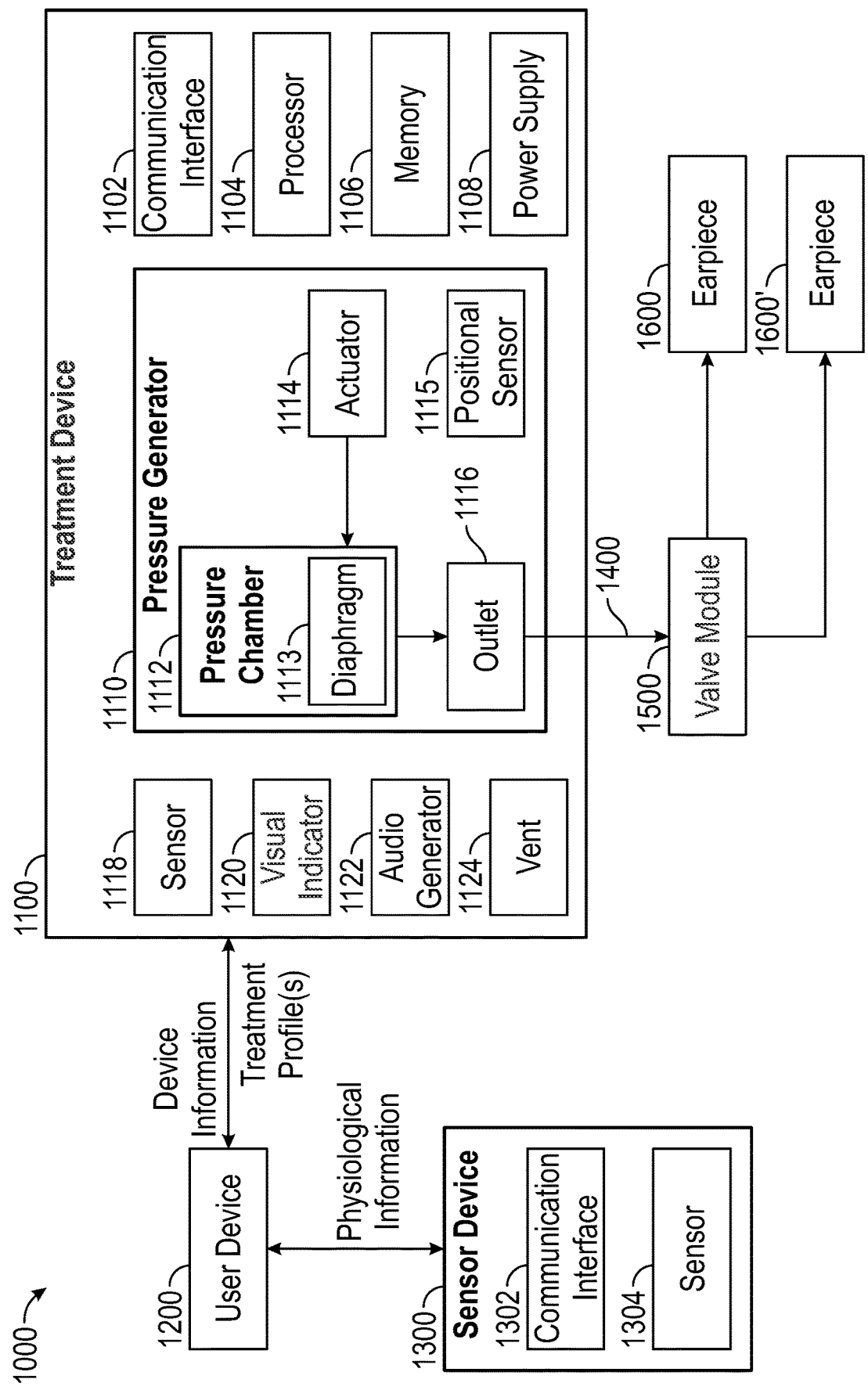
FIG. 1 illustrates a block diagram of an example treatment system having a treatment device in communication with other systems and devices.

FIG. 1 illustrates a schematic block diagram of an example embodiment of a treatment system 1000. In some embodiments, the treatment system 1000 can have any of the same or similar components, features, materials, sizes, configurations, and other details of any other pump system embodiments disclosed or incorporated by reference herein, including the embodiments of any of the treatments systems described in the '839 Publication. In some embodiments, the treatment system 1000 can be miniaturized and portable, although a larger conventional portable or non-portable pump can also be used.

As shown in the illustrated embodiment, the treatment system 1000 can include a treatment device 1100. The treatment device 1100 may be in communication with at least one of a user device 1200, valve module 1500, and one or more earpieces 1600, 1600'. The treatment device 1100 can include a communication interface 1102 for communicating with the user device 1020, for example. In some embodiments, the one or more earpieces 1600, 1600' and/or the valve module 1500 can be part of the treatment device 1100.

The user device 1200, in some embodiments, may be part of the treatment device 1100 (e.g., shared within the same housing). The user device 1200 can be in electrical communication (e.g., wired or wireless) with the treatment device 1100. The user device 1200 can be a mobile electronic device, such as a smartphone, tablet, mobile phone, or the like. In some embodiments the user device 1200 can be used for any suitable purpose for controlling an operation of the treatment system 1000. For example, the user device 1200 can be used to activate the treatment system 1000, to pause the treatment system 1000, receive user input (e.g., regarding symptoms), determine treatment profiles to apply, and/or be used for any other suitable purpose for controlling an operation of the treatment system 1000. The user device 1200 can include any type of user interface, such as a switch, button, touchpad, touch screen, keyboard, and so on.

As shown in the illustrated embodiment, the treatment device 1100 can also include a source of positive and/or negative pressure, such as the pressure generator 1110, and a sensor 1118. In some embodiments, the treatment device 1100 can include an outlet 1116 to connect to one or more of the tubing 1400, the valve module 1500, and the one or more earpieces 1600, 1600'. The treatment device 1100 can implement pressure profiles, as discussed for example in the '839 Publication.

In some embodiments, one or more indicators (e.g., a visual indicator 1120 and/or an audio generator 1122 as shown in FIG. 1) can indicate one or more operating and/or failure conditions of the treatment system 1000. In some embodiments, each of the one or more indicators can provide an indication regarding a different operating condition. For example, an active indicator can represent a transition between various operational modes, as discussed herein. In some embodiments, the treatment system 1000 can include visual, audible, tactile, and other types of indicators or alarms configured to signal to the user various operating conditions. The indicators can include speakers, displays, light sources, etc., and/or combinations thereof.

Movement of the user, treatment device, earpieces, etc. may cause pressure and/or temperature variations, and in some embodiments, the treatment device can control the pressure and/or temperature to compensate for those variations. As disclosed elsewhere herein and/or in the '839 Publication and other documents incorporated by reference, the system can have a pressure sensor, which can measure a pressure differential between the external ear canal and ambient pressure. The pressure sensor can be in the earpiece or in the treatment device or in the valve module, or at any other suitable location. The pressure sensor can measure the pressure in the fluid conduit coupled to the earpiece 1600 or 1600', which can be the same as or indicative of the pressure in the external ear canal. The system can implement one or more pressure treatment profiles, which can be one or more predetermined pressures applied for one or more predetermined times. Various different pressure profiles can be used, such as positive pressure profiles, negative pressure profiles, pressure profiles that transition between positive pressure and negative pressure, pressure profiles that sustain a generally constant pressure for a time, pressure profiles that continuously vary the pressure, pressure profiles that oscillate the pressure about a baseline pressure that is different from ambient, etc. The system can use the measured pressure to provide feedback control for implementing the pressure profiles. The memory 1106 can include one or more pressure profiles (e.g., processor-executable instructions) and the processor 1104 can operate the system to implement the pressure profiles. Additional details regarding the pressure profiles is provided in the '839 Publication.

The treatment device, in some instances as described herein, may be configured to selectively apply treatment to one or both ears at the same or different times during a treatment session, without the user needing to reposition the earpiece. As shown in FIG. 1, the treatment device 1100 can have a first earpiece 1600 and a second earpiece 1600'. In some embodiments, the device 1100 may include one or more valve modules 1500. The valve module 1500 may be configured to selectively establish fluid communication between the treatment device 1100 and the one or more earpieces 1600, 1600', as described herein and in the '839 Publication.

Unless otherwise noted, reference numerals in the Figures herein may refer to components that are the same as or generally similar to the components discussed in the '839 Publication. Any one of the treatment systems disclosed herein or in the '839 Publication can be modified to include any one of the features of treatment device 1000. For example, any treatment device disclosed herein can include a pressure generator 1110, a valve module 1500, any/or any additional features, as shown and described with reference to FIG. 1. It will also be understood that any feature, structure, material, step, or component of any embodiment described and/or illustrated herein can be used with or instead of any other feature, structure, material, step or component of any embodiment of the treatment system 1000 of FIG. 1 or of any embodiment of the treatment system of the '839 Publication.

Caloric Treatment System Examples

Overview

Systems and methods can be configured to heat and/or cool the ear. In some embodiments, applying heat to the ear can increase the intensity of neurological signals produced by using the treatment device 1100. For example, heating the tympanic membrane can cause mechanoreceptors associated with the tympanic membrane to produce more neurological signals and/or signals having higher strength when the tympanic membrane is manipulated (e.g., by pressure in the external ear canal). In some cases, the systems and methods can be used for caloric vestibular stimulation, above and/or below body temperature. In some instances, caloric vestibular stimulation systems can include and/or be combined with a treatment system configured to regulate pressure by including a fluid temperature regulator fluidically coupled between a treatment device and one or more earpieces. The fluid temperature regulator can be operable, for example, to regulate a fluid temperature of fluid flowing through the one or more earpieces.

A pressure-regulating treatment system configured to provide positive and/or negative pressure within a user's ear canal can provide therapeutic effects for various neurological disorders (e.g., migraines), as described in detail within the '839 Publication. The treatment system can provide an application of neuromodulation that may be a form of cranial nerve stimulation. In some embodiments, a pressure-regulating treatment system applies simultaneous barometric pressure changes and reversible, mechanical, tissue deformation to the tissues of the external, middle, and/or inner ear. The treatment system may be configured to advantageously apply treatment in a comfortable and non-invasive manner. For example, as described in the '839 Publication, the tensor tympani and stapedius muscles are associated with regulation of sound transmission through the middle ear by altering resting tension in the tympanic member and the ossicular chain, respectively. These middle ear muscles can also be proprioceptors that are sensitive to tension (e.g., stretch via pushing and/or pulling of the muscles) and pressure via intrinsic stretch receptors. Primary sensory endings on intrafusal fibers have been shown to be responsive even to small degrees of stretching. The treatment system, in some instances, may expose these middle ear muscles to tensions.

As described in detail within the '839 Publication, the tensor tympani is innervated in afferent and efferent (motor) pathways by the trigeminal nerve. Afferent projections from these muscles can arise from stretch receptors that serve as intrinsic muscle spindles and are particularly dense in the tensor tympani. Eccentric stretch of the tensor tympani can occur when the tympanic membrane is stretched outwardly, which can occur when the treatment system applies a negative pressure fluid flow to the ear canal. This action may generate receptor potentials that give rise to afferent impulses that inhibit pain in a manner consistent with the gate control theory of pain.

The role of detection of the extent and speed of muscle stretch may be attributed to muscle spindle receptors associated with intrafusal fibers, embedded within extrafusal muscle fiber tissue. Muscle spindles can be responsible for the sense of position while tendon organs are provided with a sense of tension. Upon a change in muscle tension, the muscle spindles and tendon organs can send signals through afferent sensory neurons that are relayed to neurons within the spinal cord and brainstem. The allotment of intrafusal fiber density can differ according to functional specialization among different muscles. Intrafusal fiber density can be particularly high in the highly specialized tensor tympani, which may arise due to the fine degree of control required from this muscle. Muscle stimulation can activate the central nervous to a significant extent, both in magnitude and breadth, including some unique regions of the brain to provide a therapeutic effect to treatment various neurological disorders.

Providing a combination of pressure-regulating treatment with caloric stimulation may advantageously have a synergistic effect, such as to increase the therapeutic effect of the treatment. The caloric stimulation may allow the treatment system to alter the temperature of the relevant middle ear muscle and/or receptors before, during, and/or after pressure treatment. For example, the treatment system may provide a flow of heated and/or cooled fluid through a user's ear canal prior to the application of pressure therapy, as described herein. Heated fluid flow may warm up the ear canal and corresponding muscles (e.g., middle ear muscles) and/or receptors. The increased heat may, in turn, increase the metabolic rate of the mechanoreceptors (e.g., on the tympanic membrane, middle ear muscles, etc.) to "prime" the receptors. In some embodiments, priming the receptors prior to the application of pressure regulation treatment can cause the mechanoreceptors to produce stronger neurological responses when the receptors are stimulated. Accordingly, the application of heat prior to and/or in conjunction with any form of treatment (e.g., pressure therapy or any other therapy described in the '839 Publication) can magnify the neurological response to the applied therapy.

Figure 2:
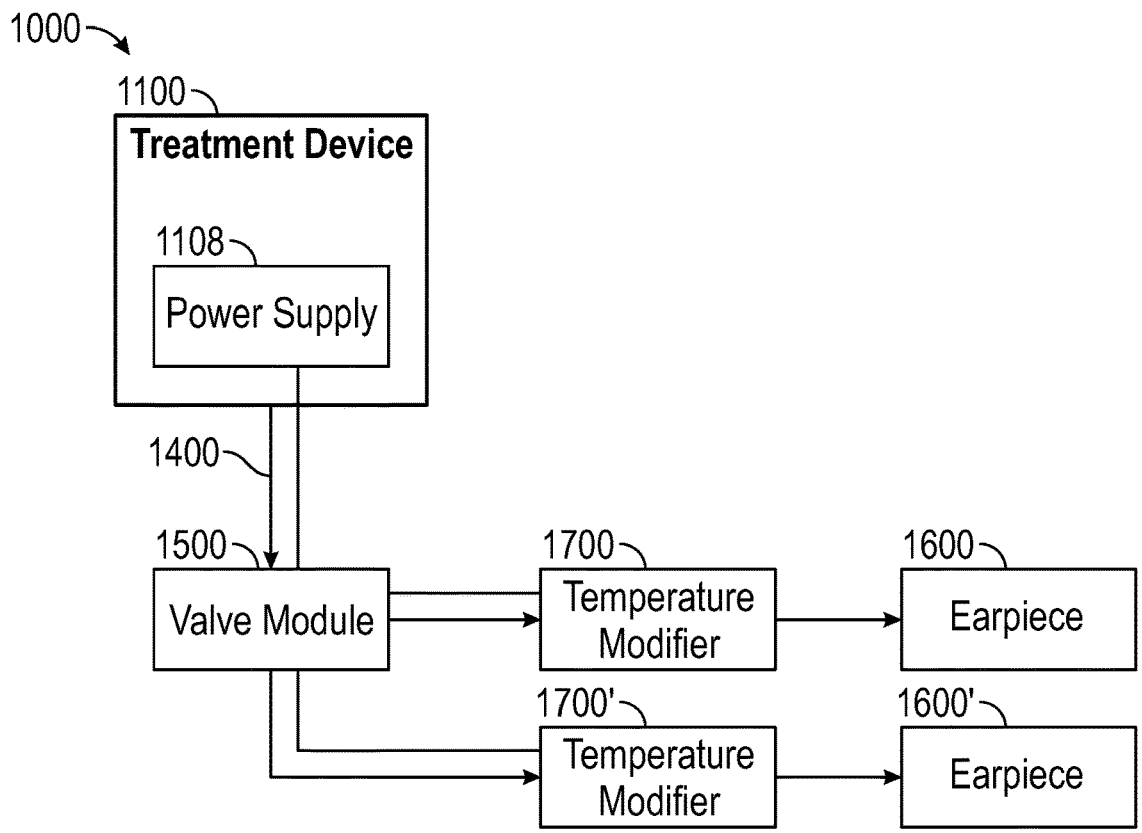
FIG. 2 illustrates a block diagram of an example treatment system having a treatment device in communication with heating elements.
Figure 3A:
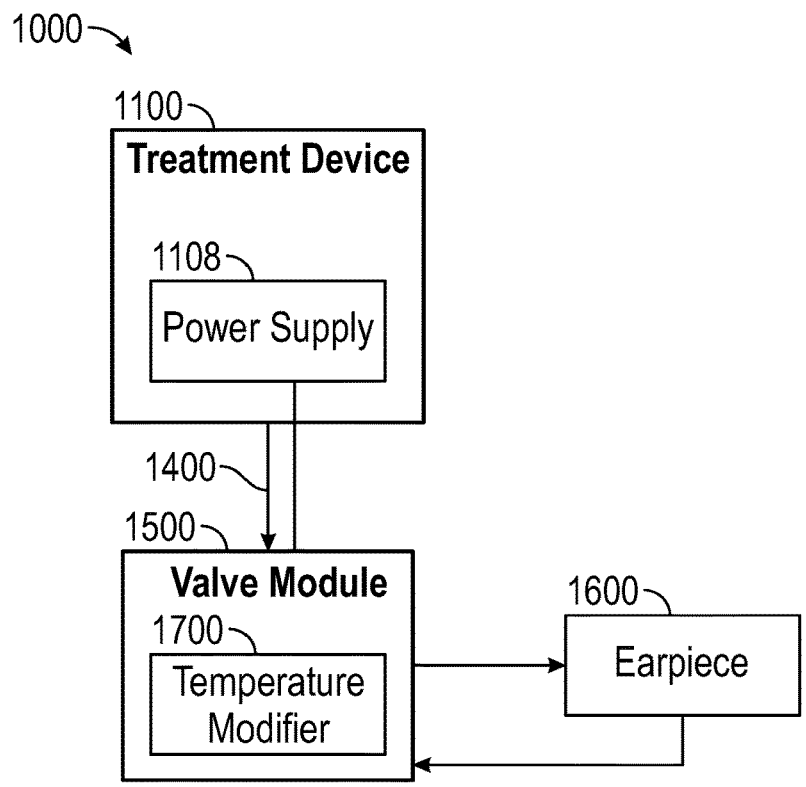
FIG. 3A illustrates a block diagram of an example treatment system having a treatment device in communication with a heating element and an earpiece.
Figure 3B:
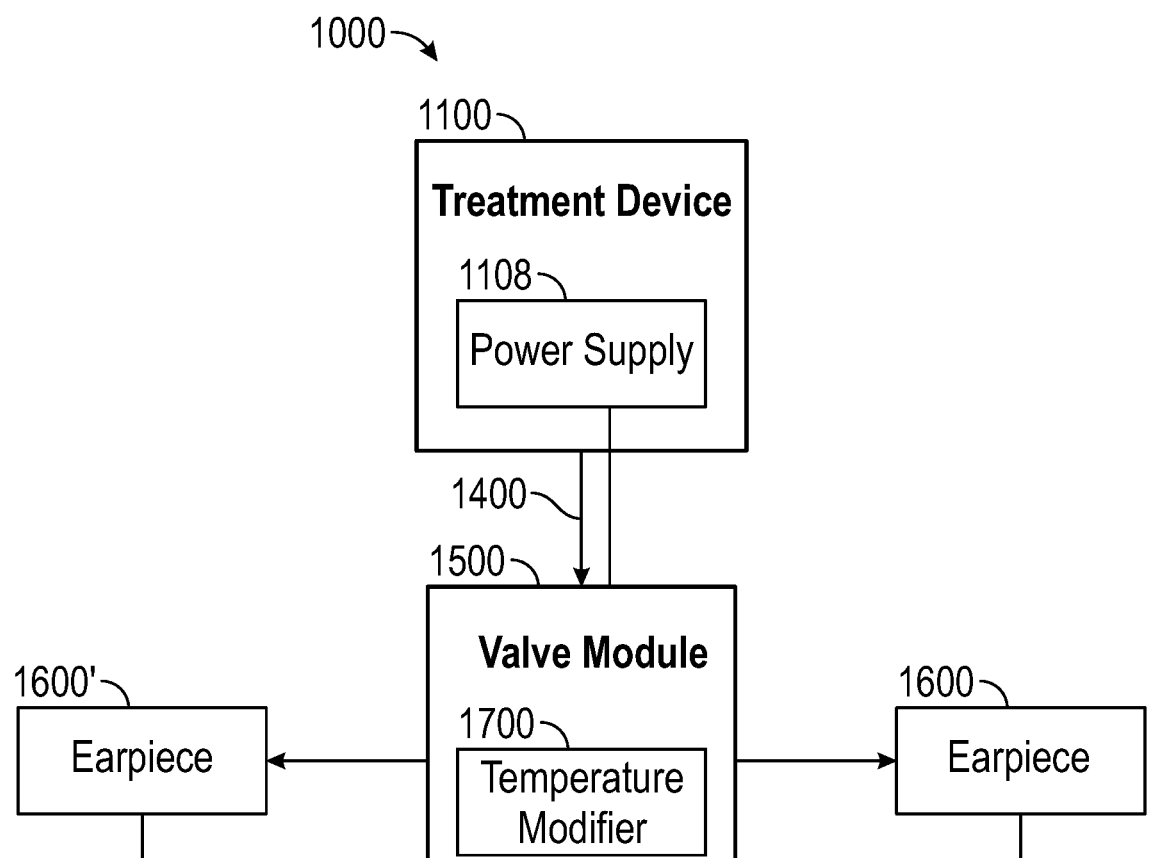
FIG. 3B illustrates a block diagram of the example treatment system of FIG. 3A having multiple earpieces.

FIGS. 2, 3A, and 3B illustrate various block diagrams of example treatment systems 1000 configured to apply caloric treatment and/or pressure treatment. Unless otherwise noted, reference numerals in FIGS. 2-3B refer to components that are the same as or generally similar to the components having the same reference numerals in the remaining figures disclosed herein or in the '839 Publication. It will be understood that the systems and features shown in FIGS. 2-3B can be used with FIG. 1 or with any of the embodiments described and/or contemplated herein or in the '839 Publication. It will also be understood that any of the embodiments described and/or contemplated herein or in the '839 Publication can be modified to be used with the systems and features disclosed in connection with FIGS. 2-3B.

As shown in FIG. 2, the treatment system 1000 can include a treatment device 1100. The treatment device 1100 may be in communication with at least one of a valve module 1500, one or more earpieces 1600, 1600', and one or more temperature modifiers 1700, 1700'. In some embodiments, the valve module 1500, the one or more earpieces 1600, 1600', and/or the temperature modifiers 1700, 1700' can be part of the treatment device 1100. For example, the valve module 1500 or the components thereof can be housed in the same housing as the components of the treatment device 1100.

The treatment system 1000, in some instances as described herein, may be configured to selectively apply heat (e.g., caloric treatment) to one or both ears at the same and/or different times during a treatment session, without the user needing to reposition an earpiece. The treatment system 1000 can selectively apply pressure and heating or cooling or irrigation to the ear(s) while the corresponding earpiece(s) are sealed in the ear(s). The earpiece seal does not need to be broken or disengaged to provide a stream of irrigation (e.g., for heating or cooling) through ear, in some implementations. The treatment system 1000 can have a first (e.g., left) earpiece 1600 and a second (e.g., right) earpiece 1600'. In some embodiments, the treatment system 1000 may include one or more valve modules 1500. The valve module 1500 may be configured to selectively establish fluid communication between the treatment device 1100 and one or both of the one or more earpieces 1600, 1600'. In some embodiments, a single earpiece 1600 can be used, and the system can be configured to deliver treatment (e.g., heating, cooling, and/or pressure) to a single ear, or to one ear at a time. In some embodiments, the second earpiece 1600', the second temperature modifier 1700', and/or the valve module 1500 can be omitted.

With reference to FIG. 2-3B, the treatment system 1000 may comprise one or more temperature modifiers 1700, 1700', such as configured to facilitate the application of caloric treatment to the user, or to otherwise apply heat or cooling to the ear. While some embodiments are illustrated and/or described herein as including heating element(s), it will be understood by one having skill in the art that cooling element(s) can be used in place of the heating element(s). Any temperature regulating device configured to alter the temperature (e.g., for heating or cooling) of a fluid flowing through the fluid pathway towards an earpiece can be used. For example, cooling element(s) can be configured to lower the temperature of a fluid to below room temperature and/or to below body temperature. The system can use heating element(s) that can be configured to raise the temperature of the fluid to above room temperature and/or to above body temperature. The temperature modifier(s) 1700, 1700' can include a thermoelectric cooler, a thermoelectric heater, a heat pump, a Peltier device, or the like. In some cases, the temperature modifier(s) 1700, 1700' can be configured to selectively provide heating and cooling, such as depending on a direction of current applied to the temperature modifier(s) 1700, 1700'.

In various embodiments discussed herein, caloric treatment can be transitioned from one ear to the other. If the treatment system 1000 has a single earpiece 1600, for example as illustrated in FIG. 3A, the user can be provided an instruction to move the earpiece 1600 from one (e.g., left) ear to the other (e.g., right) ear. If the system has two earpieces 1600, 1600', for example as illustrated in FIGS. 2 and 3B, and a manual valve module 1500, the user can be provided with an instruction to toggle the valve module 1500 manually to change the treatment from one ear to the other ear. If the system has two earpieces 1600, 1600' and an automated valve module 1500, the system can toggle the valve module 1500 without any involvement from the user. Similarly, in various embodiments discussed herein, the system can select whether to provide treatment to the right ear or left ear. As shown and discussed in connection with at least FIGS. 3A-B, 5A-B, 6A-I, and 7, the valve module can have one or more valves that can be opened or closed to enable fluid (e.g., air) to be delivered to a right ear piece only, a left earpiece only, or both. Although clearly shown in FIGS. 3A-B, 5A-B, 6A-I, and 7, the following description is provided by way of further clarity. In some implementations, a first fluid conduit (e.g., tube) can extend from the valve module 1500 (or from the treatment device 1100 if the valves are incorporated therein) to the earpiece 1600 or 1600'. Fluid can be driven through the first conduit towards the earpiece 1600 or 1600' for positive pressure or for irrigation (e.g., a stream of fluid being delivered to the ear). Fluid can be drawn through the first conduit away from the earpiece 1600 or 1600' for negative pressure. Valves can be opened or closed to enable fluid transfer to or from the earpieces 1600 and 1600' through the respective first conduits. A second fluid conduit (e.g., tube) can extend from the earpiece 1600 or 1600' to the valve module 1500 (or to the treatment device 1100 if the valves are incorporated therein). One or more valves can selectively vent the second fluid conduit to the ambient area outside the device. When open, the system can perform irrigation where a stream (e.g., a continuous flow in some cases) of fluid is pushed through the first fluid conduit and through the earpiece into the ear. As additional fluid is delivered into the ear, fluid is driven through the earpiece, and through the second fluid conduit, and out to the ambient area outside the device. In some implementations, the fluid can be recirculated. For example, instead of being vented out of the device like an exhaust, the same fluid can be recirculated back to the ear. The fluid can be reheated or re-cooled and can be recirculated back to the ear. In some cases, the flow can be reversed and air can be drawn in through the second fluid conduit, and delivered to the ear, and then drawn through the first fluid conduit. When closed, the system can apply pressure to the ear. The earpiece 1600 can remain sealed with the ear in both the pressure mode and the irrigation or caloric mode. The system 1000 can transfer between the pressure mode and the irrigation or caloric mode without input or involvement from the user, and without changing the sealing engagement of the earpiece with the ear. In some embodiments, one or more valves (e.g., an outlet valve for venting to the ambient area) can be incorporated into the earpiece(s). For example, a wired connection can be provided to the earpiece(s) for delivering command signals (e.g., to operate the valve(s)) and/or for providing power to operate the valve(s). In some cases, wireless command signals can be used, and the earpiece(s) can have a separate power source (e.g., a battery). Wireless communication signals can also be used to control the valve module (which can have a separate power source, such as a battery).

The one or more temperature modifiers 1700, 1700' may selective establish caloric therapy to one or more ears via one or more earpieces 1600, 1600' by any suitable approaches, such as by selectively heating and/or cooling a fluid (e.g., air) being input into the ear(s). For example, the one or more temperature modifiers 1700, 1700' may comprise a resistive wire (e.g., made of Nichrome or other suitable material), located along a tubing that defines the fluid pathway between the treatment device 1100 and the one or more earpieces 1600, 1600'. It is to be appreciated that such a resistive wire is exemplary more generally of a conductive material, and that other appropriate conductive materials may also be used according to one of ordinary skill. The resistive wire can be in thermal communication with the fluid (e.g., air) in the tubing. The resistive wire may increase in temperature when an electric current is applied to the wire and, consequently, the wire may apply thermal energy to a fluid within the tube to heat up the fluid. The resistive wire, in some instances, may be located along an inner surface of the tubing and/or incorporated (e.g., embedded) into the walls of tubing. The resistive wire can be coiled, such as in a helix pattern. The resistive wire can extend along a length of the tube having a distance of 2 cm, 4 cm, 6 cm, 8 cm, 10 cm, 12 cm, 14 cm, 16 cm, 18 cm, 20 cm, 22 cm, 24 cm, 26 cm, 28 cm, 30 cm, or more, or any values therebetween, or any ranges bounded by any combination of these values, although other values could also be used in some cases. The resistive wire can be disposed outside the earpiece 1600, or can extend into the earpiece 1600 in some embodiments. The temperature modifier 1700 (e.g., the resistive wire) can be positioned within a distance of 0.1 cm, 0.2 cm, 0.5 cm, 1 cm, 2 cm, 3 cm, 5 cm, 7 cm, 10 cm, 15 cm, or 20 cm from the ear piece 1600, or any values therebetween, or any ranges bounded by any combination of these values, although other distances are also possible. Heating or cooling the fluid (e.g., air) in close proximity to the earpiece 1600 can impede the fluid from changing temperature significantly after being heated or cooled and before being applied to the ear. The temperature modifier 1700 can be outside the earpiece 1600. The temperature modifier 1700 can be adjacent to the earpiece 1600. The temperature modifier 1700 can be inside the earpiece 1600. As shown in the figures and described herein, it is also appreciated that the temperature modifier 1700 can be closer to the earpiece 1600 than to the treatment device and/or fluid flow generator and/or valve module.

The temperature modifier 1700 (e.g., resistive wire) may be powered by any suitable power supply (e.g. power supply 1108 of the treatment device 1100 illustrated in FIG. 1). A wire can electrically couple the temperature modifier 1700 to the power supply 1108 (e.g., a battery) of the treatment device 1100. The wire can extend along an outside of the tubing, along an inside of the tubing, or can be embedded in the wall of the tubing. The wire can have an insulating cover. In some cases, one or more lumens can transport fluid (e.g., air) for producing pressure or fluid irrigation, and a separate lumen can include one or more wires, such as for providing electrical power or signals. In some cases, the wire is embedded in the wall of the tubing, such that the material of the tubing wall provides an insulating cover for the wire. In some cases, the resistive wire of the temperature modifier can be uninsulated. The resistive wire of the temperature modifier can have a higher resistance than the wire for electrically coupling the temperature modifier 1700 to the power supply 1108. The valve module 1500 can be configured to transfer electrical power and/or signals from the tube(s) extending between the treatment device 1100 and the valve module 1500 to the tube(s) extending between the valve module 1500 and the earpiece(s) 1600, 1600'. In some cases, the tube(s) extending from the treatment device 1100 to the valve module 1500 can have two wires: a first wire that is in electrical communication with the first temperature modifier 1700, and a second wire that is in electrical communication with the second temperature modifier 1700'. The valve module 1500 can have electrical pathways that couple the electrical wire(s) of the input tubing to the electrical wire(s) of the output tubing that leads to the earpiece(s). The valve module 1500 can have a first electrical pathway to couple the first wire to a wire on the tubing that leads to the first temperature modifier 1700 and/or the first earpiece 1600. The valve module 1500 can have a second electrical pathway to couple the second wire to a wire on the tubing that leads to the second temperature modifier 1700' and/or the second earpiece 1600'. In some embodiments, the system (e.g., the valve module 1500) can have a splitter or a switch, so that electrical power and/or signals from a single wire can be selectively directed to the first temperature modifier 1700, the second temperature modifier 1700', or both.

In some embodiments, the one or more temperature modifiers 1700, 1700' may comprise cooling element(s), as described herein. For example, the one or more temperature modifiers 1700, 1700' may include one or more thermoelectric cooling devices (e.g. a Peltier device) that can be used or configured to lower a fluid temperature prior to entering the user's ear canal. The one or more temperature modifiers 1700, 1700', in some instances, may comprise one or more heating or cooling packs. The heating and/or cooling packs may comprise various chemical-containing reservoirs that are initially isolated from each other. When the chemicals are no longer isolated and come into contact with each other (e.g. through destruction of the individual reservoir barriers), the combination of the chemicals can generate exo- or endo-thermic reactions to release or absorb heat, respectively. For example, the packs may include blister packs that may be manually destroyed. By way of another example, the reservoirs may be separated by a barrier (e.g. a metal foil) that is configured to disintegrate when an electric current is applied to the barrier. As such, a current can be applied to the heating and/or cooling packs to selectively release the chemicals and control the timing and/or intensity of the heating and/or cooling. The heating and/or cooling packs can be inside or on an ear piece 1600 or 1600'. In some cases, the heating and/or cooling packs can transfer heat to the ear through the earpiece 1600 or 1600'. The heating and/or cooling packs heat or cool the fluid that is being delivered to the ear. The system can include multiple heating and/or cooling pack, which can be selectively activated, such as in parallel to control the amount of heating and/or cooling, and/or in series to control a time duration of the heating and/or cooling.

In some embodiments, the one or more temperature modifiers 1700, 1700' may utilize the application of electromagnetic energy to alter the temperature of a fluid and/or at least a portion of the user's ear canal. For example, the temperature modifiers 1700, 1700' may comprise a light source that directs light directly into a portion of the user's ear canal (e.g., the tympanic membrane) and/or at a fluid flowing into the user's ear canal. An infrared light source can be used to output infrared light to heat the user's ear and/or fluid flowing into the ear. Any suitable type of light source can be used, such as an incandescent light source, a visible light source, a broadband light source, an incandescent bulb, a light emitting diode (LED), a laser, etc. The earpiece 1600 can include a light source positioned to direct light into the ear.

The temperature modifiers 1700, 1700', in some instances, may reside within the earpiece 1600, 1600' to apply caloric therapy directly to the user's ear canal. In some embodiments, the one or more temperature modifiers 1700, 1700' can be incorporated into the one or more earpieces 1600, 1600'. The temperature modifier 1700 (e.g., a thermoelectric heating or cooling device) can apply heating or cooling to the ear by thermal conduction through a sidewall of the earpiece, for example. In some embodiment, the wire(s) can extend along the tubing to the earpiece(s) 1600, 1600'.

As illustrated in FIG. 2 and discussed herein, in some embodiments, the treatment system 1000 can include two temperature modifiers: a first temperature modifier 1700 to apply heating and/or cooling (e.g., for caloric therapy) to a first ear through the first earpiece 1600 and a second temperature modifier 1700' to apply heating and/or cooling (e.g., for caloric therapy) to a second ear through the second earpiece 1600'. This configuration can enable different temperatures to be applied simultaneously to the different ears. In some embodiments, the treatment system 1000 could select whether to apply heating and/or cooling (e.g., for caloric treatment) to only the right ear or to only the left ear by controlling which temperature modifier is activated. Various features described herein in connection with a single earpiece can be applied to both earpieces in a system that includes two earpieces. Various features described in connection with two earpieces can be used with a single earpiece (e.g., in a single earpiece system, or in one earpiece of a multiple earpiece system).

In some embodiments, the one or more temperature modifiers 1700, 1700' may be automated and configured to be controlled by the treatment system 1000. For example, the treatment system 1000 may be configured control the selective heating and/or cooling using the temperature modifier(s) 1700, 1700' based on a treatment profile without requiring user interaction. The temperature modifier(s) 1700, 1700' can be electronically actuated to selectively apply heating and/or cooling (e.g., for caloric treatment) between the left and right earpieces and, in some cases, to both earpieces as well. The treatment device 1000, in some implementations, may comprise a wired connection to temperature modifier(s) 1700, 1700', as described herein. The wired connection may be configured to send signal to the temperature modifier(s) 1700, 1700' to alter the temperature of fluid passing through the various fluid pathways, as described herein. The wired connection can supply power to one or more temperature modifiers 1700, 1700' to selectively set the temperature using the temperature modifier(s) 1700, 1700'. The wire(s) can run inside the tube, outside the tube, and/or can be embedded inside the wall of the tubing.

As illustrated in FIG. 2, the one or more temperature modifiers 1700, 1700' may reside along the tubing between the valve module 1500 and the one or more earpieces 1600, 1600', external to the valve module 1500. For example, the tubing may comprise a single fluid pathway connecting the treatment device 1100 to the valve module 1500 and then split into two or more fluid pathways at the valve module 1500. Each of the two or more fluid pathways may be connected to a particular earpiece and may be selectively heated and/or cooled by the one or more temperature modifiers 1700, 1700'. Additionally or alternatively, in some embodiments (e.g., as illustrated in FIGS. 3A and 3B), the one or more temperature modifiers 1700 may be located within the valve module 1500. For example, the temperature modifier 1700 may be connected to an outlet of the valve module 1500 having one (e.g., as illustrated in FIG. 3A) or more (e.g., as illustrated in FIG. 3B) tubings extending therefrom. The valve module 1500 can comprise the temperature modifier 1700. However, while the temperature modifier 1700 is illustrated in FIGS. 2-3B as residing outside of the treatment device 1100, it will be understood by one of ordinary skill in the art that the heating element 1700 may be located within a housing of the treatment device 1100. For example, the heating element 1700 may be connected to the outlet 1400 (shown in FIG. 1) extending therefrom. As also disclosed elsewhere herein, it is also appreciated that the valve module 1500 can be incorporated into the treatment device 1100. The valve module 1500 can be omitted, and the treatment device 1100 can include one or more valves to implement the features described in connection with the valve module 1500. In some implementations, the valve module 1500 and the temperature modifier(s) 1700 can be part of the treatment device 1100 (e.g., sharing a common housing).

In some embodiments, the treatment system 1000 can include one or more sensors configured to detect one or more operating conditions of the treatment device 1100 (e.g. sensor 1118 as shown in FIG. 1). For example, the sensor may comprise a temperature sensor that is configured to measure the temperature within at least a portion of the treatment device 1100, the one or more earpieces 1600, 1600', and/or the user's ear (e.g., in the external ear canal). The temperature sensor can measure the temperature in the tubing, the valve module 1500, or any other suitable location, which can in some examples provide information regarding a corresponding temperature in the ear. A processor (e.g., processor 1104 as shown in FIG. 1) may monitor the temperature measured by the sensor and can control the one or more heating elements 1700, 1700' to achieve the temperatures set by a temperature treatment profile, in some embodiments. In implementations, the temperature sensor(s) can be incorporated into the earpiece(s) 1600, 1600', and can be positioned in or near the ear. The controller and temperature sensor can monitor the temperature at the ear and/or earpiece 1600 and can apply heat or cooling until a target temperature is reached. In some cases, the controller can operate the temperature modifier(s) 1700, 1700' to maintain a target temperature for a period of time. In some cases, the temperature sensor(s) can measure the temperature of the fluid (e.g., air) being output by the temperature modifier(s) 1700, 1700'. The controller can operate the temperature modifier(s) 1700, 1700' to output fluid at a target temperature. If the temperature become higher than the target value, the temperature modifier 1700 can reduce heating or increase cooling. If the temperature is lower than the target value, the temperature modifier 1700 can increase heating or decrease cooling. In some embodiments, the temperature sensor can measure fluid (e.g., air) that is entering or leaving the ear. For example, the valve module 1500 can have a temperature sensor to measure the temperature of the fluid that is being expelled from the ear. One or more wires can extend from the treatment device 1100 to the temperature sensor, such as for delivering electrical power, control signals, and/or data (e.g., temperature data). In some cases, the one or more wires can extend to the earpiece(s) 1600, 1600'. Any suitable type of temperature sensor can be used, including but not limited to, a thermocouple, a resistive temperature detector (RTD), a thermistor, an infrared sensor, a thermometer, a semiconductor sensor, etc.

In some embodiments, the treatment system 1000, including one or more temperature modifiers 1700, 1700', can have any of the same or similar components, features, materials, sizes, configurations, and other details of any other pump system embodiments disclosed or incorporated by reference herein, including the embodiment of any of the treatments systems described in the '839 Publication. It will be understood by one having skill in the art that any of the embodiments or features relating to heating and/or cooling (e.g., for caloric treatment) disclosed in the present application can be provided or used in connection with any of the treatment systems described and/or contemplated within International Patent Application No. PCT/US2017/064964 (the '839 Publication), which is incorporated by reference herein in its entirety. Though one or more figures may show a caloric treatment system of a particular embodiment, it shall be understood that any features and/or methods of any treatment system disclosed herein can be used in and/or with any of treatments system disclosed herein.

Examples of Treatment Process and Operation Modes

Figure 4:
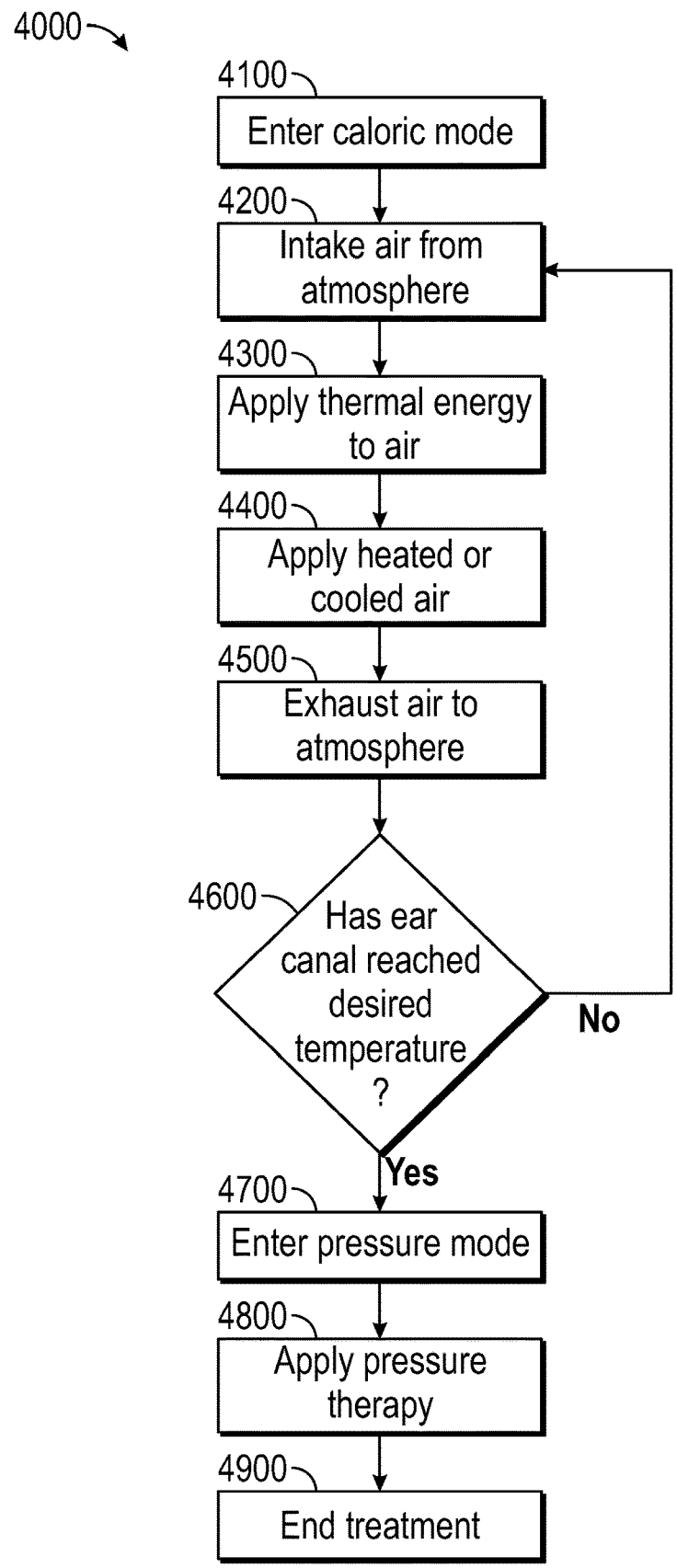
FIG. 4 illustrates a flow chart of a process for applying treatment to a user.

With reference to FIG. 4, in some embodiments, the treatment system can be configured to operate in one or more operational modes. For example, the treatment system can include a caloric mode and a pressure mode. A process 4000 of the treatment system may operate the treatment device differently depending on a selected mode of operation.

At block 4100, the processor may transition the treatment system to caloric mode. In some embodiments, when the treatment system is in caloric mode, the treatment system can be configured to apply heat and/or cooling to the ear canal of a user. The heat and/or cooling, in some instances, may be applied prior to application of pressure therapy. While process 4000 illustrates the application of heating and/or cooling (e.g., for caloric treatment) prior to pressure therapy, it will be understood by one having skill in the art that heating and/or cooling (e.g., for caloric therapy) may be applied at any time (e.g., before, after, or intermittently dispersed throughout application of one or more pressure treatments).

At block 4200, the treatment device may intake fluid to fill a fluid chamber of the treatment system prior to (and/or during) application of caloric treatment. The treatment device ay intake fluid in any manner discussed herein. The system can intake air from the ambient environment outside the treatment system. At block 4300, the treatment system can apply thermal energy to a fluid (e.g., air) to be applied to the ear canal of a user. In some embodiments, as discussed herein, caloric energy may be applied directly to the user's ear canal (e.g., via and earpiece) instead of using heated/cooled fluid. The treatment system may heat and/or cool the fluid prior to transfer of the fluid to the user's ear canal. At block 4400, the treatment system can apply the heated or cooled fluid to the ear canal of a user according to one or more treatment profiles parameters. After application of the fluid to the user's ear canal, at block 4500, the applied fluid may be discarded (e.g., vented to an external environment).

At block 4600, the treatment system may be operated (e.g., continuously) based on feedback from one or more sensors that measure pressure and/or temperature in a fluid flow path and/or the ear canal of the user, as discussed herein. In some embodiments, the processor may alter the treatment device in response to a sensed condition. By way of example, a pressure and/or temperature treatment parameter profile can supply a pressure and/or temperature set point. The processor can operate the treatment device to alter the pressure and/or temperature within one or more ear canals of a patient and monitor the pressure and/or temperature measured by the sensor. For example, when the measured temperature within an ear canal of a user reaches a desired set point, the processor can transition to block 4700. In some instances, when the measure temperature has not reached the set point, the processor can transition back to block 4200. Many variations are possible. The system can apply heating and/or cooling for a predetermined amount of time, and in some cases can then transition to block 4700. The system can apply a predetermined amount of heat and in some cases then transition to block 4700. In some cases, the system can determine whether and when to transition to block 4700 based at least in part on the measured temperature of the fluid (e.g., air) being directed to the ear and/or leaving the ear.

In some embodiments, when the ear canal has reached a desired temperature, and/or caloric mode has been successfully completed in block 4600, and/or the system has otherwise decided to stop applying heat/cooling, the treatment system can transition between caloric mode to pressure mode at block 4700. In some embodiments, a transition between operational modes can be indicated to the user by deactivating and/or activating one or more indicators, as discussed herein. While in the pressure mode, the treatment system may activate the treatment device to generate a level of pressure (i.e., positive and/or negative pressure) within one or both of the ear canals of a user, as described herein for example with reference to FIG. 5B. The treatment system may perform any treatment method or treatment pressure profile disclosed herein and/or in the '839 Publication.

At block 4800, during the pressure mode, the treatment system can activate the treatment device to begin applying pressure therapy and to increase and/or decrease pressure in the system or some portion thereof, such as a fluid flow path between a pressure generator and one or more earpieces. In some embodiments, the treatment system can reduce pressure in the system, such as to a target negative pressure differential between the external ear canal pressure and ambient pressure. The treatment system can increase pressure to produce a positive pressure differential between the external ear canal pressure and ambient pressure. The treatment system can intermittently and/or continuously monitor the pressure in the treatment system or some portion thereof, as discussed herein and/or in the '839 Publication. For example, the treatment system can monitor the pressure in the valve module or in the treatment device or any suitable location (e.g., at a preset sampling rate).

After the treatment system applies the desired treatment profile(s), the processor may end treatment at block 4900. In some embodiments, the treatment system can monitor the duration of time the treatment system remains in the pressure mode. This can be accomplished, for example, by maintaining a timer, which can be reset and started when the treatment system transitions into the pressure mode. The treatment system can automatically end treatment when a time duration exceeds a threshold (e.g., times out). In some embodiments, such threshold can be a preset value, such as between about 1 minute or less and about 1 hour or more, or any values or ranges therein. In some embodiments, the threshold can be set or changed by the user. In some embodiments, the threshold can be varied based on various operating conditions or on any combination thereof. In some embodiments, the treatment system can monitor the entire amount of time spent in the pressure mode and store this information in memory.

In some embodiments, the system can transition from pressure mode to caloric mode. For example, the system can apply pressure treatment while in pressure mode, and then transition to caloric mode to apply heating or cooling for a period of time, and then transition back to pressure mode for additional pressure treatment. This process can be repeated during the treatment session. For example, heating and/or cooling can be applied at time intervals of about 0.5 minutes, about 1 minute, about 2 minutes, about 3 minutes, about 5 minutes, about 7 minutes, about 10 minutes, about 12 minutes, about 15 minutes, about 20 minutes, or more, or any values therebetween, or any ranges bounded by these values, although other times can be used in some cases. It is contemplated that in some implementations, the pressure mode can be applied before the caloric mode. It is contemplated that heating or cooling or caloric stimulation can be applied through other manners instead of applying a heated or cooled fluid to the external ear canal. For example, the earpiece can have a heating or cooling element, and heating or cooling can be transferred through the earpiece to the ear.

Examples of Valve Modules

Figure 5A:
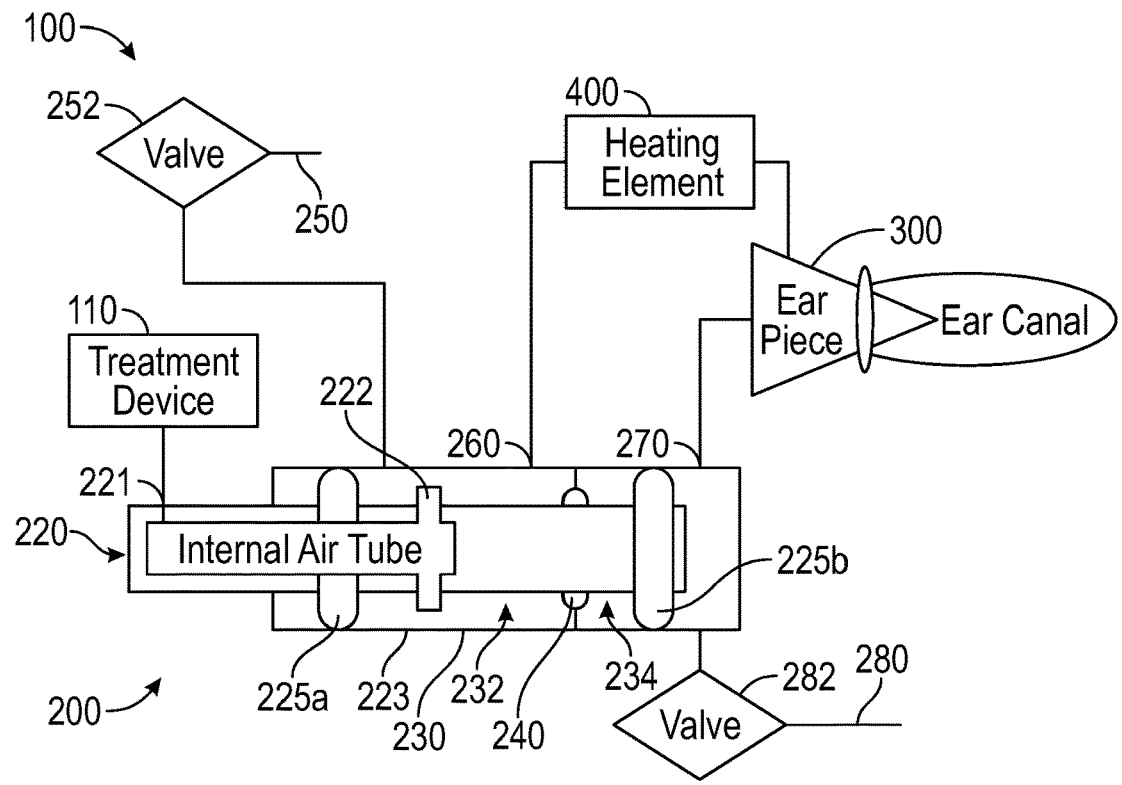
FIG. 5A illustrates a schematic drawing of an example treatment system in a caloric mode.
Figure 5B:
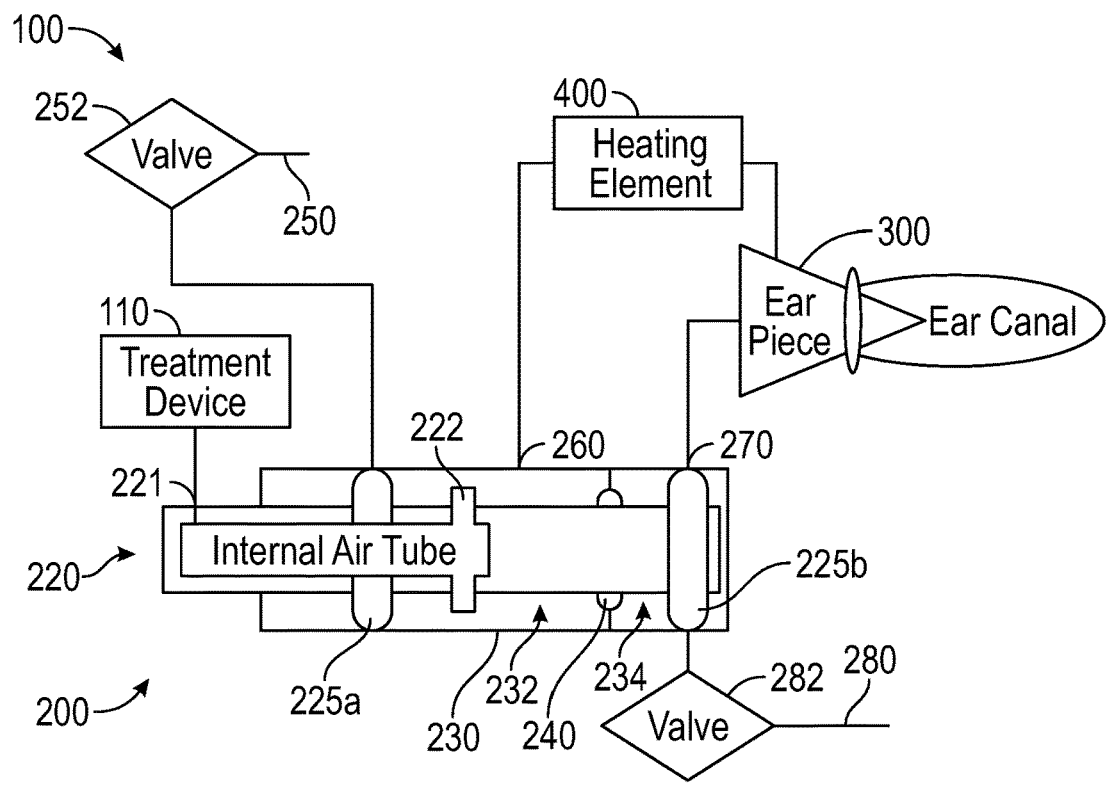
FIG. 5B illustrates a schematic drawing of an example treatment system in a pressure mode.

FIGS. 5A and 5B illustrate schematic views of a treatment system 100, according to some embodiments. In particular, FIG. 5A is an illustration of the treatment system 100 in caloric mode, as described herein, and FIG. 5B is an illustration of the treatment system 100 in pressure mode. Although much of the detail in FIGS. 5A and 5B focuses on the valve module, the system can include the other features disclosed herein for the treatment system 100. Unless otherwise noted, the treatment system 100 as shown in FIGS. 5A and 5B may include components that are the same as or generally similar to the components in the remaining figures discussed herein. It will be understood that the treatment system 100 shown in FIGS. 5A and 5B can be used with any of the embodiments described and/or contemplated herein. It will also be understood that any of the embodiments described and/or contemplated herein can be modified to be used with the treatment system 100 shown in FIGS. 5A and 5B. Any feature, structure, material, method, or step that is described and/or illustrated in the embodiment of FIGS. 5A and 5B can be used with and/or instead of any feature, structure, material, method, or step that is described and/or illustrated in any other embodiment of this specification.

FIGS. 5A and 5B illustrate schematic views of a treatment system 100 with a treatment device 110 in fluid communication with a valve module 200, a heating element 400, and an earpiece 300. The valve module 200 can include a movable member (e.g., a plunger 220), an outer housing 230, a housing inlet conduit 250, an earpiece outlet conduit 260, an earpiece inlet conduit 270, and a housing outlet conduit 280. In some embodiments, the housing 230 can be adapted to support and protect many of the components of the valve module 200. The housing 230 can have one or more air channels in fluid communication with the housing inlet conduit 250 and the housing outlet conduit 280, formed in and/or along an outer surface of the housing 230.

The housing inlet conduit 250 can be used to intake or channel fluid, such as air, from an external ambient environment into a first portion 232 of the housing 230. The housing inlet conduit 250, in some embodiments, may comprise a valve 252, as discussed herein. The housing outlet conduit 280 can be used to exhaust or channel fluid from a second portion 234 of the housing 230 and towards an external ambient environment. The housing outlet conduit 280, in some embodiments, may comprise a valve 282, as discussed herein. The earpiece outlet conduit 260 can be used to export or channel fluid from the first portion 232 of the housing 230 and towards the heating element 400 and/or the earpiece 300. The earpiece inlet conduit 270 can be used to intake or channel fluid from the earpiece 300 into the second portion 234 of the housing 230. The earpiece outlet conduit 260 can include a first tube. The earpiece inlet conduit 270 can include a second tube, which can be separate from the first tube. In some embodiments, the earpiece outlet conduit 260 and the earpiece inlet conduit 270 can be incorporated into a single tube. For example, a tube can have a divider or partition, which can divide the tube into one channel for transporting fluid as the earpiece outlet conduit 260, and a second channel for transporting fluid as the earpiece inlet conduit 270.

As shown in the illustrated embodiment, the movable member (e.g., plunger) 220 can be positioned at least partially within and/or supported by one or more portions of the outer housing 230. The plunger 220 can be configured to translate within the housing 230 from a first position to a second position. The plunger 220, in some embodiments, may be configured to selectively open and close one or more fluid pathways (e.g., the housing inlet conduit 250, the housing outlet conduit 280, the earpiece inlet conduit 270, etc.) to switch the treatment system 100 between various operational modes. For example, the treatment system 100 can be in caloric mode when the plunger 220 is in the first position (as illustrated in FIG. 5A), and the treatment system 100 can be in pressure mode when the plunger 220 is in the second position (as illustrated in FIG. 5B).

The valve module 200 can be fluidly coupled to the treatment device 110. In some cases fluid be transferred to or from the treatment device 110 from or to the valve module 200 via the plunger 220, although other designs are possible. As shown in FIGS. 5A and 5B, the plunger 220 can include a plunger inlet conduit 221 in fluid communication with the treatment device 110 and a plunger outlet conduit 222. For example, the plunger inlet conduit 221 can be used to connect the valve module 200 to the treatment device 110. The plunger outlet conduit 222 can form an initial fluid flow pathway through the valve module 200 to permit fluid flow between the treatment device 110 and an internal portion of the housing 230 (e.g., a first portion 232, as described herein). The treatment device 110 may be configured to regulate a fluid flow through the housing 230 and one or more earpieces 300 to apply caloric and/or pressure treatment to a user. The treatment device 110 can comprise any embodiment disclosed herein and/or in the '839 Publication. The treatment device 110 can include a pressure generator, which can produce a positive pressure that pushes fluid into the valve module 200, and/or which can produce a negative pressure that pulls fluid out of the valve module 200. In some embodiments, a fluid conduit (e.g., a tube) can couple the treatment device 110 to the housing 230, such as at location 223 in FIG. 5A. The treatment device 110 can be fluidly coupled to the valve module 200 (e.g., to the first portion 232 of the internal cavity, without going through the plunger 220. Accordingly, in some embodiments, the plunger inlet conduit 221 and the plunger outlet conduit 222 and the internal air tube shown in FIG. 5A can be omitted.

In some embodiments, the valve module 200 can include a housing seal 240 which can protrude from an inner surface of the housing 230 to engage with the plunger 220. The plunger 220, in some embodiments, can be received within the housing seal 240 to form a friction and/or interference fit. The housing seal 240 can separate an internal cavity of the housing 230 into two portions (e.g., a first portion 232 and a second portion 234) through the housing seal 240. The friction and/or interference fit can be configured to impede fluid flow between the two portions 232, 234 through the housing seal 240, while permitting the plunger 230 to move with respect to the housing seal 240. The housing seal 240 can be affixed to the inner surface of the housing 230 to impede the housing seal 240 from moving with respect to the housing 230. The housing seal 240 can include an O-ring, which can engage the plunger 220. The housing seal 240 in some embodiments can be made of a flexible, resilient material. In some embodiments, the housing seal 240 can include a barrier, such as a wall between the first portion 232 and the second portion 234. Some embodiments do not have a plunger that extends through the housing seal 240, such as if separate actuators are used for the first portion 232 and the second portion 234. Accordingly, in some embodiments, the housing seal 240 can be a wall (e.g., rigid material of the housing 230) that separates the internal cavity into the first portion 232 and the second portion 234. In some embodiments, the housing seal 240 can be omitted, such as if the sealing member 225*b* on the plunger 220 is used to separate the internal cavity into a first portion 232 and a second portion 234.

The treatment system 100 may include a heating element 400 positioned along a fluid pathway between the earpiece outlet conduit 260 of the valve module 200 and the earpiece 300. The heating element 400 may comprise any structure described herein (e.g. temperature modifier 1700 as illustrated in FIGS. 2-3B herein). Although not illustrated in FIGS. 5A and 5B, a cooling element can be used in place of the heating element 400, or a temperature modifier can be used to selectively produce heating or cooling.

As shown in the illustrated embodiment, the valve module 200 may include one or more valves 252, 282 in fluid communication with the housing inlet conduit 250 and the housing outlet conduit 280, respectively, to control fluid flow between the housing 230 and an external environment. The valve 252, in some embodiments, can include a check valve or one-way valve configured to allow fluid flow into the treatment system 100 from the external environment and also configured to inhibit fluid flow out of the treatment system 100 through the housing inlet conduit 250. The valve 282, in some embodiments, can include a separate check valve or one-way valve configured to allow fluid flow out of the treatment system 100 to the external environment and also configured to inhibit fluid flow into the treatment system 100 through the housing outlet conduit 280. In this manner, for example when the treatment system 100 is in the caloric mode, valves 252, 282 can be designed to facilitate to the fluid to flow through the treatment system 100 such that fluid may enter the first portion 232 of the housing 230 from the housing inlet conduit 250 and/or from the treatment device 110 and exit the housing 230 through the housing outlet conduit 280. In some embodiments, the valves 252 and/or 282 can selectively open and close. For example, an actuator can open the valve 252 when the system creates a negative pressure to draw air in through the housing inlet conduit 250, and the actuator can close the valve 252 at other times. An actuator can open the valve 282 when the system pushes air out the housing outlet conduit 280, and can close the valve 282 at other times. FIGS. 5A and 5B show the valves 252 and 282 schematically. The valves can be incorporated into the valve module 200, or can be separate from the valve module 200. For example, the housing 230 can include an opening for the housing inlet conduit 250, and a valve 252 can be supported by the housing 230 to control fluid flow through the opening. The housing 230 can include an opening for the housing outlet conduit 280, and a valve 282 can be supported by the housing 230 to control fluid flow through that opening. In some embodiments, the housing inlet conduit 250 can include a tube that couples the housing 230 to the valve 252, and/or the housing outlet conduit 280 can include a tube that couples the housing 230 to the valve 282.

The treatment device 110 may apply a positive pressure fluid flow from the treatment device 110 to apply caloric treatment when the treatment system 100 is in caloric mode. The fluid can flow through the plunger 220 into the first portion 232 of the housing 230. As the fluid enters the first portion 232, the valve 252 may prevent the fluid from exiting the housing 230 through the housing inlet conduit 250, as described herein. Additionally, the housing seal 240 can prevent the fluid from flowing directly into the second portion 234 of the housing 230. Accordingly, the fluid can be directed to exit the first portion 232 through the earpiece outlet conduit 260 towards the heating element 400 and the earpiece 300. As the fluid flows through the above-described fluid pathway, the heating element 400 can heat the fluid before it passes through earpiece inserted in a user's ear canal. The fluid temperature may be raised as the fluid interacts with the heating element 400. The heated fluid may then enter the earpiece 300, and consequently, the ear canal of a user to affect the internal temperature of the user's ear canal. The fluid may then exit the earpiece 300 and reenter the housing 230 into the second portion 234 of the housing 230 through the earpiece inlet conduit 270. From the second portion 234, the fluid may exit the housing 230 through the housing outlet conduit 280.

In some instances, the treatment device 110 may receive fluid into an internal fluid chamber from the external environment prior to applying caloric and/or pressure treatment. The treatment device 110 may obtain external fluid by applying a negative pressure fluid flow to the plunger 220 and the first portion 232 of the housing 230. The decrease in pressure within the first portion 232 can cause fluid to flow into the first portion 232 through the housing inlet conduit 250 and the valve 252. As described herein, in some embodiments, the valve 252 may comprise a one-way valve that permits fluid to flow into the housing 230 but prevents fluid flow out of the housing 230 through the housing inlet conduit 250.

In some embodiments, as discussed herein, the valve 282 may be a one-way vale that permits fluid to flow out of the housing 230 but prevent fluid flow into the housing 230 through the housing out conduit 280. The one-way nature of the valve 282, in these embodiments, can inhibit a fluid from flowing through the housing outlet conduit 280 and/or the earpiece 300 when the treatment device 110 applies a negative pressure to receive fluid into an internal chamber, as described above. This may advantageously impede fluid from passing through the earpiece 300 when the treatment device 110 applies a negative pressure.

The system can perform a pumping action to produce a continuous or periodic flow of fluid through the valve module 200, heating element 400, and ear piece 300, such as for irrigation of the ear with heated fluid. The treatment device 110 (or other pressure generator or pump) can produce a negative pressure that causes fluid to flow into the valve module 200 through the housing inlet conduit 250. The valve 252 can be a check valve that permits fluid to flow in through the housing inlet conduit 250, and the valve 282 can be a check valve that prevents fluid from flowing into the valve module 200 through the valve outlet conduit 280. In some embodiments, the valve 252 can be open while the valve 282 can be closed during the negative pressure pumping stage. The treatment device 110 (or other pressure generator or pump) can then produce a positive pressure that pushes fluid out of the valve module 200 through the earpiece outlet conduit 260 towards the heating element 400 and/or the ear piece 300. The valve 252 can be a check valve that impedes fluid from flowing out through the housing inlet conduit 250 during the positive pressure pumping stage. The valve 282 can be a check valve that permits fluid to flow out of the valve outlet conduit 280, so that pressure does not build up in the ear during caloric mode operation. In some embodiments, the valve 252 can be actuated to a closed configuration while the valve 282 can be actuated to an open configuration during the positive pressure pumping stage. By repeating the negative pressure pumping state and the positive pressure pumping stage, the system can drive fluid from the ambient environment, into the valve module 200, through a conduit to the heating element 400, and to the earpiece (e.g., for delivery into the ear canal), and then from the earpiece back to the valve module 200, and then back out to the ambient environment.

In some embodiments, the valve 252 and the housing inlet conduit 250 can be omitted. The treatment device 110 can include a fluid intake for receiving fluid into the treatment device 110. The treatment device 110 can include a valve (e.g., a check valve or selectively openable and closable valve), which can operate similar to the valve 252. With reference to FIGS. 5A and 5B, the movable member (e.g., plunger 220) may move to the first position to transition the treatment system 100 to caloric mode and may move into the second positon to transition the treatment system 100 to pressure mode. In some embodiments, the plunger 220 can include one or more sealing members 225a, 225b, such as an O-ring, positioned around an outer surface of the plunger 220. The sealing members 225a, 225b can advantageously be positioned between the plunger 220 and the housing 230 to selectively open and/or close one of more fluid pathways between the internal cavity of the housing 230 and an external environment (e.g., the earpiece 300 and/or the ambient atmosphere). For example, when the treatment system 100 is in caloric mode, the sealing member 225b can be positioned at a location offset from the earpiece inlet conduit 270 to permit fluid communication between the earpiece 300 and the second portion 234 of the housing 230 through the earpiece inlet conduit 270 (as shown in FIG. 5A). When in caloric mode, the sealing member 225b can be positioned at a location offset from the housing outlet conduit 280 to permit fluid to flow out through the housing outlet conduit 280, as discussed herein. When in caloric mode, the sealing member 225a can be positioned at a location offset from the housing inlet conduit 250 to permit fluid to flow in through the housing inlet conduit 250, as discussed herein. With reference again to FIG. 5B, when the treatment system 100 is in pressure mode, the sealing member 225b may be moved to a position against the earpiece inlet conduit 270 to close the fluid pathway between the earpiece 300 and the second portion 234 of the housing. When in pressure mode, the sealing member 225b may be positioned to close the housing outlet conduit 280. When in pressure mode, the sealing member 225a may be positioned to close the housing inlet conduit 250. A solenoid or other actuator can move the plunger 220 relative to the housing 230.

In some embodiments, the plunger 220 can be omitted. For example, valves 252 and 282 can be closed to transition the valve module 200 to pressure mode. When in caloric mode, the valves 252 and 282 can be selectively opened and closed based on the positive and negative pressure pumping stages, as discussed herein. Actuators can open and close the valves 252 and 282, instead of using check valves.

The treatment device 110, when the treatment system 100 is in pressure mode, may apply a positive and/or negative pressure fluid flow from the treatment device 110. When the treatment device 110 applies positive pressure when in pressure mode, the positive pressure can push fluid through the ear piece 300 and into the ear canal. The fluid can be prevented from exiting the earpiece 300, and ultimately the housing 230, through the earpiece inlet conduit 270 as the plunger seal 225b can be positioned to prevent fluid flow out of the housing 230 through the housing outlet conduit 280. Accordingly, the plunger seal 225b may cause fluid, and consequently pressure, to build up within the earpiece 300 and the external ear canal of a user. The treatment system 110 can be configured to apply a sufficient or variable amount of pressure increase according to a desired treatment profile.

With continued reference to FIG. 5B, when the treatment device 110 applies negative pressure when in pressure mode, fluid may be drawn away from the earpiece 300 and the ear canal of a user to apply a negative pressure treatment to a user. The application of negative pressure by the treatment device 110 may cause fluid to flow through the plunger 220 from the first portion 232 of the housing 230. As the fluid flows out of the first portion 232 of the housing 230, fluid can be prevented from entering the housing 230 through the housing inlet conduit 250 to prevent the external fluid from equalizing the pressure differential build up within the first portion 232. In some embodiments, the plunger seal 225a can be positioned against the housing inlet conduit 250 to prevent a fluid flow into the housing 230 through the housing inlet conduit 250. Accordingly, the plunger seal 225a may cause fluid to flow out of the earpiece 300 and the external ear canal of a user through the earpiece outlet conduit 260 upon the application of a negative pressure fluid flow by the treatment device 110. Consequently, the pressure within the earpiece 300 and the ear canal of a user will decrease (e.g., to below ambient pressure). The treatment system 110 can be configured to apply a sufficient or variable amount of pressure decrease according to a desired treatment profile.

In some embodiments, the valve module 200 may be automated and configured to be controlled by the treatment device 110. For example, the treatment device 110 may be configured to control the selective transitioning of the valve module 200 from the caloric mode (as shown in FIG. 5A) to the pressure mode (as shown in FIG. 5B) based on a treatment profile without requiring user interaction. The valve module 200 can be electronically actuated between the caloric mode and the pressure mode. The treatment device 110, in some implementations, may comprise a wired connection to valve module 200. The wired connection may be configured to send signal to an actuator configured to toggle the valve module 200 between various valve module 200 positions, as described herein. The wired connection can supply power to one or more electronic actuators to selectively set the configuration of the valve module 200. For example, one or more solenoid valves can be used. In some implementations, the plunger 220 can be driven by an electronic actuator. The valves 252 and/or 282 can be electronically controlled as well, such as by electronic actuators, similar to the discussion of the plunger 220. The wire(s) can run inside the housing 230, outside the housing 230, or can be embedded inside the wall of the housing 230. The wire(s) can run along the fluid conduit that couples the treatment device 110 to the valve module 200, such as inside the conduit, outside the conduit, or embedded in the wall of the fluid conduit (e.g., tube).

In some embodiments, the valve module 200 may comprise a wireless receiver (e.g., Bluetooth) configured to receive position information and automatically selectively transition between the caloric and pressure modes in response to the received position information. The valve module 200 can have a power supply (e.g., a battery) for powering the electronic actuator(s).

Examples of Dual-Earpiece Valve Module for Caloric Treatment

Figure 6A:
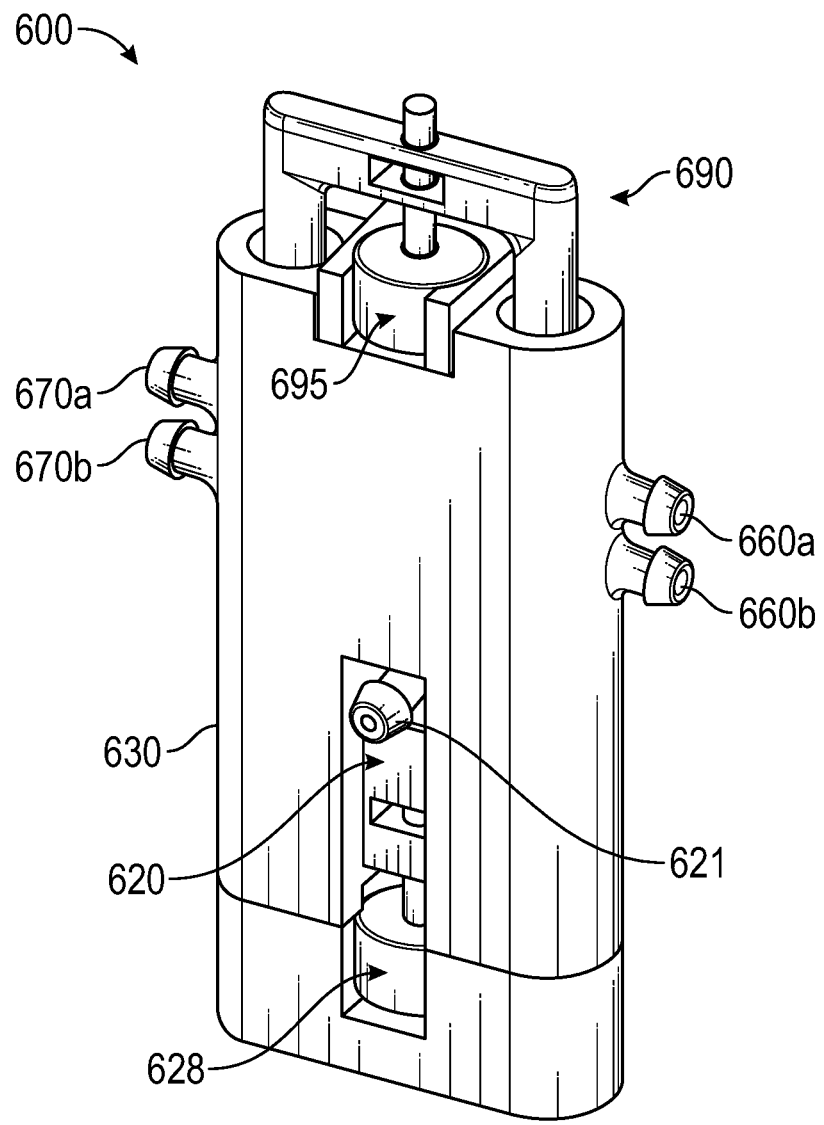
FIG. 6A is a front perspective view of an example valve module.
Figure 6B:
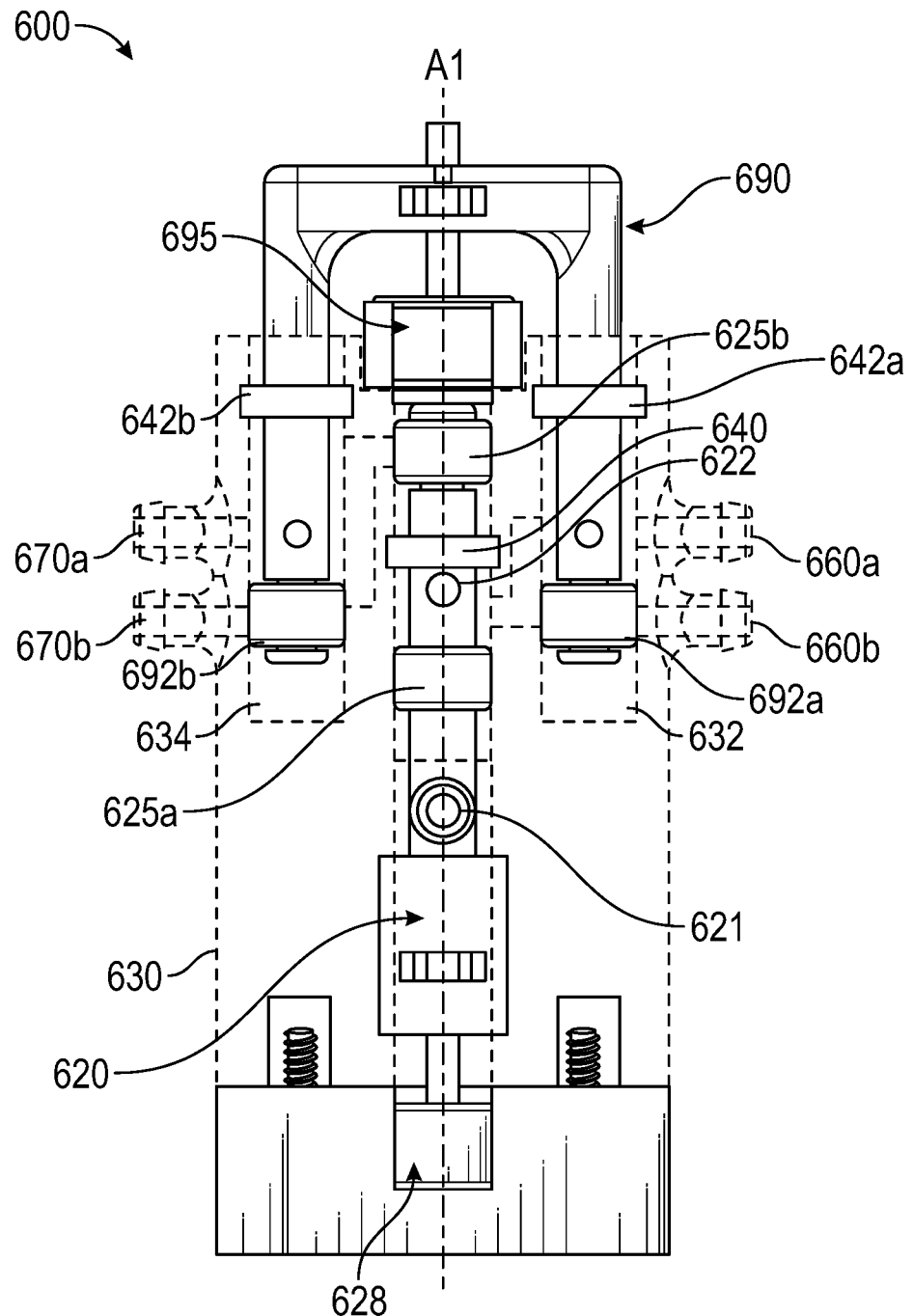
FIG. 6B is a front view of the example valve module of FIG. 6A with various features shown in a transparent view.
Figure 6C:
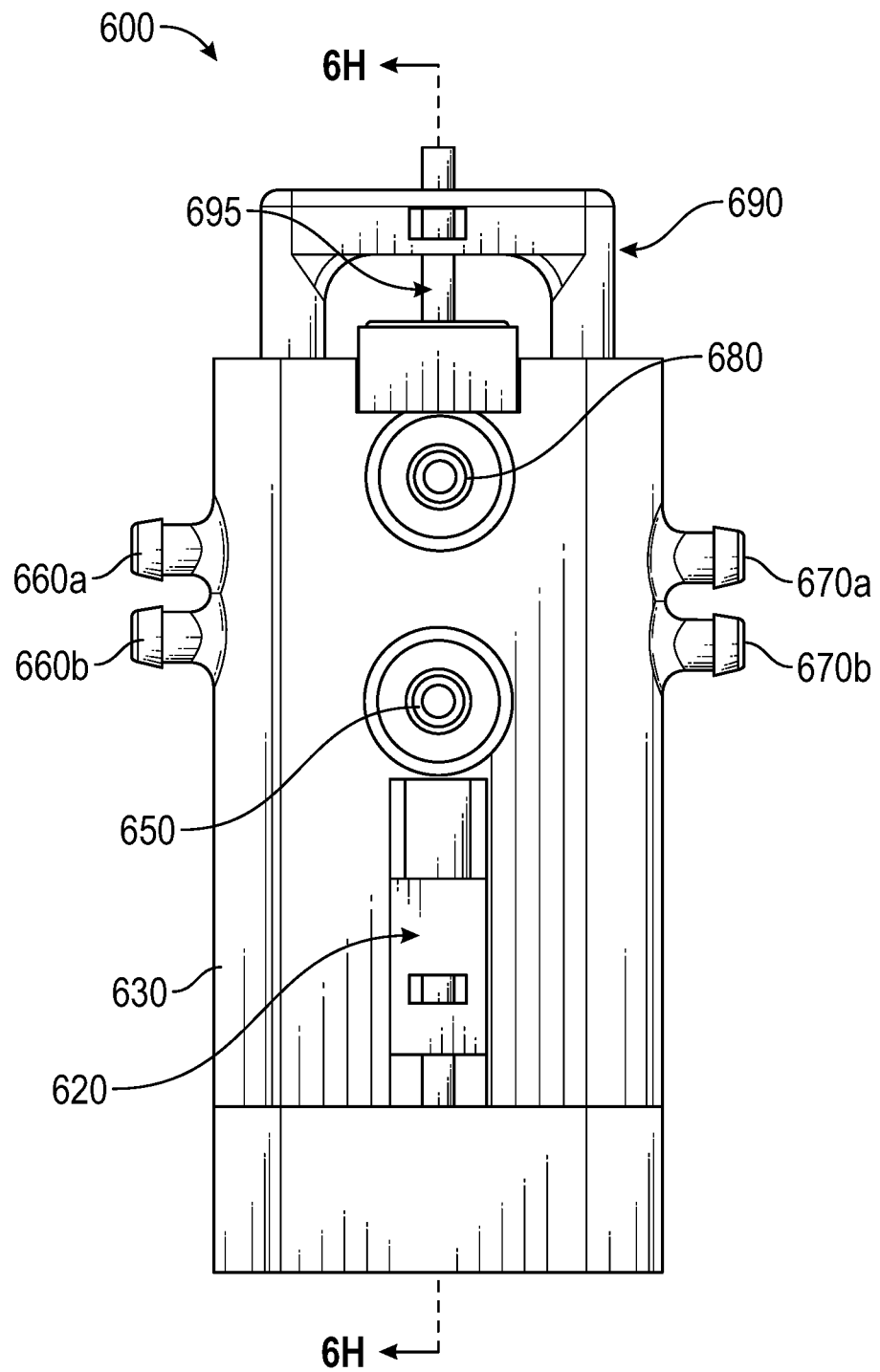
FIG. 6C is a rear view of the example valve module of FIG. 6A.
Figure 6D:
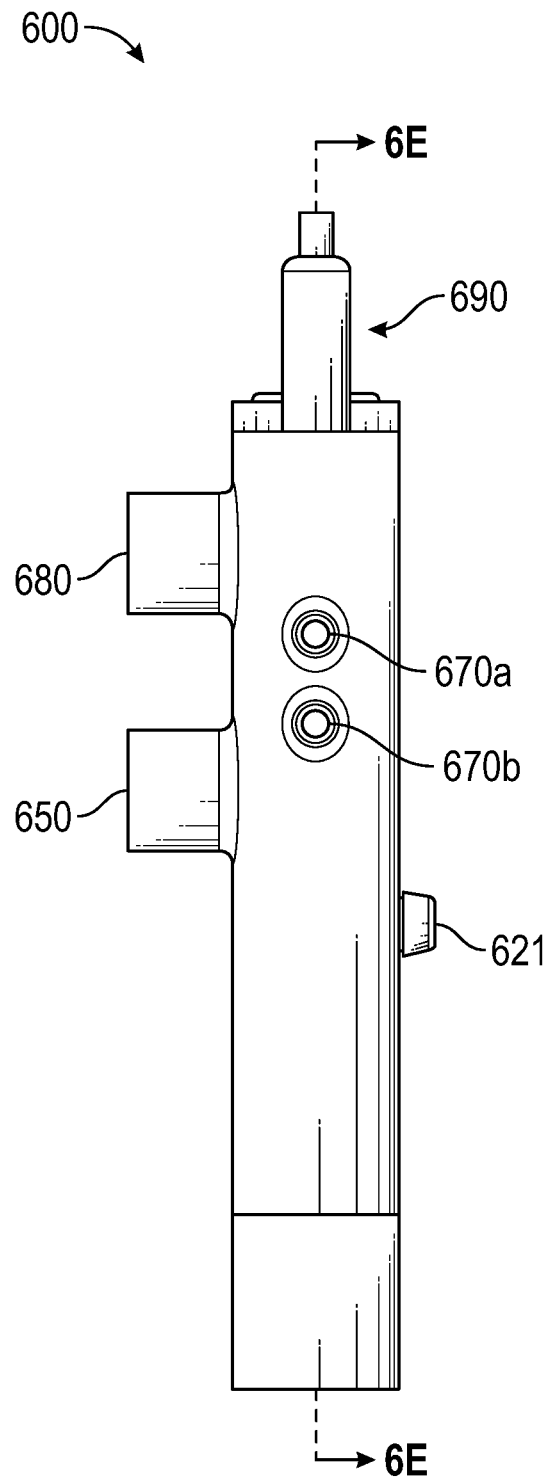
FIG. 6D is a side view of the example valve module of FIG. 6A.
Figure 6E:
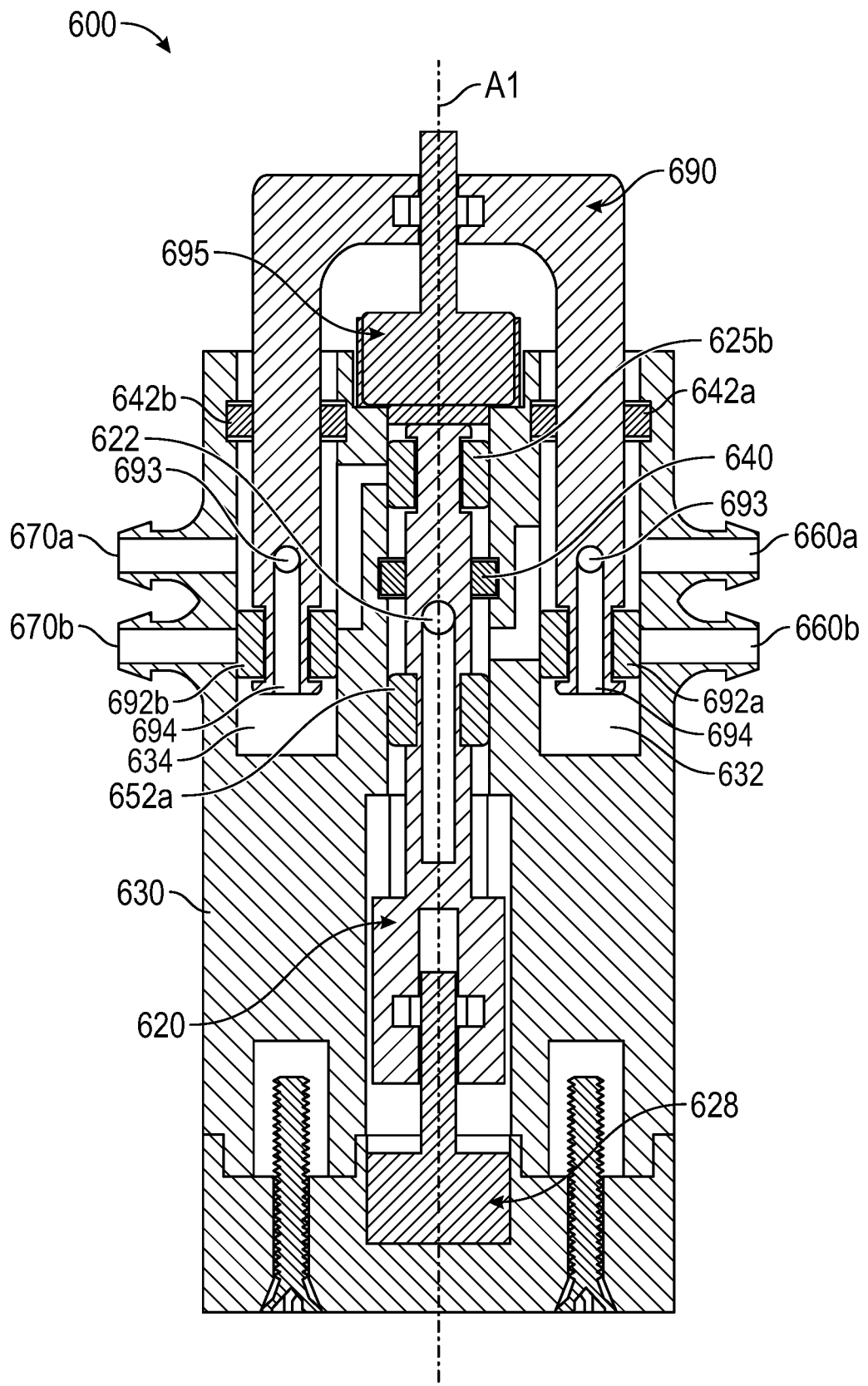
FIG. 6E is a front cross-sectional view of the example valve module of FIG. 6A in a first earpiece configuration.
Figure 6F:
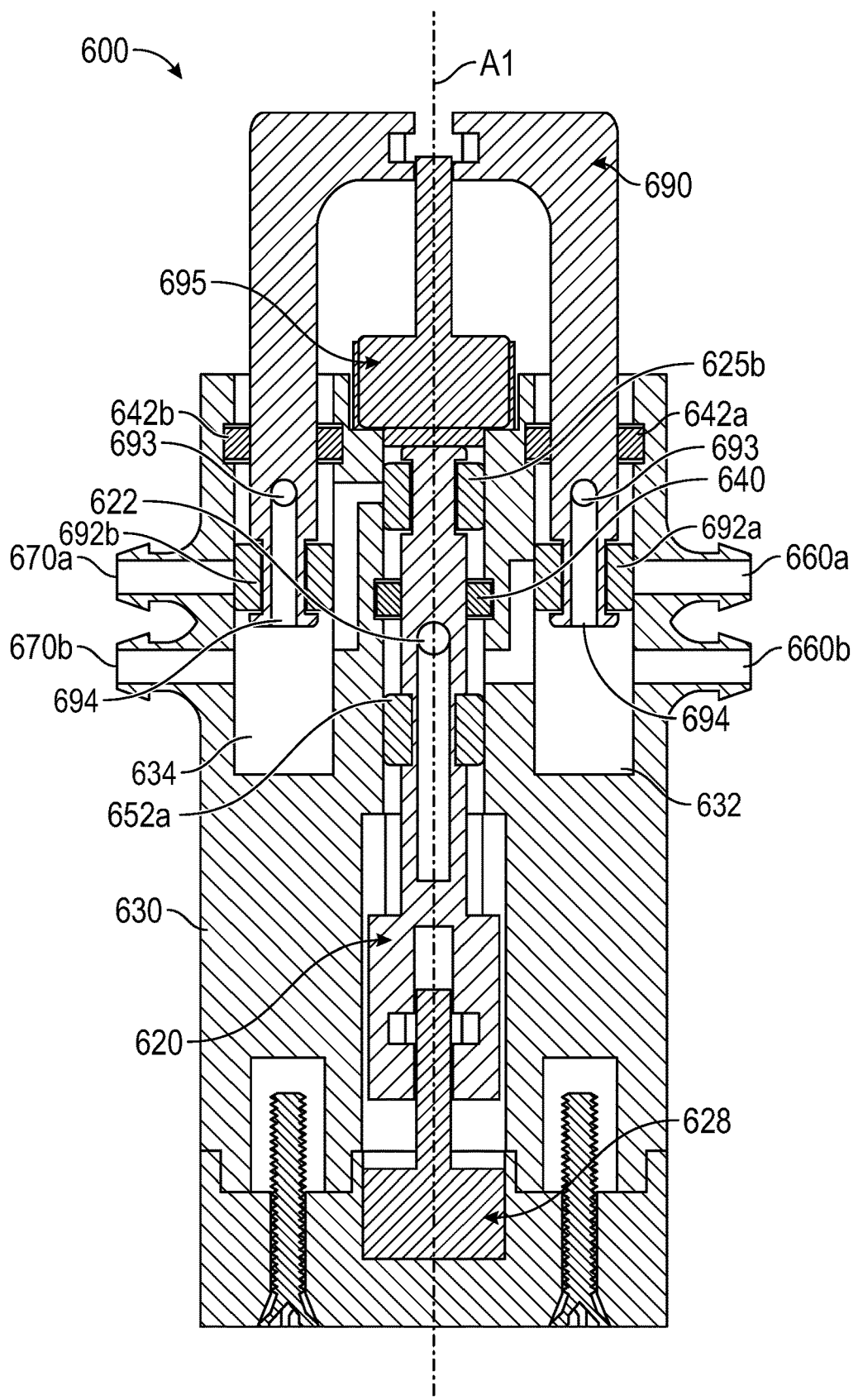
FIG. 6F is a front cross-sectional view of the example valve module of FIG. 6A in a second earpiece configuration.
Figure 6G:
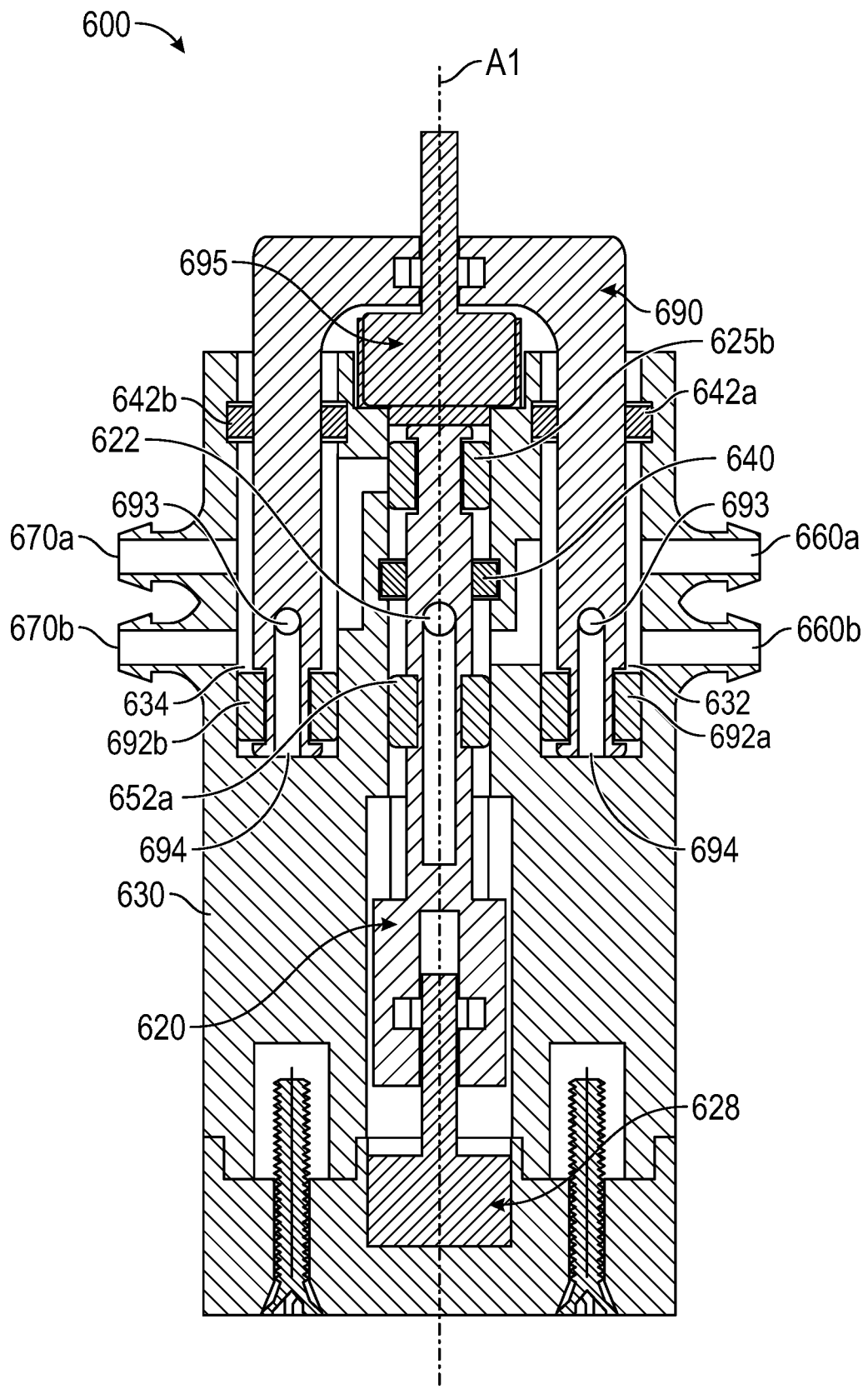
FIG. 6G is a front cross-sectional view of the example valve module of FIG. 6A in a first earpiece and a second earpiece configuration.
Figure 6H:
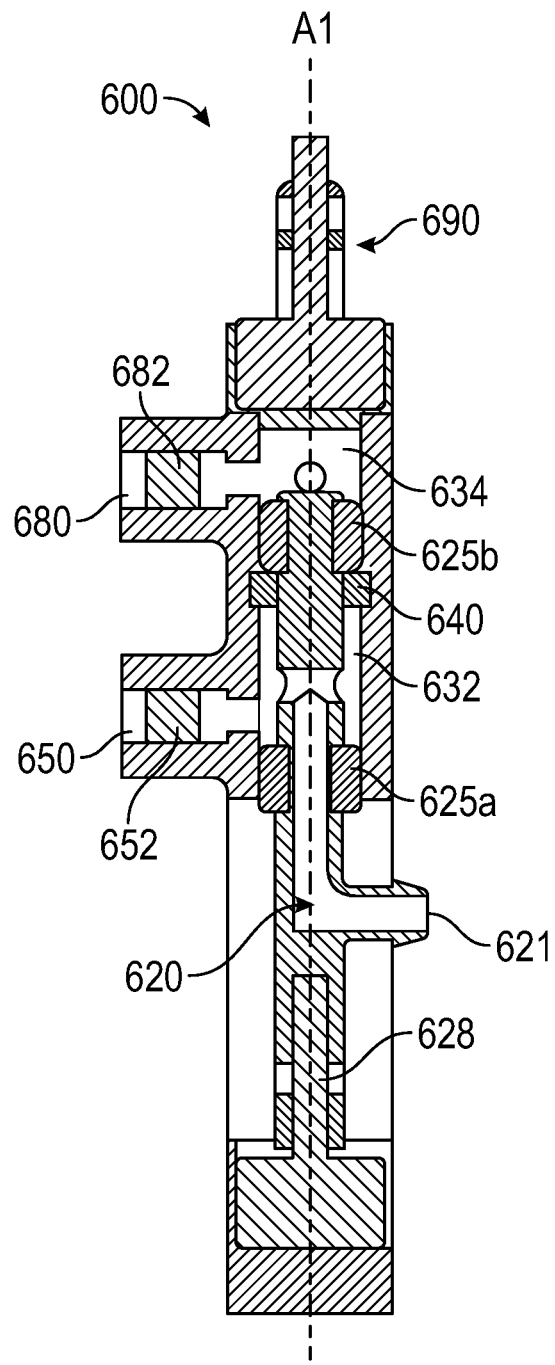
FIG. 6H is a side cross-sectional view of the example valve module of FIG. 6A in a caloric mode.
Figure 6I:
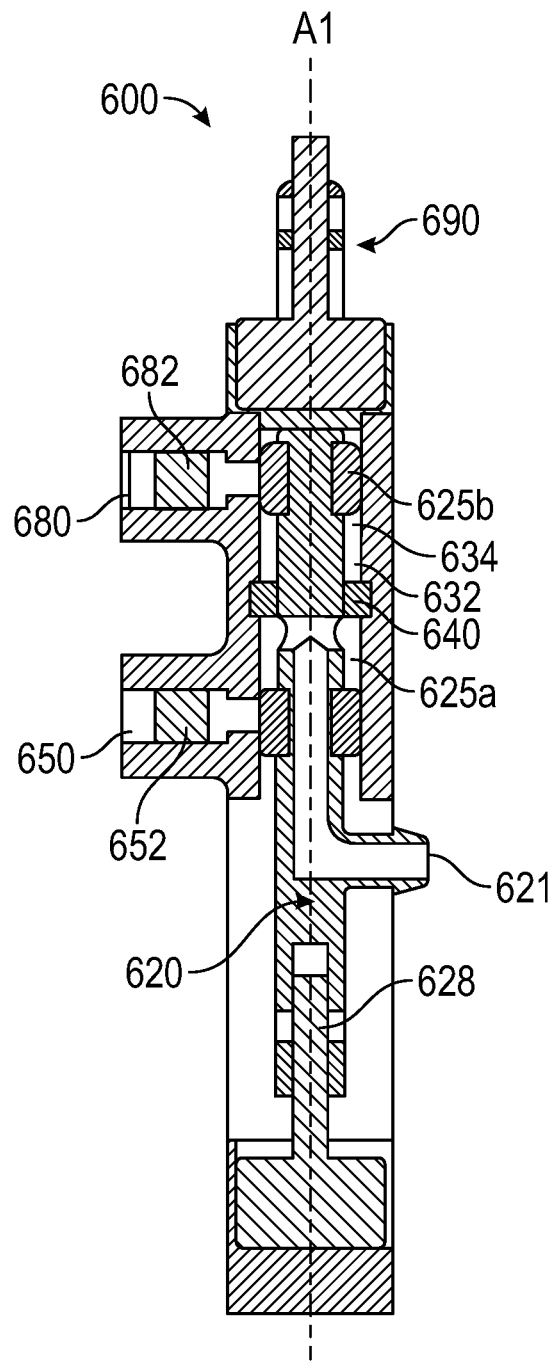
FIG. 6I is a side cross-sectional view of the example valve module of FIG. 6A in a pressure mode.

FIGS. 6A-6I are various views of a valve module 600, according to some embodiments. FIG. 6A is a front perspective view of a valve module 600; FIG. 6B is a front view of the valve module 600 of FIG. 6A with a housing 630 shown in a transparent view to illustrate various features within the housing 630. FIGS. 6C and 6D are rear and side views of the valve module 600 of FIG. 6A, respectively. FIGS. 6E-6G are front cross-sectional views of the valve module 600 of FIG. 6A in a first earpiece open configuration, a second earpiece open configuration, and a both earpieces open configuration, respectively. FIGS. 6H and 6I are side cross-sectional views of the valve module 600 of FIG. 6A in caloric mode and in pressure mode, respectively. Unless otherwise noted, the valve module 600 as shown in FIGS. 6A-6I may include components that are the same as or generally similar to the components in the remaining figures discussed herein. It will be understood that the valve module 600 shown in FIGS. 6A-6I can be used with any of the embodiments described and/or contemplated herein. It will also be understood that any of the embodiments described and/or contemplated herein can be modified to be used with the valve module 600 shown in FIGS. 6A-6I. Any feature, structure, material, method, or step that is described and/or illustrated in the embodiment of FIGS. 6A-6I can be used with and/or instead of any feature, structure, material, method, or step that is described and/or illustrated in any other embodiment of this specification.

The valve module 600 can include a movable member (e.g., a plunger) 620, an outer housing 630 separated into a first portion 632 and a second portion 634 via a housing plunger seal 640 (as shown in FIGS. 6B, 6E-6I), and a housing inlet conduit 650 and a housing outlet conduit 680 (as shown in FIGS. 6C, 6D, 6H, and 6I). As shown in the illustrated embodiment, the plunger 620 can be positioned at least partially within and/or supported by the housing 630. Similar to plunger 220 described herein with reference to FIGS. 5A and 5B, the plunger 620 can be configured to translate within the housing 630 along longitudinal axis A1 from a first position to a second position to selectively open and close one or more fluid pathways and to switch the treatment system between various operational modes (e.g., caloric mode and pressure mode). Unless otherwise noted herein, the various features of the plunger 620 (e.g., plunger inlet conduit 621, plunger outlet conduit 622, and plunger seals 625a, 625b) may interact with the various features of the housing 630 (e.g., housing plunger seal 640, housing inlet conduit 650, and housing outlet conduit 680) to selectively transition the valve module 600 between caloric mode and pressure mode, similar to the valve module 200 described herein with reference to FIGS. 5A and 5B. For example, when in a first position (e.g., caloric mode, as shown in FIG. 6H), the plunger seals 625a, 625b may be offset from the housing inlet conduit 650 and the housing outlet conduit 680, respectively, to permit fluid communication between an external atmosphere and the first portion 632 and second portion 634 of the housing 230, respectively. By way of another example, when in a second position (e.g. pressure mode, as shown in FIG. 6I), the plunger seals 625a, 625b may seal against the housing inlet conduit 650 and the housing outlet conduit 680, respectively, to inhibit fluid communication between an external atmosphere and the first portion 632 and second portion 634 of the housing 230, respectively.

In some embodiments, the valve module 600 may comprise a plunger actuator 628 configured to move the plunger 620 between the first and second positions. For example, the plunger actuator 628 may comprise a voice coil actuator (VCA) including a coil attached to a shaft configured to move the plunger 620 between the first and second positions. Any other suitable actuator can be used.

The valve module 600 may comprise two or more conduits configured to provide a fluid pathway towards one or more earpieces. The valve module 600 may comprise one or more earpiece outlet conduits 660a, 660b configured to channel fluid, such as air, from the first housing portion 632 towards one or more earpieces (not shown). The valve module 600 may comprise one or more earpiece inlet conduits 670a, 670b configured to intake or channel fluid from the one or more earpieces and into the second portion 634 of the housing 630. In some embodiments, when the valve module 600 is in fluid communication with a first and a second earpiece (e.g., a left and a right earpiece), the valve module 600 can include a first (e.g. left) earpiece outlet conduit 660a and a second (e.g., right) earpiece outlet conduit 660b that are each in fluid communication with their respective earpiece. In a similar manner, the valve module 600 can include a first (e.g., left) earpiece inlet conduit 670a and a second (e.g., right) earpiece inlet conduit 670b that are each in fluid communication with the respective earpiece. The valve module 600 may be configured to selectively open and/or close a fluid pathway through the various earpiece conduits to control a fluid flow to the first earpiece only, the second earpiece only, and/or both the first and second earpieces simultaneously. As such, the valve module 600 may control caloric and/or pressure treatment to one or both earpieces. For example, as will be discussed in further detail below, the various conduits can be selectively open and/or closed by a flow diverter 690 and corresponding fluid diverter seals 692a, 692b. In some embodiments, the valve module 600 can selectively close the fluid pathway to and/or from one or both of the earpieces.

As shown in the illustrated embodiment, the valve module 600 may comprise a flow diverter 690 positioned at least partially within and/or supported by one or more portions of the housing 630. The flow diverter 690 may comprise one or more flow diverter seals 692a, 692b. The flow diverter 690 and corresponding flow diverter seals 692a, 692b can be translated within the housing 630 along the longitudinal axis A1. Via translation of the flow diverter 630 relative to the housing 630, the flow diverter 690 and corresponding flow diverter seals 692a, 692b can open and/or close various fluid pathways to selectively control fluid flow to one or more earpieces.

The flow diverter 690, in some embodiments, may be configured to selectively open and close one or more fluid pathways (e.g., the earpiece outlet conduits 660a, 660b and/or the earpiece inlet conduits 670a, 670b) to transition caloric and/or pressure treatment between the first and second earpieces and, consequently, between a user's first (e.g. left) and second (e.g., right) ear, or both ears. The flow diverter 690 can be manipulated (e.g., manually by a user and/or automatically by a treatment device) to toggle the valve module 600 to apply the treatment to the first (e.g., left) earpiece via the first (e.g., left) earpiece outlet and inlet conduits 660a, 670a; to the second (e.g., right) earpiece via the second (e.g., right) earpiece outlet and inlet conduits 660b, 670b; and/or to both earpieces at the same time. In some embodiments, the flow diverter 690 can include one or more diverter sealing members 692a, 692b, such as an O-ring, positioned around an outer surface of the flow diverter 690. The diverter sealing members 692a, 692b can advantageously be positioned between the flow diverter 690 and the housing 630 to selectively open and/or close one of more fluid pathways between the first portion 632 and/or second portion 634 of the housing 230 and the earpieces.

With reference to FIG. 6E, the flow diverter 690 may be in a first position to open a fluid pathway to the first (e.g., left) earpiece and close a fluid pathway to the second (e.g., right) earpiece. When the flow diverter 690 is in the first position, the diverter sealing member 692a can be positioned at a location offset from the first earpiece outlet conduit 660a to permit fluid communication towards the first earpiece from the first portion 632 of the housing 630 via the first earpiece outlet conduit 660a. Additionally, when the flow diverter 690 is in the first position, the diverter sealing member 692a may be in a position against the second earpiece outlet conduit 660b to inhibit fluid communication towards the second (e.g., right) earpiece from the first portion 632 of the housing 630 through the second earpiece outlet conduit 660b. In a similar manner, the diverter sealing member 692b may be offset from the first earpiece inlet conduit 670a to permit fluid communication into the second portion 634 of the housing 630 from the first earpiece, while also being positioned against the second earpiece inlet conduit 670b to inhibit fluid communication into the second portion 634 of the housing 630 from the second earpiece.

With reference to FIG. 6F, the flow diverter 690 may be in a second position to open a fluid pathway to the second earpiece and close a fluid pathway to the first earpiece. When the flow diverter 690 is in the second position, the diverter sealing member 692a can be positioned at a location offset from the second earpiece outlet conduit 660b to permit fluid communication towards the second earpiece from the first portion 632 of the housing 630 via the second earpiece outlet conduit 660a. Additionally, when the flow diverter 690 is in the second position, the diverter sealing member 692a may be in a position against the first earpiece outlet conduit 660a to inhibit fluid communication towards the first earpiece from the first portion 632 of the housing 630 through the first earpiece outlet conduit 660a. In a similar manner, the diverter sealing member 692b may be offset from the second earpiece inlet conduit 670b to permit fluid communication into the second portion 634 of the housing 630 from the second earpiece, while also being positioned against the first earpiece inlet conduit 670a to inhibit fluid communication into the second portion 634 of the housing 630 from the first earpiece.

With reference to FIG. 6G, the flow diverter 690 may be in a third position to open a fluid pathway to both the first and second earpieces. When the flow diverter 690 is in the third position, the diverter sealing member 692a can be positioned at a location offset from both the first earpiece outlet conduit 660a and the second earpiece outlet conduit 660b to permit fluid communication towards both the first and second earpieces from the first portion 632 of the housing 630 via each of the first and second earpiece outlet conduits 660a, 660b, respectively. In a similar manner, the diverter sealing member 692b may be offset from both the first second earpiece inlet conduits 670a, 670b to permit fluid communication into the second portion 634 of the housing 630 from both the first and second earpieces.

In some embodiments, the valve module 600 can include one or more housing diverter seals 642a, 642b which can protrude from an inner surface of the housing 630 to engage with one or more portions of the flow diverter 690. The flow diverter 690, in some embodiments, can be received within the housing diverter seals 642a, 642b to form a friction and/or interference fit and to separate each of the first portion 632 and second portion 634 of the housing 630 from openings within the housing 630 configured to receive the flow diverter 690. The openings in the housing 630 can be in fluid communication with an external atmosphere. The friction and/or interference fit between the flow diverter 690 and the housing diverter seals 642a, 642b can be configured to prevent fluid flow between each of the two portions 632, 634 and the housing 630 openings, while permitting the flow diverter 690 to move with respect to the housing diverter seals 642a, 642b. The housing diverter seals 642a, 642b can each be affixed to the inner surface of the housing 630 to prevent each of the housing diverter seals 642a, 642b from moving with respect to the housing 630. The housing diverter seals 642a and 642b can be O-rings, or any other suitable type of seal.

In some embodiments, the valve module 600 may comprise a flow diverter actuator 695 configured to move the flow diverter 690 between the various positions. For example, the flow diverter actuator 695 may comprise a voice coil actuator (VCA) including a coil attached to a shaft configured to move the flow diverter 690 between the various positions. Any other suitable type of actuator can be used. An electronically controllable actuator can be used, or the flow diverter 690 can be moved manually, in some embodiments.

As shown in the illustrated embodiment and discussed herein, the valve module 600 may comprise two or more actuators configured to move one or more portions of the valve module 600. For example, the plunger actuator 628 can engage and move the plunger 620, while the flow diverter actuator 695 can engage and move the flow diverter 690. In some embodiments, each of the actuators may be activated independent of the other actuator. Accordingly, the plunger actuator 628 may be configured to move the plunger 620 between a first and a second position (i.e., transitioning a treatment system between caloric and pressure modes) independent of the flow diverter actuator 695 and/or the position of the flow diverter 690. In a similar manner, the flow diverter actuator 695 may be configured to move the flow diverter 690 between various positions (i.e., transitioning between a first earpiece, a second earpiece, and both earpiece configurations) independent of the plunger actuator 628 and/or the position of the plunger 620. As such, the valve module 600 may be configured to selectively provide any combination of caloric and/or pressure treatment to any individual earpiece and/or both earpieces simultaneously.

The flow diverter 690 can have a fluid pathway that extends through the flow diverter 690 between a first opening 693 on a first side of the fluid diverter seal 692a and a second opening 694 on a second side of the fluid diverter seal 692a. A similar fluid pathway can extend through the flow diverter 690 between a first opening 693 on a first side of the fluid diver seal 692b and a second opening 694 on a second side of the fluid diverter seal 692b. As the flow diverter 690 moves, fluid (e.g., air) can pass through the fluid pathway(s), for example, so that the flow diverter 690 does not compress the fluid (e.g., air) when it moves. When the flow diverter 690 moves towards the third position (shown in FIG. 6G), fluid can enter the second opening 694, pass through the fluid pathway, and exit the first opening 693. When the flow diverter 690 moves towards the second position (shown in FIG. 6F), fluid can enter the first opening 693, pass through the fluid pathway, and exit the second opening 694. As the flow diverter 690 moves, the fluid in the first portion 632 and/or the second portion 634 can pass through the flow diverter 690, which can impede a pressure differential from being formed between different areas in the first portion 632 and/or between different areas in the second portion 634. In some embodiments, the first opening 693 can be orthogonal to the second opening 694.

As shown in FIG. 6I, the valve module 600 can include a valve 652 configured to control fluid flow through the housing inlet conduit 650. The valve module 600 can include a valve 682 configured to control fluid flow through the housing outlet conduit 680. The valves 652 and/or 682 can be check valves, or selectively openable and closeable valves, such as similar to the valves 252 and 282 discussed herein. In some embodiments, the valve 652 can be configured to permit fluid flow into the valve module 600 through the housing inlet conduit 650, and can impede fluid flow out of the valve module 600 through the housing inlet conduit 650. The valve 682 can be configured to permit fluid flow out of the valve module 600 through the housing outlet conduit 680, and can impede fluid flow into the valve module 600 through the housing outlet conduit 680.

Examples of Valve Module with Multiple Solenoid for Caloric Treatment

Figure 7:
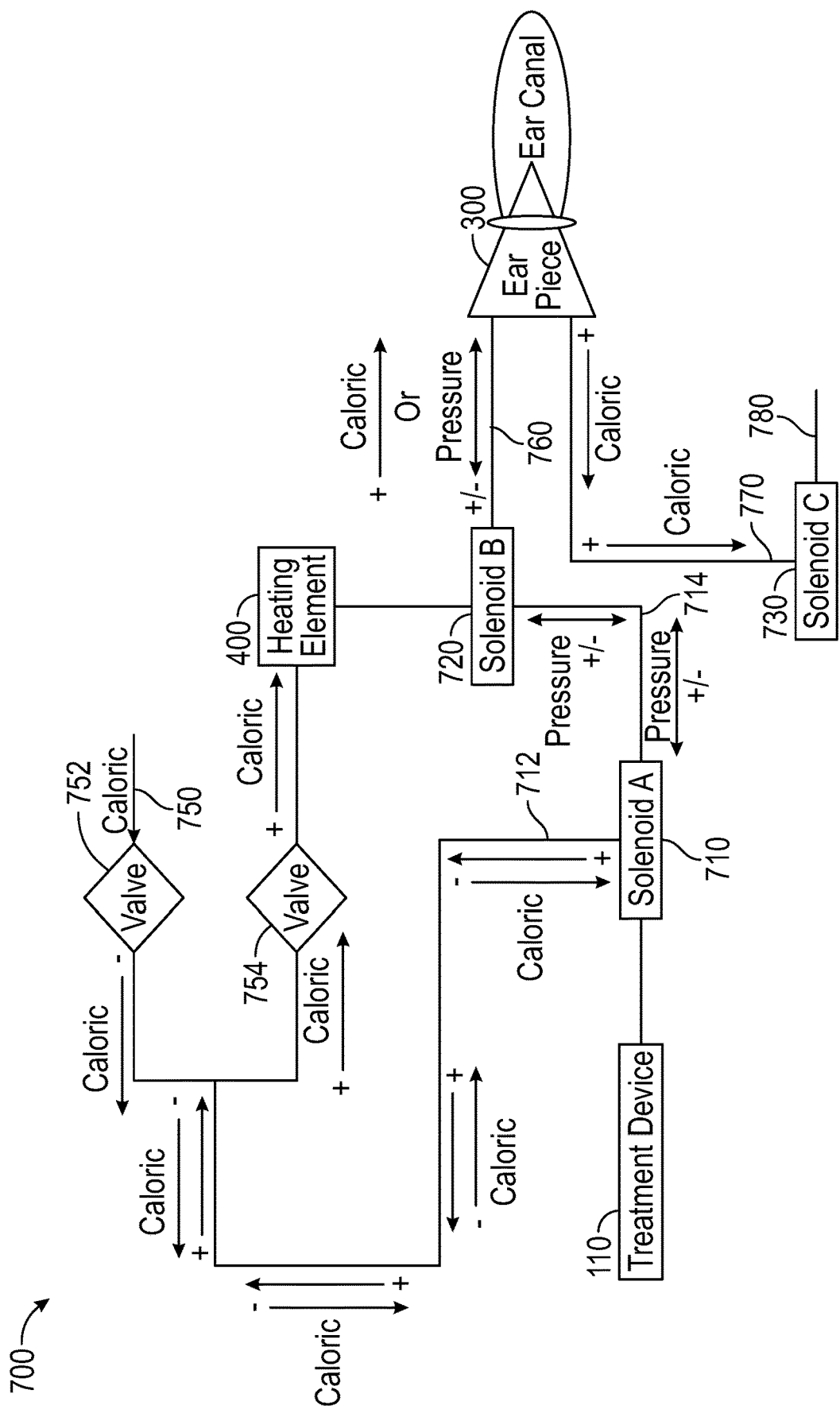
FIG. 7 illustrates a schematic drawing of an example treatment system.

FIG. 7 illustrates a schematic view of a treatment system 700, according to some embodiments. Unless otherwise noted, the treatment system 700 as shown in FIG. 7 may include components that are the same as or generally similar to the components in the remaining figures discussed herein. It will be understood that the treatment system 700 shown in FIG. 7 can be used with any of the embodiments described and/or contemplated herein. It will also be understood that any of the embodiments described and/or contemplated herein can be modified to be used with the treatment system 700 shown in FIG. 7. Any feature, structure, material, method, or step that is described and/or illustrated in the embodiment of FIG. 7 can be used with and/or instead of any feature, structure, material, method, or step that is described and/or illustrated in any other embodiment of this specification.

Similar to treatment system 100 described herein with reference to FIGS. 5A and 5B, FIG. 7 illustrates a schematic view of a treatment system 700 with a treatment device 110 in fluid communication with a valve system, a heating element 400 (although any temperature modifier can be used), and an earpiece 300. The valve system can include one or more solenoids, an inlet conduit 750, an earpiece outlet conduit 760, an earpiece inlet conduit 770, and an outlet conduit 780. The conduits can include tubes and/or openings, etc. In some embodiments, the treatment system 700 may comprise a housing (not shown) to support and/or protect one or more components of the treatment system 700. Unless otherwise noted herein, the various features of the treatment system 700 (e.g., an inlet conduit 750, valve 752 an earpiece outlet conduit 760, an earpiece inlet conduit 770, and an outlet conduit 780) may be used to intake, exhaust, and/or channel fluid, such as air, between an external atmosphere, various portions of the treatment system 700, and the earpiece 300, similar to the treatment system 100 described herein with reference to FIGS. 5A and 5B. For example, in some embodiments, the inlet conduit 750 can be used to intake or channel fluid from an external environment, and the valve 752 can be configured to allow fluid flow into the treatment system 700 from the external atmosphere and also be configured to inhibit fluid flow out of the treatment system 700 through the inlet conduit 750. By way of another example, in some embodiments, the outlet conduit 780 can be used to exhaust or channel fluid towards an external atmosphere. By way of further example, in some embodiments, the earpiece outlet conduit 760 can be used to export or channel fluid towards the earpiece 300, and the earpiece inlet conduit 270 can be used to intake or channel fluid from the earpiece 300.

In some embodiments, the treatment system 700 may comprise one or more solenoids 710, 720, 730 (or any other suitable type of valve) configured to open and/or close one or more fluid pathways and/or to selectively switch the treatment system 700 between various operational modes (e.g., caloric mode and pressure mode).

The treatment system 700 may include a heating element 400 positioned along a fluid pathway 712 between solenoid 710 and solenoid 720. The heating element 400 may comprise any structure described herein. In some embodiments, a cooling element, or any suitable temperature modifier can be used.

As shown in the illustrated embodiment, the treatment system 700 may include valve 754 in fluid communication with and configured to selectively control fluid flow within fluid pathway 712 between the solenoid 710 and the heating element 400. The valve 754, in some embodiments, can include a check valve or one-way valve configured to allow fluid flow towards heating element 400, such as from solenoid 710 and also configured to inhibit fluid flow in an opposite direction.

The treatment device 110 may apply a fluid flow from the treatment device 110 to apply a caloric treatment when the treatment system 700 is in caloric mode. The solenoid 710, when in caloric mode, can be configured to allow the fluid to flow through solenoid 710 into caloric fluid pathway 712. As the fluid enters the caloric fluid pathway 712, the valve 752 may prevent the fluid from exiting into the external atmosphere through the inlet conduit 750, as described herein. Accordingly, the fluid can be directed to through the valve 754 towards the heating element 400 and the solenoid 720. As the fluid flows through the above-described fluid pathway, the heating element 400 can heat the fluid before it passes through earpiece inserted in a user's ear canal. The fluid temperature may be raised as the fluid interacts with the heating element 400. In other embodiments, a cooling element, or any suitable temperature modifier can be used. The solenoid 720, when in caloric mode, can be configured to allow the heated fluid to flow from the caloric fluid pathway 712 through solenoid 720 into the earpiece outlet conduit 760 towards the earpiece 300. The heated fluid may then enter the earpiece 300, and consequently, the ear canal of a user to affect the internal temperature of the user's ear canal. The fluid may then exit the earpiece 300 and enter the solenoid 730 through the earpiece inlet conduit 770. The solenoid 730, when in caloric mode, may be configured to allow the fluid to exit to an external atmosphere through the outlet conduit 780.

In some instances, the treatment device 110 may draw in fluid from the external atmosphere. The treatment device 110 may obtain external fluid by applying a negative pressure fluid flow. The decrease in pressure within the treatment system 700 can cause fluid to flow towards the solenoid 710 through the inlet conduit 750 and the valve 752. As described herein, in some embodiments, the valve 752 may comprise a one-way valve that permits fluid to flow into the treatment system 700 but prevents fluid flow towards an external atmosphere through the inlet conduit 750. The treatment device 110 can perform negative and positive pressure pumping stages to advance fluid through valve 752, through valve 754, through the caloric fluid pathway 712, through the valve (e.g., solenoid) 720, through the earpiece outlet conduit 760, through the earpiece 300, through the earpiece inlet conduit 770, through the valve (e.g., solenoid) 730, and to the external environment.

In some embodiments, as discussed herein, the solenoid 730, when in caloric mode, may be configured to permits fluid to flow out towards an external atmosphere. In some cases, the valve (e.g., solenoid) 730 can prevent fluid flow into the treatment system 700 through the out conduit 780. The one-way nature of the solenoid 730, in this configuration, can inhibit a fluid from flowing through the outlet conduit 780 and/or the earpiece 300 when the treatment device 110 applies a negative pressure to fill an internal chamber with fluid, as described above. In some embodiments, when in caloric mode, the valve (e.g., solenoid) 730 can be open when in a positive pressure pumping stage, so that fluid (e.g., air) can be exhausted out through outlet conduit 780. When in caloric mode, the valve (e.g., solenoid) 730 can be closed during a negative pressure pumping stage, which can impede fluid from being drawn in through the outlet conduit 780, and can facilitate the entry of fluid through the inlet conduit 750. In some embodiments, the valve (e.g., solenoid) 730 can be open when in caloric mode, and the system 700 can include a check valve (not shown in FIG. 7) that permits fluid to exit through the outlet conduit 780 while impeding fluid from entering through the fluid conduit 780.

With continued reference to FIG. 7, the valves (e.g., solenoids) 710, 720, 730 can be reconfigured to transition the treatment system 700 to pressure mode. The solenoid 710, 720, 730 can be advantageously altered to selectively open and/or close one of more fluid pathways within the treatment system 700. For example, when the treatment system 700 is in caloric mode, the solenoid 710 may open caloric fluid pathway 712 and close pressure fluid pathway 714, such as to permit fluid communication between the treatment system 700 and the external environment through the inlet conduit 750. When the treatment system 700 is in pressure mode, the solenoid 710 may close caloric fluid pathway 712 and open pressure fluid pathway 714. In a similar manner, the solenoid 720, when in pressure mode, may also close caloric fluid pathway 712 and open pressure fluid pathway 714 to be in fluid communication with the earpiece outlet conduit 760. When in caloric mode, the solenoid 720 can open the caloric fluid pathway 712 and close the pressure fluid pathway 714. Accordingly, a fluid flowing through the treatment system 700 from treatment device 710 may bypass the caloric fluid pathway 712 that passes through heating element 400 when the treatment system 700 is in pressure mode. When in pressure mode, the solenoid 730 can close the outlet pathway 780, for example so that pressure can be applied to the ear.

The treatment device 110, when the treatment system 700 is in pressure mode, may apply a positive and/or negative pressure fluid flow from the treatment device 110. When the treatment device 110 applies positive pressure when in pressure mode, the fluid may flow through solenoid 710, into pressure fluid pathway 714, through solenoid 720, and towards the earpiece 300 through earpiece outlet conduit 760. In some embodiments, when in pressure mode, the fluid can be prevented from exiting the earpiece 300, and ultimately the treatment system 700, through the earpiece inlet conduit 270 as the solenoid 730 may be reconfigured to close the outlet conduit 780. Accordingly, the solenoid 730 may cause fluid, and consequently pressure, to build up within the earpiece 300 and the external ear canal of a user. The treatment system 110 can be configured to apply a sufficient amount of pressure increase according to a desired treatment profile.

With continued reference to the illustrated embodiment of FIG. 7, when the treatment device 110 applies negative pressure when in pressure mode, fluid may be drawn away from the earpiece 300 and the ear canal of a user to apply a negative pressure treatment to a user. The application of negative pressure by the treatment device 110 may cause fluid to flow through the solenoid 710 from pressure fluid pathway 714. As the fluid flows out of pressure fluid pathway 714, fluid can be prevented from entering the treatment system through the inlet conduit 750 by solenoids 710, 720 to prevent the external fluid from equalizing the pressure differential. Accordingly, the configuration of solenoids 710, 720, when in pressure mode, may cause fluid to flow out of the earpiece 300 and the external ear canal of a user through the earpiece outlet conduit 760 upon the application of a negative pressure fluid flow by the treatment device 110. Consequently, the pressure within the earpiece 300 and the ear canal of a user will decrease. The treatment system 110 can be configured to apply a sufficient amount of pressure decrease according to a desired treatment profile.

Valve Module Examples

Figure 8:
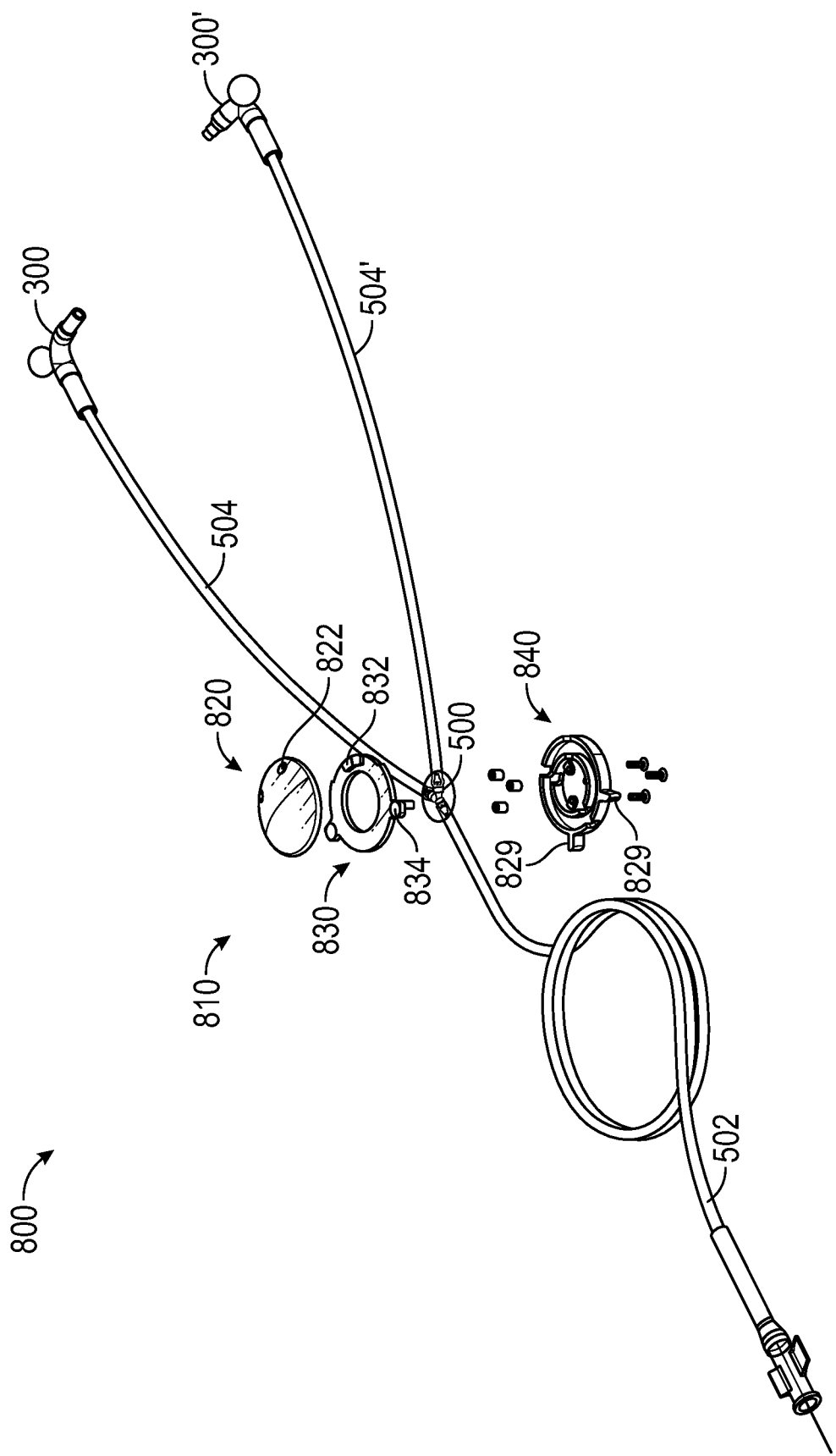
FIG. 8 is a front perspective exploded view of an example treatment system having a valve module in fluid communication with other systems and devices.

In various embodiments discussed herein, caloric and/or pressure treatment can be transitioned between the user's ears. If the treatment system 800 has a single earpiece, the user can be provided with an instruction to move the earpiece from one ear to the other side. With reference to FIGS. 8-9C, if the treatment system 800 has two earpieces 300, 300' (e.g., a left earpiece and a right earpiece) and a valve module 810, the user can be provided with an instruction to toggle the valve module 810 to apply the treatment to a first (e.g., left) earpiece 300, a second (e.g., right) earpiece 300', and/or both earpieces 300, 300' at the same time. Similarly, in various embodiments discussed herein, the treatment system 800 can select whether to provide treatment to the right ear, the left ear, or both simultaneously.

Figure 9A:
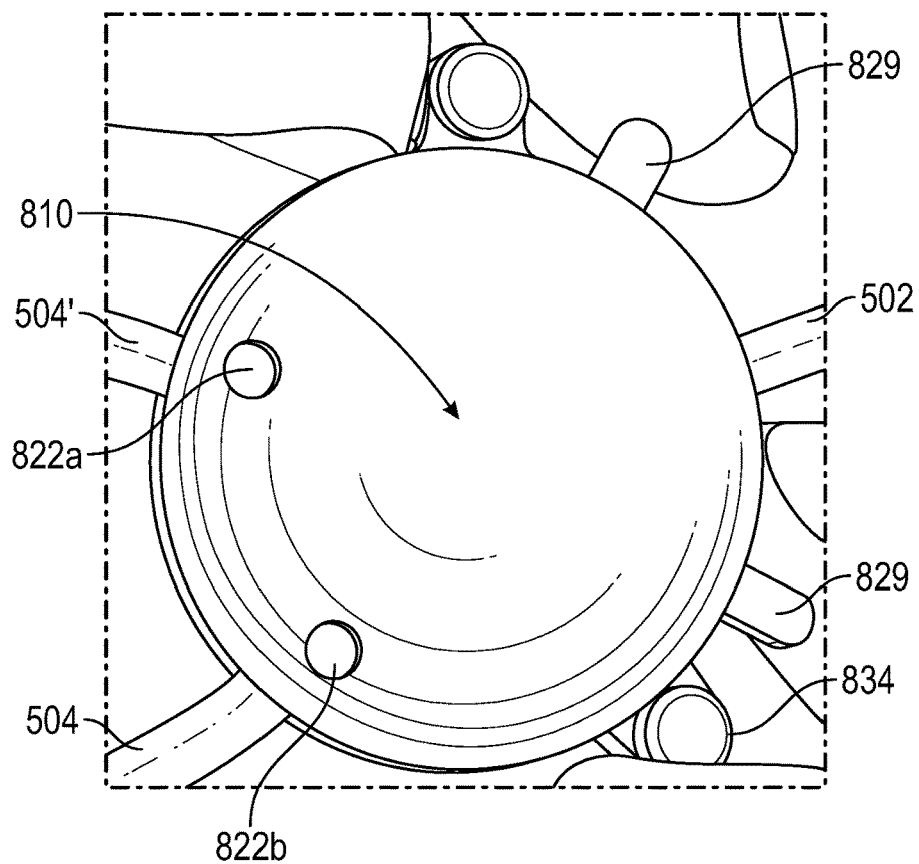
FIG. 9A is a front view of the example valve module of FIG. 8 in a first earpiece and a second earpiece open configuration.
Figure 9B:
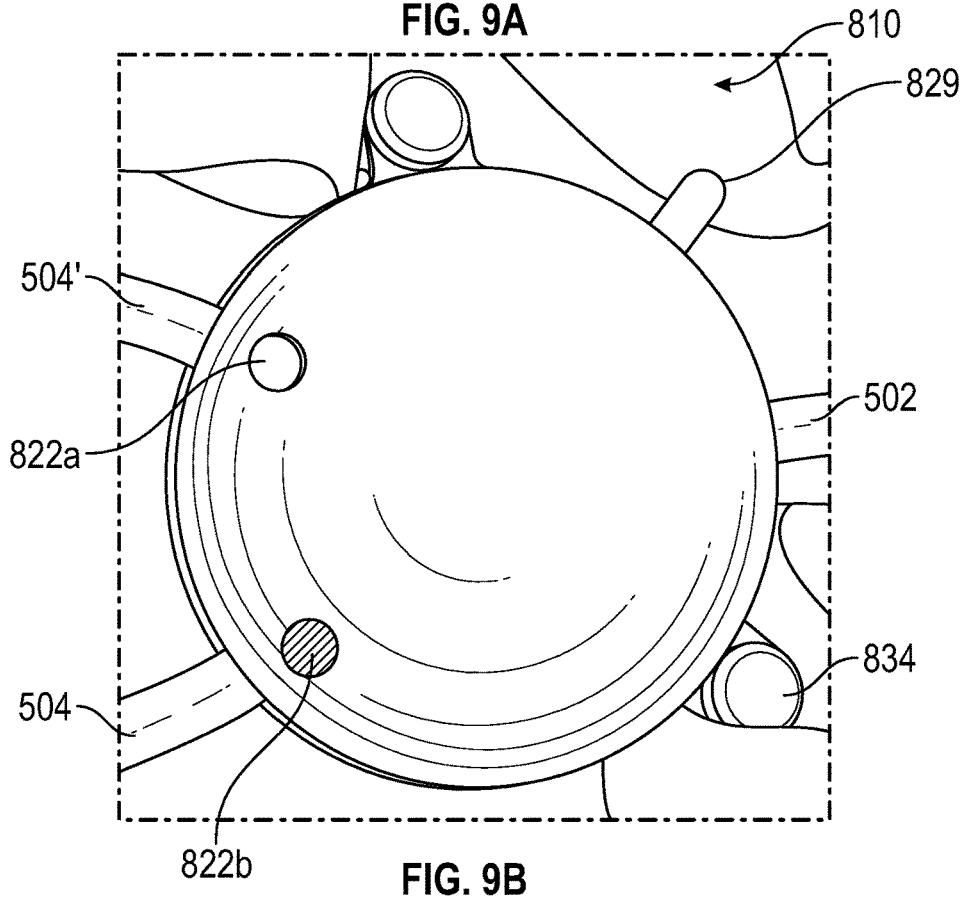
FIG. 9B is a front view of the example valve module of FIG. 8 in a first earpiece open configuration.
Figure 9C:
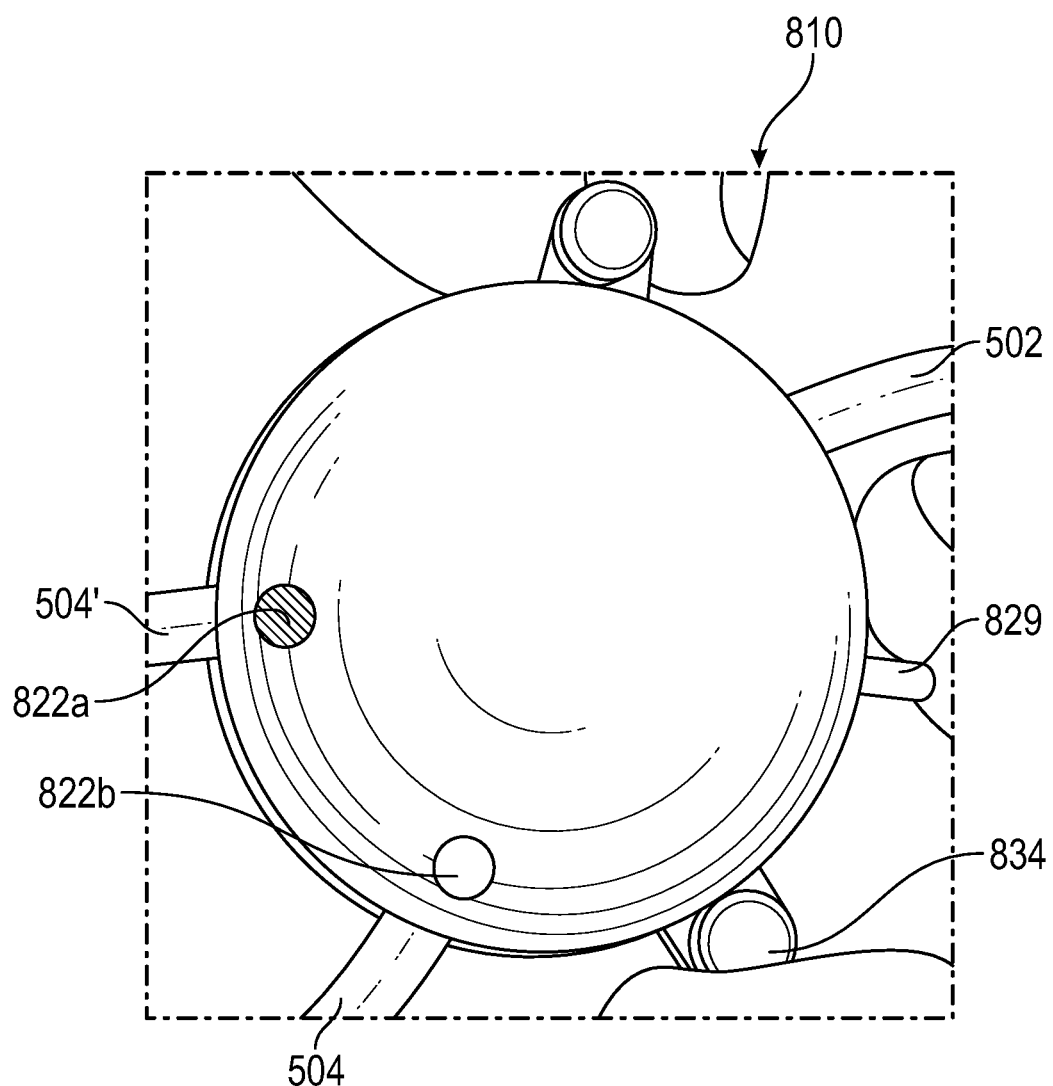
FIG. 9C is a front view of the example valve module of FIG. 8 in a second earpiece open configuration.

FIGS. 8-9C are various views of a valve module 810, according to some embodiments. In particular, FIG. 8 is an exploded view of a treatment system 800 including a valve module 810, and FIGS. 9A-9C are various front views of the valve module 810 of FIG. 8 illustrating various configurations of the valve module 810. Unless otherwise noted, the valve module 810 as shown in FIGS. 8-9C may include components that are the same as or generally similar to the components in the remaining figures discussed herein. It will be understood that the valve module 810 shown in FIGS. 8-9C can be used with any of the embodiments described and/or contemplated herein. It will also be understood that any of the embodiments described and/or contemplated herein can be modified to be used with the valve module 810 shown in FIGS. 8-9C. Any feature, structure, material, method, or step that is described and/or illustrated in the embodiment of FIGS. 8-9C can be used with and/or instead of any feature, structure, material, method, or step that is described and/or illustrated in any other embodiment of this specification.

As illustrated in FIG. 8, the valve module 810 may reside at a location along the tubing 500, external to the treatment device. For example, the tubing 500 may comprise a treatment device fluid pathway 502 connected to the treatment device and then split into two earpiece fluid pathways 504, 504' at the connection site with the valve module 810. Each of the two earpiece fluid pathways 504, 504' may be connected to a particular earpiece 300, 300' and may be selectively opened and closed by the valve module 810. However, while the valve module 810 is illustrated in FIG. 8 as residing outside of the housing of the treatment device, it will be understood by one of ordinary skill in the art that the valve module 810 may be located within a housing of the treatment device. For example, the valve module 810 may be connected to an outlet with the two earpiece fluid pathways 504, 504' extending therefrom.

In some embodiments, to selectively control the flow of fluid into the one or more earpieces 300, 300', the valve module 810 may comprise a switch or actuator 830. The actuator 830, in some instances, may comprise multiple positions configured to selectively open and/or close the earpiece fluid pathways 504, 504' of the tubing 500. The actuator 830 can be manipulated by the user to transition the valve module 810 between the first earpiece 300 open configuration (as shown in FIG. 9B), the second earpiece 300' open configuration (as shown in FIG. 9C), and in some cases, to the both earpieces 300, 300' closed configuration (as shown in FIG. 9A), or the both earpieces 300, 300' open configuration. In this manner, the actuator 830 may function as a rotatable valve.

The actuator 830 can be designed to be positioned between a cover 820 and a housing 840. Accordingly, the actuator 830 can cooperate with one or more portions of the cover 820 and/or housing 840 to selectively control fluid flow into one or more of the earpieces 300, 300' to form the valve module 810. The housing 840 may be designed to receive and support the actuator 830 of the valve module 810. The actuator 830 can be secured between the cover 820 and the housing 840. In some embodiments, the placement of the actuator 830 between the cover 820 and the housing 840 can define one or more corresponding fluid pathway tubing channels between the actuator 830 and the housing 840. In some embodiments, the tubing channels can be selectively sealed to control the flow of fluid through the earpiece fluid pathways 504, 504' to the one or more earpieces 300, 300'.

As shown in FIG. 8, the housing 840 can include one or more recesses and/or channels formed along an interior of the housing 840. The channels can be designed to receive and support the treatment device fluid pathway 502; the earpiece fluid pathways 504, 504'; and/or a tubing 500 intersection of the earpiece fluid pathways 504, 504'. In some embodiments, the channels are larger than the tubing that the channels are designed to receive. The channels, in some embodiments, can include three or more channels configured to receive the treatment device fluid pathway 502, the first earpiece fluid pathway 504, and the second earpiece fluid pathway 504'.

The various channels of the housing 840 can cooperate with the actuator 830 to selectively open and close one or more of the channels to selectively control fluid passage into one or more earpieces 300, 300'. For example, the actuator 830 may comprise one or more corresponding structures (e.g., protrusions and/or ridges) configured to interact with and selectively open and close the housing channels. In some embodiments, the actuator 830 can comprise a ridge (not shown) on a rear-side of the actuator 830. The ridge may be configured to pinch and/or close off one or more portions of the tubing 500 corresponding to an earpiece fluid pathway 504, 504' residing within the channels of the housing as the actuator 830 is rotated within the valve module 810.

As shown in the illustrated embodiment, the cover 820 can include one or more indexing features, such as aperture 822, which can be matched to corresponding indexing features on another component, such as an indicator 832 of the actuator 830. The combination of the aperture 822 and the indicator 832 may permit the valve module 810 to provide a visual indication to the user as to the current configuration of the valve module 810 (i.e., which earpiece fluid pathway 504, 504' is open and configured to apply pressure and/or caloric treatment). In some embodiments, as described above, a user may manipulate (e.g. rotate) the actuator 830 to one or more configurations by moving one or more actuator tabs 834. As a user manipulates the actuator tabs 834, for example, the indicator 834 of the actuator 830 may align with a corresponding aperture 822a, 822b on the cover 820 to provide a visual indication to a user through the apertures 822a, 822b. In some embodiments, a colored icon can align with one or more of the apertures 822a, 822b to indicate that a particular corresponding fluid pathway 504, 504' is open and treatment will be applied to the corresponding earpiece 300, 300'. As illustrated in FIGS. 9A-9C, the valve module 810 may indicate that both fluid pathways 504, 504' are closed or that both fluid pathways 504, 504' are open (as shown in FIG. 9A), that only a first earpiece fluid pathway 504 is open (as shown in FIG. 9B), or that only a second earpiece fluid pathway 504' is open (as shown in FIG. 9C).

The housing 840 can have one or more indexing features (e.g., housing tabs 829) sized and shaped to receive or align with corresponding indexing features of the actuator 830, such as actuator tabs 834 of the actuator 830. The positioning of the actuator tabs 830 and the indexing features (e.g., housing tabs 829) of the housing 840 can align the actuator 830 in the proper orientation and alignment when positioned in the housing 840. Proper placement of the actuator 830 can enable the actuator 830 to be able to properly control fluid flow within the various fluid pathways 502, 504, 504' and that the apertures 822 of the cover 820 to identify the appropriate indicator 822 of the actuator 830 when in the various valve configurations.

The user can pinch the actuator tab 834 and the housing tab 829 together on a first side to transition the valve module 810 to open the fluid pathway 504, as shown in FIG. 9B. The user can pinch the actuator tab 834 and the housing tab 829 together on a second side to transition the valve module 810 to open the other fluid pathway 504'.

Diaphragm Examples

Figure 10A:
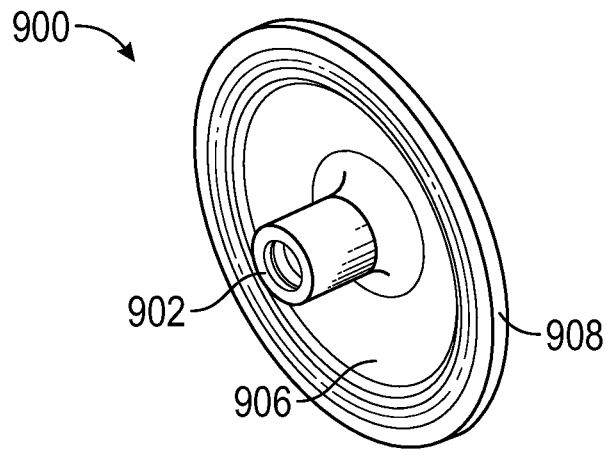
FIG. 10A illustrates a front perspective view of an example diaphragm.
Figure 10B:
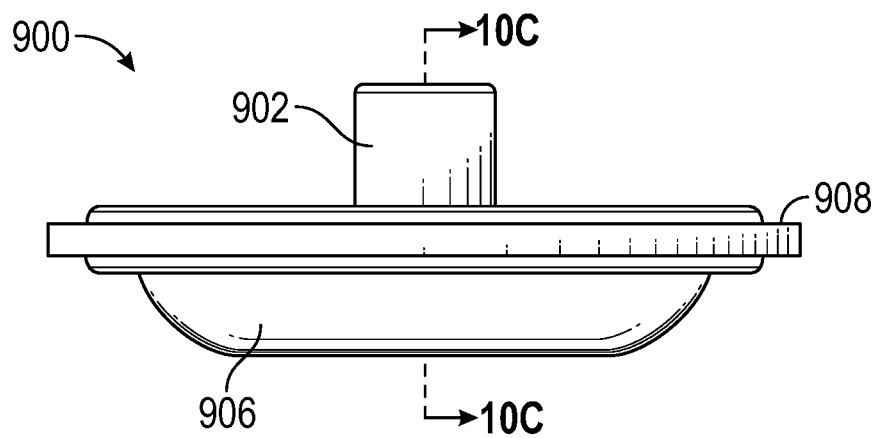
FIG. 10B is a side view of the example diaphragm of FIG. 13A.
Figure 10C:
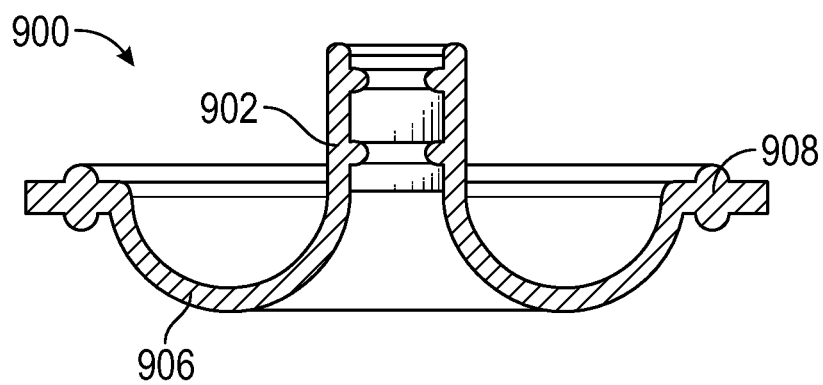
FIG. 10C illustrates a side cross-sectional view of the example diaphragm of FIG. 13A.

FIGS. 10A-10C are various views of an embodiment of a diaphragm 900 which can form part of the treatment device. In particular, FIG. 10A is a front perspective view of a diaphragm 900 and FIGS. 10B and 10C are side and side cross-sectional views of the diaphragm 900 of FIG. 10A, respectively. Unless otherwise noted, the diaphragm 900 as shown in FIGS. 10A-10C can be used with any of the embodiments described and/or contemplated herein. It will also be understood that any of the embodiments described and/or contemplated herein can be modified to be used with the diaphragm 900 shown in FIGS. 10A-10C. For example, diaphragm 1113 as illustrated in FIG. 1 may comprise diaphragm 900 of FIGS. 10A-10C.

As shown in the illustrated embodiment, the diaphragm 900 can include An inner connection portion 902, a body portion 906, and a peripheral connection portion 908. In some embodiments, the inner connection portion 902 can be positioned generally along an axial centerline of the diaphragm 900 such that the inner connection portion 902 is generally centered on the diaphragm 900. The inner connection portion 902 can include an engagement mechanism or portion, such as a recess into which another component, such as a shaft, can be inserted. In some embodiments, diaphragm 900 can be designed to help reduce the amount of power required to operate a pressure generator or pump and/or reduce the amount of stress applied to the diaphragm 900.

As shown in the illustrated embodiment, the diaphragm can include a body portion 906, such as in the form of a generally annular body. A peripheral or outer connection portion 908 can be disposed radially outward of the body portion 906. The outer connection portion 908 can include an engagement mechanism or portion that can be configured to attach to a component such as a housing or wall of a pressure chamber. The outer connection portion 908 of the diaphragm 900 can include a lip extending from an outer portion of the body portion 906. The lip can be formed integrally with the body portion 906. The lip may comprise increased thickness relative to the body portion 906. The lip may be configured to improve the attachment of the peripheral attachment portion 908 of the diaphragm to the remainder of the pressure generator.

The body portion 906 can be sized and shaped to allow the connection portion 902 to move relative to the peripheral connection portion 908 to allow an interior volume of the diaphragm 900 to be altered. For example, an actuator can move a component that is coupled to inner connection portion 902 and/or an actuator can move a component that is coupled to the outer connection portion 908. In some embodiments, the body portion 906 can be made out of a resilient material having a suitable modulus of elasticity. This can allow the body portion 906 to temporarily deform in response to forces exerted on the body portion 906. In some embodiments, the body portion 906 can be designed with excess material to allow for relative movement between the inner connection portion 902 and the peripheral portion 904. For example, as shown in the illustrated embodiment, the body portion 906 can have a generally toroidal configuration and takes on a curved shape in an initial configuration. The body portion 906 can substantially conform to a portion of a toroid shape. Should the inner connection portion 902 be moved away from the peripheral connection portion 908, the body portion 906 can deform (e.g., straighten) to some degree, such as via loss of slack in the body portion 906. This can beneficially enhance the longevity of the diaphragm 900 (which can be subjected to constant and cyclical motion) by reducing an amount of stress placed on the outer connection portion 908 and/or the remainder of the diaphragm 900 relative to a diaphragm that may not include a body portion that contains a toroidal shape. This can reduce the strain at the junction between the body portion 906 and the inner connection portion 902 and/or the junction between the body portion 906 and the outer connection portion 908, which can in turn reduce fatigue and decrease the likelihood of the diaphragm 900 breaking. In some embodiments, the diaphragm 900 can be made from polymers such as rubbers, silicon, or the like, or a combination of materials. The toroidal shape of the body portion can provide increased fluid flow, less energy consumption, and/or less stress on the diaphragm. The inner connection portion 902, the body portion 906, and the outer connection portion 908 can be integrally formed.

Earpiece Examples

Figure 11A:
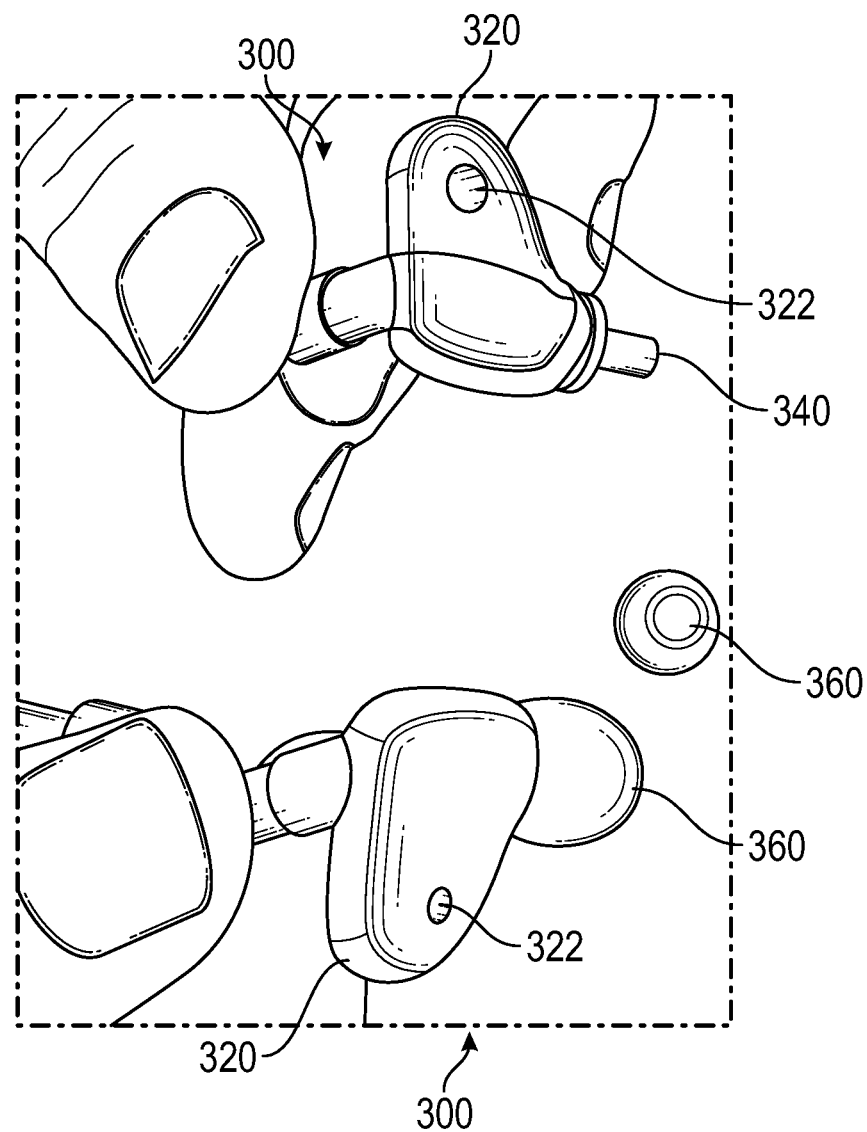
FIG. 11A is a rear perspective view of an example earpiece.
Figure 11B:
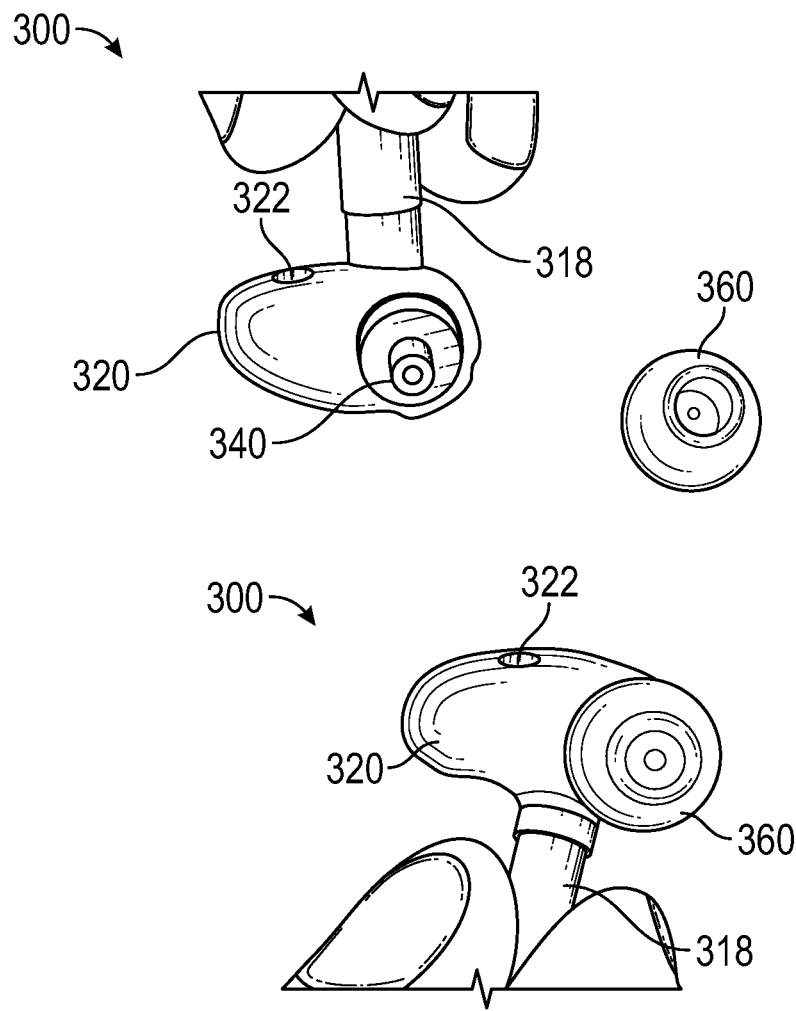
FIG. 11B is a front view of the example earpiece of FIG. 10A.
Figure 12A:
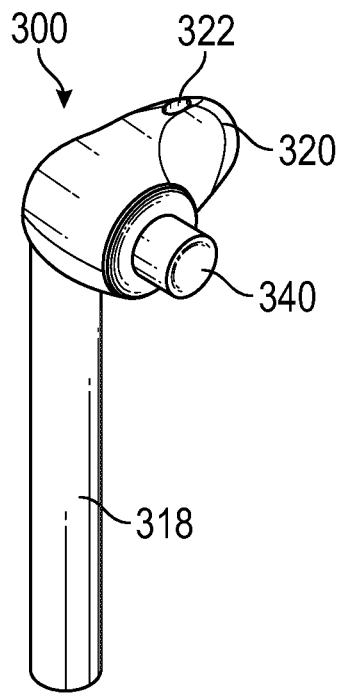
FIG. 12A illustrates a front perspective view of the example earpiece of FIG. 10A.
Figure 12B:
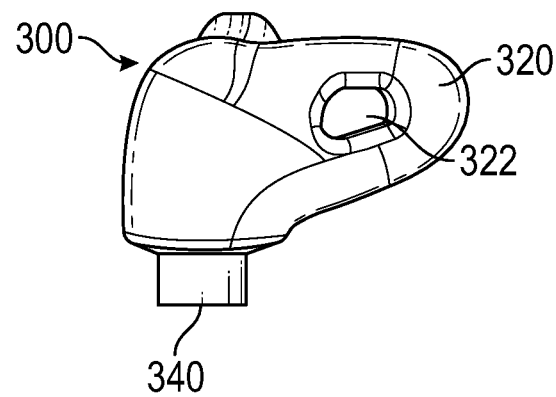
FIG. 12B illustrates a top view of the example earpiece of FIG. 10A.
Figure 12C:
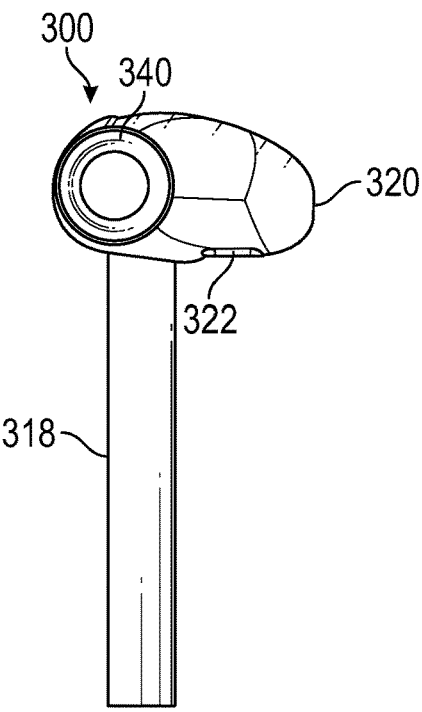
FIG. 12C illustrates a front view of the example earpiece of FIG. 10A.
Figure 13:
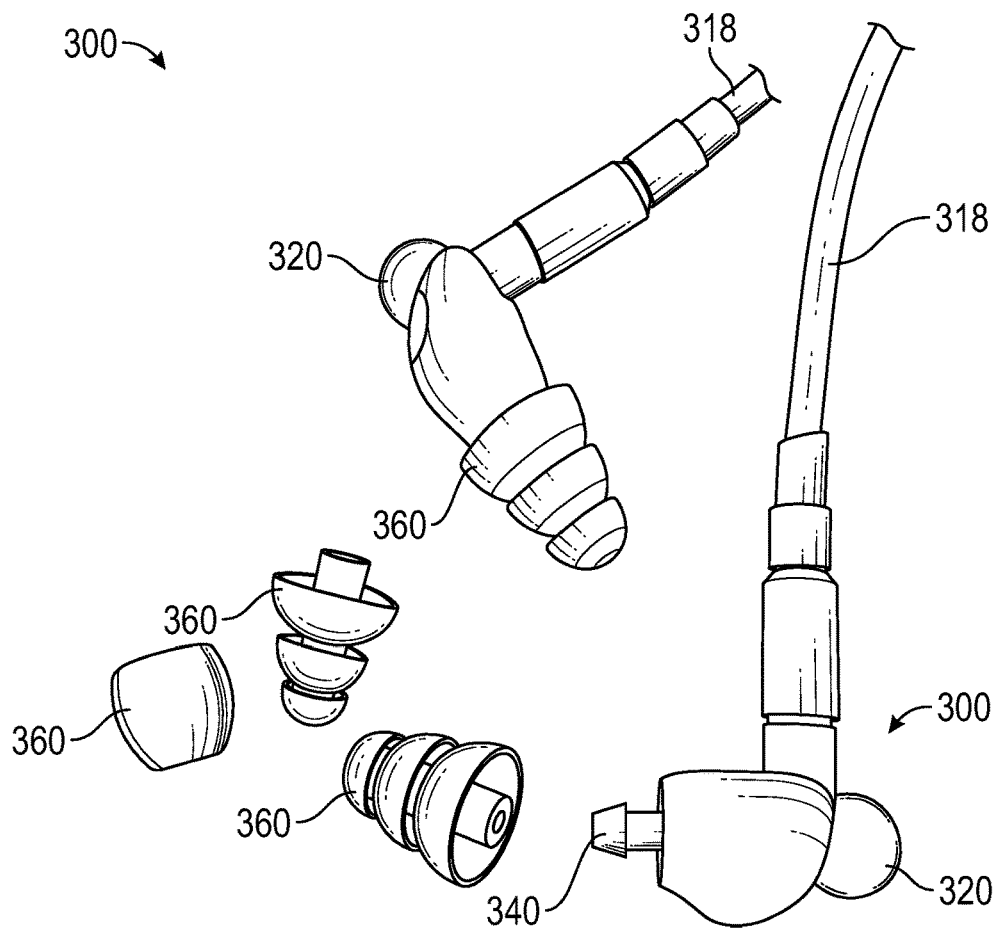
FIG. 13 is a side view of an example earpiece with examples of earbuds.

FIGS. 11A and 11B shows example embodiments of earpieces 300, which can be used with various embodiments disclosed herein, and can have features similar to various embodiments disclosed herein. FIG. 12A shows a perspective view of the example embodiment of an earpiece 300. FIG. 12B shows a top view of the example embodiment of an earpiece 300. FIG. 12C shows a side view of the example embodiment of an earpiece 300. FIG. 13 shows another example embodiment of a pair of earpieces 300. The system can include two earpieces 300 in some embodiments, or a single earpiece 300 in other embodiments. The earpiece 300 can have a concha portion 320, which can be configured to engage the concha of a subject's ear, such as to help secure the earpiece 300 to the ear. The concha portion 320 can be sized and shaped to generally correspond to the size and shape of the concha. In some cases, different concha portions 320 can be used for different sizes or shapes of ears. A custom fit concha portion can be used in some cases. The concha portion 320 can have a hole 322 that extends therethrough, such as to enable to the concha portion 320 to deform or compress when engaged with the ear. The concha portion 320 can include a hollow area, which can enable the concha portion 320 to deform or compress.

The earpiece 300 can include a removable tip 360. The earpiece 300 can have an engagement portion 340 that is configured to releasably engage the tip 360. The engagement portion 340 can have a channel or fluid pathway that is in fluid communication with a fluid conduit (e.g., a tube) 318. A fluid (e.g., air) can be delivered through the fluid conduit 318, through the earpiece 300, and into the ear, such as for caloric and/or pressure treatment as discussed herein. The fluid can pass through the fluid pathway in the engagement portion 340 as the fluid is delivered to the ear (e.g., the external ear canal). The removable tip 360 can have a hole that is configured to receive the engagement portion 340 therein. The fluid can pass through the hole in the removable tip 360 as the fluid is delivered to the ear. The removable tip 360 can have a soft, resilient, flexible, or elastic material to enable the tip 360 to sufficiently seal with the ear (e.g., the external ear canal) so that a pressure differential can be produced and/or maintained between the external ear canal pressure and ambient pressure. Removable tips 360 of various different sizes, and shapes, and configurations can be used. Subjects having ears of different sizes can use tips 360 of different sizes. The removable tip 360 can include baffles, ribs, or other features to facilitate sealing against the ear. The tip 360 can be inserted into the external ear canal. In some embodiments, the tip 360 is not removable.

The earpiece 300 (e.g., the concha portion 320 and/or tip 360) can include a gel material (e.g., surrounded by a membrane) which can be deformable to conform to the shape of the ear. The earpiece can have a water gel crystal material that expands upon exposure to water. A hydrogel can be used. The earpiece can have a water reservoir. A barrier can separate the water reservoir from the water gel crystal material. The user can squeeze the earpiece to rupture the barrier, or to deform the barrier, or to otherwise compromise the barrier so that the water combines with the water gel crystal material, thereby causing a portion of the earpiece to expand. For example, the tip 360 can be inserted into the ear, and the water gel crystal material can then be used to cause the tip 360 to expand to facilitate sealing of the tip 360 with the ear. The concha portion 320 can expand to facilitate engagement with the concha of the ear. Many variations and alternatives are possible. Various other expanding materials can be used. In some cases an electrical signal or current can be applied to a barrier to rupture the barrier, to open the barrier, or to otherwise cause the expanding material to expand.

Figure 13A:
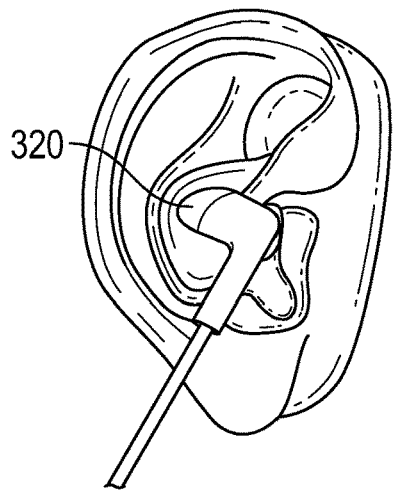
FIGS. 13A to 13C show example embodiments of an earpiece being engaged with an ear.
Figure 13B:
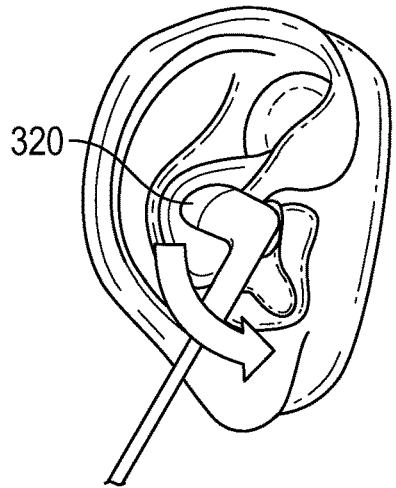
Figure 13C:
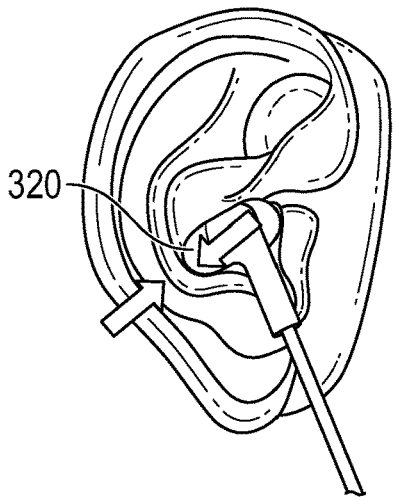

In some embodiments, the concha portion 320 can be configured to drive the tip 360 into the ear as the earpiece 300 is twisted. As the earpiece 300 is twisted, the concha portion 320 rides along the lower helical part of the ear and presses the tip 360 against the external ear canal, or otherwise facilitates engagement and/or sealing of the earpiece 300 with the ear, as shown in FIGS. 13A to 13C for example. The user can engage the earpiece 300 with the ear, for example as shown in FIG. 13A. The tip 360 can insert into the external ear canal. The concha portion 320 can be angled upward, as shown in FIG. 13A, although other positions are possible, such as horizontal or even angled slightly downward. As shown in FIGS. 13B and 13C, the user can move (e.g., rotate) the earpiece so that the concha portion 320 moves downward, which can cause the concha portion 320 to press against the helix of the ear (e.g., the lower helix), which can press the earpiece into the ear canal, and/or against the ear canal. In some cases, the concha portion 320 (or protrusion 320) can press against the ear (e.g., lower helix) to cause the portion of the earpiece in the ear canal to turn, which can help seal with the ear, and in some cases can hold the earpiece in engagement with the ear (e.g., which can counter the force of positive pressure that could tend to push the earpiece out of the ear).

In some embodiments, the concha portion 320 can inflate, such as to facilitate engagement of the earpiece 300 with the ear. The inflation can help seal the earpiece 300 with the ear. A manual pump can be used to inflate the concha portion 320. In some embodiments, a fluid channel (which can be separate from the fluid conduit 318) can deliver a fluid to the earpiece 300 to inflate one or more portions of the earpiece.

In some embodiments, the earpiece 300 can include one or more electrodes, which can be used to provide electrostimulation to the subject. The one or more electrodes can be coupled to the treatment device, such as by one or more wires, so that the treatment device can provide power and/or control signals to the one or more electrodes. The one or more wires can be inside the fluid conduit or tube, outside the fluid conduit or tube, or embedded into the wall of the fluid conduit or tube. The concha portion 320 can have one or more electrodes for stimulating one or more nerves on the concha of the ear. In some cases, the tip portion 360 can have one or more electrodes, such as for stimulating one or more nerves in the external ear canal. In some embodiments, the system can position an electrode at a location outside the ear, such as at the mastoid bone behind the ear. The earpiece 300 can have an arm that extends to along a back of the ear to position the electrode at the mastoid bone, for example. In some cases, the electrode configuration can be monopolar, such as using a single electrode. In some cases, the electrode configuration can be bipolar, such as having two electrodes (e.g., one in the external ear canal, and one in the concha). Other configurations of multiple electrodes can be used, including three or more electrodes. A bipolar configuration can be used with an electrode at the mastoid bone, and an electrode at the concha and/or ear canal. The earpiece can include a conductive flexible material for the one or more electrodes, such as a conductive polymer.

In some embodiments, a conductive material, such as liquid drops, or a conductive gel can be delivered to the ear canal to contact the tympanic membrane. Electrical current can be delivered to the tympanic membrane through the conductive material, such as using one or more electrodes. This can stimulate receptors on the tympanic membrane. In some embodiments, the conductive material can be delivered to the ear before the earpiece 300 is engaged with the ear. In some cases, the system can be configured to deliver a liquid, such as water, saline, an aqueous solution, etc. to the ear. The system can use a liquid to control pressure in the ear (e.g., hydraulically). The system can have a liquid reservoir, and a pressure generator configured to deliver liquid from the liquid reservoir to the ear. Pressure can be applied to the ear using the liquid in a manner similar to the disclosure herein relating to the use of air or other fluids. The liquid can be conductive, and electrical current can be delivered to the ear canal, tympanic membrane, and/or other portions of the ear using the conductive liquid.

In some cases, electro stimulation can be provided (e.g., to the tympanic membrane) while the tympanic membrane is preloaded by pressure. The treatment system can be used to apply pressure to the ear to displace the tympanic membrane. A negative pressure can pull the tympanic membrane, or a positive pressure can push the tympanic membrane. The system can then apply electrostimulation, while the tympanic membrane is displaced. This can produce neurological signals, which can be therapeutic, such as for treatment of migraines, headaches, or other neurological disorders.

In some embodiments, one or more electrodes on the earpiece can be used to determine whether the earpiece is engaged with the ear. For example, the earpiece can have two or more electrodes. If a current flows between the two or more electrodes, then the system can determine that the earpiece is engaged with the ear. If a current does not flow between the two or more electrodes, then the system can determine that the earpiece is not engaged with the ear. When the earpiece is not engaged with the ear, the electrodes can be insulated from each other (e.g., by air). When the earpiece is engaged with the ear, the one or more electrodes can be in electrical communication with each other, such as through ear or other tissue of the subject, such that a closed circuit can be established. In some embodiments, impedance can be measured to determine how well the earpiece is engaged with the ear.

Figure 14:
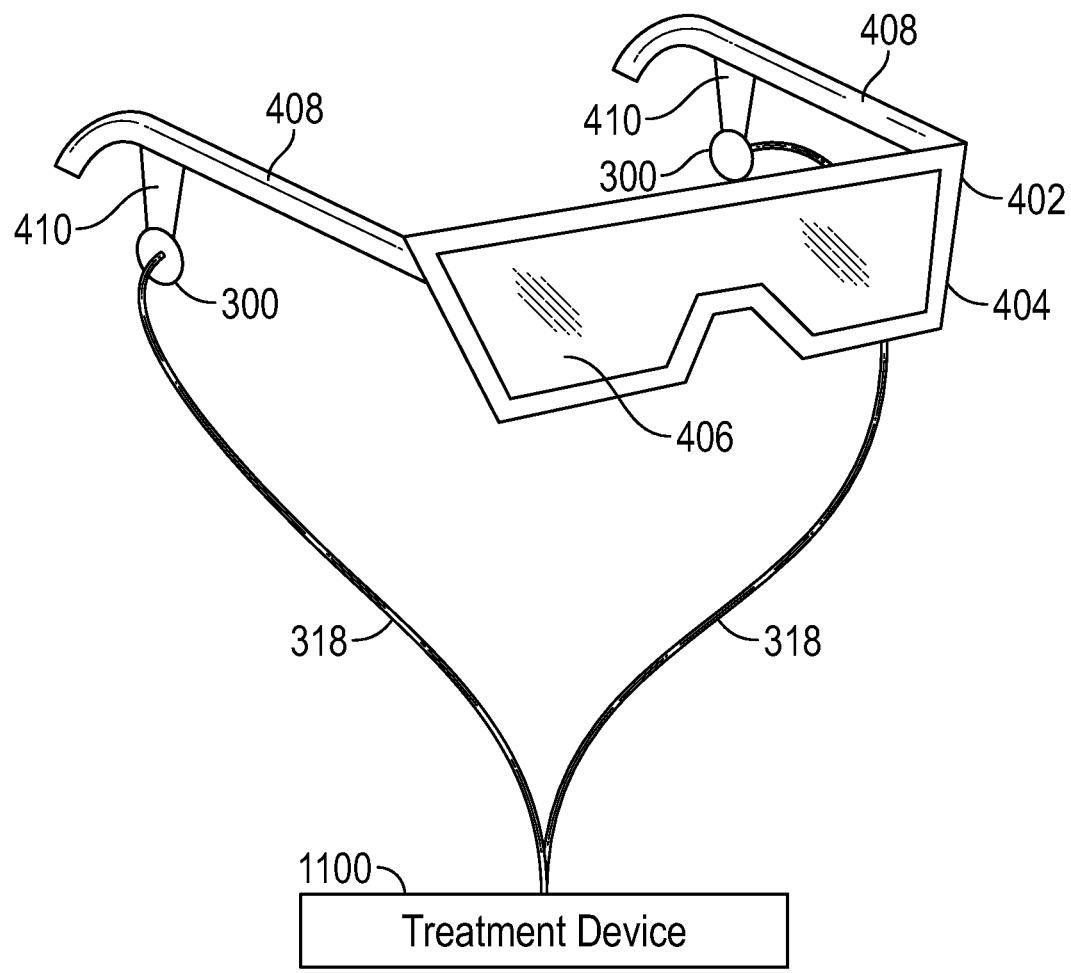
FIG. 14 shows an example embodiment of a treatment system that includes eyewear.

FIG. 14 shows an example embodiment of a treatment system that includes eyewear 400, such as glasses. The eyewear 402 can include a frame 404, which can be worn on the face of the subject. The eyewear 402 can have side arms 408, which can engage the ears to facilitate positioning of the eyewear 402. The eyewear 402 can have a lens 406, which can be supported by the frame 404. The frame 404 can position the lens 406 in front of the subject's eyes. The lens 406 can include a green filter that transmits more green light to the subject's eyes than light of other colors. When the subject looks through the lens 406, the lens 406 can cause the subject to see a green hue, which can be therapeutic. The green filter can have maximum transmission of light with a wavelength of about 535 nm, between about 525 nm and about 545 nm, between about 520 nm and about 560 nm, or between about 495 nm and about 570 nm.

One or more earpieces 300 can be coupled to the eyewear 402, so position the earpieces 300 to engage the ears when the eyewear 402 is worn by the subject. The one or more earpieces 300 can be coupled to one or more side arms 408 of the eyewear 402. A coupling mechanism 410 can couple the earpiece 300 to the side arm 408. The coupling mechanism 410 can include a clamp, a snap fitting, a friction fitting, adhesive, or any other suitable coupling features. In some cases, the side arm 408 can have an engagement feature, such as an indentation or protrusion or specially shaped portion which can receive or engage the coupling mechanism 410. In some embodiments, the earpiece 300 can be movable between multiple positions. For example, the coupling mechanism 410 can slide forward and/or rearward on the side arm 408. In some cases, a friction fitting can permit the coupling mechanism (e.g., and the earpiece 300) to slide along the side arm 408 when manipulated deliberately, and the friction fitting can impede unintended sliding of the coupling mechanism 410 along the side arm 408, such as when not being pushed or pulled. In some embodiments, the coupling mechanism can include a lock, which can be locked to hold the earpiece 300 in place, and can be unlocked to enable the earpiece 300 to be moved relative to the eyewear 402 (e.g., along the side arm 408). In some cases, the coupling mechanism 410 can include a biasing member, such as a spring, a flexible arm, etc. for biasing the earpiece 300 inward to facilitate insertion of the earpiece 300 into the ear, and/or to facilitate sealing of the earpiece 300 with the ear.

The earpiece 300 can be similar to the various earpieces disclosed herein. The system can include a treatment device 1100, which can be similar to the other embodiments disclosed herein. The system can include one or more fluid conduits 318 (e.g., tubes), which can be similar to the other embodiments disclosed herein. The system can include various other features disclosed herein, such as a valve module, a mobile device controller, a temperature modifier, electrodes, etc. In some cases, a headband or other wearable article can be used to facilitate positioning of the one or more earpieces 300.

Other Variations

Various other modifications, adaptations, and alternative designs are of course possible in light of the above teachings. Therefore, it should be understood at this time that within the scope of the appended claims the invention may be practiced otherwise than as specifically described herein.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "regulating external ear pressure" includes "instructing the regulation of external ear pressure." The ranges disclosed herein also encompass any and all overlap, subranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

Each of the processes, methods, instructions, applications and algorithms described in the preceding sections may be embodied in, and fully or partially automated by, code modules executed by one or more computer systems or computer processors comprising computer hardware. The code modules (or "engines") may be stored on any type of non-transitory computer-readable medium or computer storage device, such as hard drives, solid state memory, optical disc, and/or the like. The systems and modules may also be transmitted as generated data signals (for example, as part of a carrier wave or other analog or digital propagated signal) on a variety of computer-readable transmission mediums, including wireless-based and wired/cable-based mediums, and may take a variety of forms (for example, as part of a single or multiplexed analog signal, or as multiple discrete digital packets or frames). The processes and algorithms may be implemented partially or wholly in application-specific circuitry. The results of the disclosed processes and process steps may be stored, persistently or otherwise, in any type of non-transitory computer storage such as, for example, volatile or non-volatile storage.

User interfaces described herein are optionally presented (and user instructions may be received) via a user computing device using a browser, other network resource viewer, a dedicated application, or otherwise. Various features described or illustrated as being present in different embodiments or user interfaces may be combined into the same embodiment or user interface. Commands and information received from the user may be stored and acted on by the various systems disclosed herein using the processes disclosed herein. While the disclosure may reference to a user hovering over, pointing at, or clicking on a particular item, other techniques may be used to detect an item of user interest. For example, the user may touch the item via a touch screen, or otherwise indicate an interest. The user interfaces described herein may be presented on a user terminal, such as a laptop computer, desktop computer, tablet computer, smart phone, virtual reality headset, augmented reality headset, or other terminal type. The user terminals may be associated with user input devices, such as touch screens, microphones, touch pads, keyboards, mice, styluses, cameras, etc. While the foregoing discussion and figures may illustrate various types of menus, other types of menus may be used. For example, menus may be provided via a drop down menu, a tool bar, a pop up menu, interactive voice response system, or otherwise.

In general, the terms "engine" and "module", as used herein, refer to logic embodied in hardware or firmware, or to a collection of software instructions, possibly having entry and exit points, written in a programming language, such as, for example, Java, Lua, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software modules configured for execution on computing devices may be provided on a computer readable medium, such as a compact disc, digital video disc, flash drive, or any other tangible medium. Such software code may be stored, partially or fully, on a memory device of the executing computing device. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware. Generally, the modules described herein refer to logical modules that may be combined with other modules or divided into sub-modules despite their physical organization or storage. Electronic data sources can include databases, volatile/non-volatile memory, and any memory system or subsystem that maintains information.

The various features and processes described above may be used independently of one another, or may be combined in various ways. All possible combinations and subcombinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

Conditional language used herein, such as, among others, "can," "could," "might," "may," "for example," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is otherwise understood with the context as used in general to convey that an item, term, etc. may be either X, Y or Z. Thus, such conjunctive language is not generally intended to imply that certain embodiments require at least one of X, at least one of Y and at least one of Z to each be present.

The term "a" as used herein should be given an inclusive rather than exclusive interpretation. For example, unless specifically noted, the term "a" should not be understood to mean "exactly one" or "one and only one"; instead, the term "a" means "one or more" or "at least one," whether used in the claims or elsewhere in the specification and regardless of uses of quantifiers such as "at least one," "one or more," or "a plurality" elsewhere in the claims or specification.

The term "comprising" as used herein should be given an inclusive rather than exclusive interpretation. For example, a general purpose computer comprising one or more processors should not be interpreted as excluding other computer components, and may possibly include such components as memory, input/output devices, and/or network interfaces, among others.

While certain example embodiments have been described, these embodiments have been presented by way of example only, and are not intended to limit the scope of the disclosure. Nothing in the description is intended to imply that any particular element, feature, characteristic, step, module, or block is necessary or indispensable. The novel methods and systems described herein may be embodied in a variety of other forms; furthermore, various omissions, substitutions, and changes in the form of the methods and systems described herein may be made without departing from the spirit of the inventions disclosed herein. The accompanying claims and their equivalents are intended to cover such forms or modifications as would fall within the scope and spirit of certain of the inventions disclosed herein.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

It should be emphasized that many variations and modifications may be made to the above-described embodiments, the elements of which are to be understood as being among other acceptable examples. All such modifications and variations are intended to be included herein within the scope of the disclosure. The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated.

The invention claimed is:

1. A treatment system comprising:
an earpiece;
a fluid flow generator;
a fluid conduit extending between the fluid flow generator and the earpiece;
an outlet valve; and
a controller configured to:
operate the treatment system in an irrigation mode by:
opening the outlet valve; and
operating the fluid flow generator to apply a flow of fluid through the fluid conduit, through the earpiece, and out the outlet valve to an ambient area; and
operate the treatment system in a pressure mode by:
closing the outlet valve; and
operating the fluid flow generator to apply a pressure differential between an external ear canal pressure and an ambient pressure.

2. The treatment system of claim 1, wherein the earpiece comprises an outer surface configured to sealably engage an external ear canal sufficiently to provide a barrier between the external ear canal pressure and the ambient pressure, and wherein the treatment system is configured to transition between the irrigation mode and the pressure mode while the earpiece remains sealably engaged with the external ear canal.

3. The treatment system of claim 1, further comprising a temperature modifier, wherein the controller is configured to operate the temperature modifier to change a temperature of the fluid during the irrigation mode.

4. The treatment system of claim 3, wherein the controller is configured to operate the treatment system in the pressure mode after operating the treatment system in the irrigation mode to heat the external ear canal.

5. The treatment system of claim 3, wherein the temperature modifier comprises a heater.

6. The treatment system of claim 1, wherein a second fluid conduit extends between the earpiece and the outlet valve.

7. The treatment system of claim 6, comprising a valve module that includes the outlet valve, wherein the fluid conduit extends through the valve module.

8. The treatment system of claim 1, wherein the outlet valve comprises an outlet check valve configured to permit fluid to flow through the outlet valve to the ambient area and to impede fluid from flowing from the ambient area in through the outlet valve.

9. The treatment system of claim 1, comprising a pressure sensor, wherein the controller is configured to use information from the pressure sensor for feedback control to implement a pressure treatment profile.

10. The treatment system of claim 1, comprising a valve module that includes the outlet valve, wherein the valve module further comprises an inlet check valve configured to permit fluid to flow from an ambient environment into the valve module in the irrigation mode.

11. The treatment system of claim 1, comprising an actuator configured to open and close the outlet valve in response to electrical signals.

12. The treatment system of claim 1, further comprising:
an additional earpiece for use in an additional ear; and
an additional fluid conduit extending between the fluid flow generator and the additional earpiece.

13. The treatment system of claim 12, wherein the controller is configured to:
open the outlet valve and operate the fluid flow generator to apply a flow of fluid through the additional fluid conduit, through the additional earpiece, and out the outlet valve to an ambient area in the irrigation mode; and
close the outlet valve and operate the fluid flow generator to apply a pressure differential between an external ear canal pressure of the additional ear and the ambient pressure in the pressure mode.

14. The treatment system of claim 12, having a first configuration that directs fluid flow toward the earpiece while impeding fluid flow toward the additional earpiece, and having a second configuration that directs fluid flow to the additional earpiece while impeding fluid flow to the earpiece.

15. The treatment system of claim 14, having a third configuration that directs fluid flow toward both the earpiece and the additional earpiece.

16. The treatment system of claim 14, comprising an actuator configured to transition the outlet valve between the first configuration and the second configuration in response to electrical signals.

* * * * *